(12) United States Patent
Mellor et al.

(10) Patent No.: US 8,628,922 B2
(45) Date of Patent: Jan. 14, 2014

(54) SCREENING METHOD FOR CELL AGING

(75) Inventors: Elizabeth Jane Mellor, Oxford (GB); Michael Youdell, Oxford (GB); Anitha Nair, Oxford (GB); Alexandre Akoulitchev, Ewelme (GB)

(73) Assignee: Chronos Therapeutics Limited (GB)

( * ) Notice: Subject to any disclaimer, the term of this patent is extended or adjusted under 35 U.S.C. 154(b) by 0 days.

(21) Appl. No.: 13/382,629

(22) PCT Filed: Jul. 8, 2010

(86) PCT No.: PCT/GB2010/051128
§ 371 (c)(1),
(2), (4) Date: Feb. 17, 2012

(87) PCT Pub. No.: WO2011/004197
PCT Pub. Date: Jan. 13, 2011

(65) Prior Publication Data
US 2012/0270213 A1    Oct. 25, 2012

(30) Foreign Application Priority Data

Jul. 8, 2009 (GB) .................................. 0911885.2

(51) Int. Cl.
*C12Q 1/68* (2006.01)

(52) U.S. Cl.
USPC ............ 435/6.11; 435/375; 435/7.1; 435/7.9; 540/456

(58) Field of Classification Search
None
See application file for complete search history.

(56) References Cited

U.S. PATENT DOCUMENTS

2003/0207325 A1    11/2003    Guarente et al.
2006/0234250 A1    10/2006    Powers, III et al.

OTHER PUBLICATIONS

Fujii et al. (Human Mol. Genetics 2003, vol. 12: 1791-1800).*
Pray-Grant (Molecular and Cellular Biol. 2002: 8774-8786).*
Guelman et al. (Molecular and Cellular Biol. Mar. 2009: 1176-1188).*
International Search Report, PCT/GB2010/051128 (Nov. 23, 2010).
Kim et al., The histone acetyltransferase GCN5 modulates the retrograde response and genome stability determining yeast longevity, Biogerontology; 5:5, 305-316 (Oct. 2004).
Barros et al., Higher Respiratory Activity Decreases Mitochondrial Reactive Oxygen Release and Increases Life Span in *Saccharomyces cerevisiae*, J Biol Chem, 279:48, 49883-49888 (Nov. 26, 2004).
Lin et al., Sip2, an N-Myristoylated β Subunit of Snf1 Kinase, Regulates Aging in *Saccharomyces cerevisiae* by Affecting Cellular Histone Kinase Activity, Recombination at rDNA Loci, and Silensing, J Biol Chem, 278:15, 13390-13397 (Apr. 11, 2003).
Lorenz. et al., A network biology approach to aging in yeast, PNAS, 106:4, 1145-1150 (Jan. 27, 2009).
Powers III et al., Extension of chronological life span in yeast by decreased TOR pathway signaling, Genes Dev., 20:2, 174-184 (Jan. 2006).
Ashrafi et al., Sip2p and its partner Snf1p kinase affect aging in *S. cerevisiae*, Genes Dev., 14:15, 1872-1885 (Aug. 1, 2000).
Friis et al., A glycolytic burst drives glucose induction of global histone acetylation by picNuA4 and SAGA, Nucleic Acids Research, 37:12, 3969-3980 (Apr. 30, 2009).
Baker et al., The SAGA continues: expanding the cellular role of a transcriptional co-activator complex, Oncogene, 26:37, 5329-5340 (Aug. 13, 2007).
Sterner et al., SALSA, a variant of yeast SAGA, contains truncated Spt7, which correlates with activated transcription, PNAS, 99:18, 11622-11627 (Sep. 3, 2002).
Jiang et al., Global assessment of combinatorial post-translational modification of core histones in yeast using contemporary mass spectrometry, J Biol Chem, 282:38, 27923-27934 (Sep. 2007).
Kunz et al., Cyclosporin A, FK506 and rapamycin: more than just immunosuppression, TIBS 18, 334-338 (1993).
Pray-Grant et al., The novel SLIK histone acetyltransferase complex functions in the yeast retrograde response pathway, Mol Cell Biol 22:24, 8774-8786 (2002).
Wu et al., Analysis of Spt7 function in the *Saccharomyces cerevisiae* SAGA coactivator complex, Mol Cell Biol 22:15, 5367-5379 (2002).
Smith et al., Calorie restriction extends the chronological lifespan of *Saccharomyces cerevisiae* independently of the Sirtuins, Aging Cell 6, 649-662 (2007).
Lo et al., Snf1—a Histone Kinase That Works in Concert with the Histone Acetyltransferase Gcn5 to Regulate Transcription. Science 293, 1142-1146 (2001).

* cited by examiner

*Primary Examiner* — Kimberly Chong
(74) *Attorney, Agent, or Firm* — Caesar, Rivise, Bernstein, Cohen & Pokotilow, Ltd.

(57) ABSTRACT

The present invention relates to a method for increasing the chronological lifespan of a cell comprising disrupting the function of at least one of the SAGA1 SLIK and/or SALSA complexes in said cell.

4 Claims, 22 Drawing Sheets

SEQUENCE LISTING

<160> NUMBER OF SEQ ID NOS: 22

<210> SEQ ID NO 1
<211> LENGTH: 824
<212> TYPE: PRT
<213> ORGANISM: Saccharomyces cerevisiae

<400> SEQUENCE: 1

```
Met Met Asn Phe Phe Thr Ser Lys Ser Ser Asn Gln Asp Thr Gly Phe
1               5                   10                  15

Ser Ser Gln His Gln His Pro Asn Gly Gln Asn Asn Gly Asn Asn Asn
            20                  25                  30

Ser Ser Thr Ala Gly Asn Asp Asn Gly Tyr Pro Cys Lys Leu Val Ser
        35                  40                  45
```

-continued

```
Ser Gly Pro Cys Ala Ser Ser Asn Asn Gly Ala Leu Phe Thr Asn Phe
     50                  55                  60

Thr Leu Gln Thr Ala Thr Pro Thr Thr Ala Ile Ser Gln Asp Leu Tyr
65                  70                  75                  80

Ala Met Gly Thr Thr Gly Ile Thr Ser Glu Asn Ala Leu Phe Gln Met
                     85                  90                  95

Lys Ser Met Asn Asn Gly Ile Ser Ser Val Asn Asn Asn Ser Asn
                100                 105                 110

Thr Pro Thr Ile Ile Thr Thr Ser Gln Glu Glu Thr Asn Ala Gly Asn
                115                 120                 125

Val His Gly Asp Thr Gly Gly Asn Ser Leu Gln Asn Ser Glu Asp Asp
                130                 135                 140

Asn Phe Ser Ser Ser Thr Thr Lys Cys Leu Leu Ser Ser Thr Ser
145                 150                 155                 160

Ser Leu Ser Ile Asn Gln Arg Glu Ala Ala Ala Ala Tyr Gly Pro
                     165                 170                 175

Asp Thr Asp Ile Pro Arg Gly Lys Leu Glu Val Thr Ile Ile Glu Ala
                180                 185                 190

Arg Asp Leu Val Thr Arg Ser Lys Asp Ser Gln Pro Tyr Val Val Cys
                195                 200                 205

Thr Phe Glu Ser Ser Glu Phe Ile Ser Asn Gly Pro Glu Ser Leu Gly
                210                 215                 220

Ala Ile Asn Asn Asn Asn Asn Asn Asn Asn Asn Gln His Asn Gln
225                 230                 235                 240

Asn Gln His Ile Asn Asn Asn Glu Asn Thr Asn Pro Asp Ala Ala
                     245                 250                 255

Ser Gln His His Asn Asn Asn Ser Gly Trp Asn Gly Ser Gln Leu Pro
                260                 265                 270

Ser Ile Lys Glu His Leu Lys Lys Lys Pro Leu Tyr Thr His Arg Ser
                275                 280                 285

Ser Ser Gln Leu Asp Gln Leu Asn Ser Cys Ser Ser Val Thr Asp Pro
290                 295                 300

Ser Lys Arg Ser Ser Asn Ser Ser Ser Gly Ser Ser Asn Gly Pro Lys
305                 310                 315                 320

Asn Asp Ser Ser His Pro Ile Trp His His Lys Thr Thr Phe Asp Val
                325                 330                 335

Leu Gly Ser His Ser Glu Leu Asp Ile Ser Val Tyr Asp Ala Ala His
                340                 345                 350

Asp His Met Phe Leu Gly Gln Val Arg Leu Tyr Pro Met Ile His Asn
                355                 360                 365

Leu Ala His Ala Ser Gln His Gln Trp His Ser Leu Lys Pro Arg Val
                370                 375                 380

Ile Asp Glu Val Val Ser Gly Asp Ile Leu Ile Lys Trp Thr Tyr Lys
385                 390                 395                 400

Gln Thr Lys Lys Arg His Tyr Gly Pro Gln Asp Phe Glu Val Leu Arg
                405                 410                 415

Leu Leu Gly Lys Gly Thr Phe Gly Gln Val Tyr Gln Val Lys Lys Lys
                420                 425                 430

Asp Thr Gln Arg Ile Tyr Ala Met Lys Val Leu Ser Lys Lys Val Ile
                435                 440                 445

Val Lys Lys Asn Glu Ile Ala His Thr Ile Gly Glu Arg Asn Ile Leu
450                 455                 460

Val Thr Thr Ala Ser Lys Ser Ser Pro Phe Ile Val Gly Leu Lys Phe
```

|     |     |     | 465 |     |     |     | 470 |     |     |     | 475 |     |     |     | 480 |
| --- | --- | --- | --- | --- | --- | --- | --- | --- | --- | --- | --- | --- | --- | --- | --- |
| Ser | Phe | Gln | Thr | Pro | Thr | Asp | Leu | Tyr | Leu | Val | Thr | Asp | Tyr | Met | Ser |
|     |     |     |     | 485 |     |     |     |     | 490 |     |     |     |     | 495 |     |

Gly Gly Glu Leu Phe Trp His Leu Gln Lys Glu Gly Arg Phe Ser Glu
            500                 505                 510

Asp Arg Ala Lys Phe Tyr Ile Ala Glu Leu Val Leu Ala Leu Glu His
            515                 520                 525

Leu His Asp Asn Asp Ile Val Tyr Arg Asp Leu Lys Pro Glu Asn Ile
        530                 535                 540

Leu Leu Asp Ala Asn Gly Asn Ile Ala Leu Cys Asp Phe Gly Leu Ser
545                 550                 555                 560

Lys Ala Asp Leu Lys Asp Arg Thr Asn Thr Phe Cys Gly Thr Thr Glu
                565                 570                 575

Tyr Leu Ala Pro Glu Leu Leu Leu Asp Glu Thr Gly Tyr Thr Lys Met
            580                 585                 590

Val Asp Phe Trp Ser Leu Gly Val Leu Ile Phe Glu Met Cys Cys Gly
        595                 600                 605

Trp Ser Pro Phe Phe Ala Glu Asn Asn Gln Lys Met Tyr Gln Lys Ile
610                 615                 620

Ala Phe Gly Lys Val Lys Phe Pro Arg Asp Val Leu Ser Gln Glu Gly
625                 630                 635                 640

Arg Ser Phe Val Lys Gly Leu Leu Asn Arg Asn Pro Lys His Arg Leu
                645                 650                 655

Gly Ala Ile Asp Asp Gly Arg Glu Leu Arg Ala His Pro Phe Phe Ala
            660                 665                 670

Asp Ile Asp Trp Glu Ala Leu Lys Gln Lys Ile Pro Pro Phe
        675                 680                 685

Lys Pro His Leu Val Ser Glu Thr Asp Thr Ser Asn Phe Asp Pro Glu
        690                 695                 700

Phe Thr Thr Ala Ser Thr Ser Tyr Met Asn Lys His Gln Pro Met Met
705                 710                 715                 720

Thr Ala Thr Pro Leu Ser Pro Ala Met Gln Ala Lys Phe Ala Gly Phe
                725                 730                 735

Thr Phe Val Asp Glu Ser Ala Ile Asp Glu His Val Asn Asn Asn Arg
            740                 745                 750

Lys Phe Leu Gln Asn Ser Tyr Phe Met Glu Pro Gly Ser Phe Ile Pro
        755                 760                 765

Gly Asn Pro Asn Leu Pro Pro Asp Glu Asp Val Ile Asp Asp Asp Gly
770                 775                 780

Asp Glu Asp Ile Asn Asp Gly Phe Asn Gln Glu Lys Asn Met Asn Asn
785                 790                 795                 800

Ser His Ser Gln Met Asp Phe Asp Gly Asp Gln His Met Asp Asp Glu
                805                 810                 815

Phe Val Ser Gly Arg Phe Glu Ile
            820

<210> SEQ ID NO 2
<211> LENGTH: 2475
<212> TYPE: DNA
<213> ORGANISM: Saccharomyces cerevisiae

<400> SEQUENCE: 2
atgatgaatt ttttacatc aaaatcgtcg aatcaggata ctggatttag ctctcaacac    60
caacatccaa atggacagaa caatggaaac aataatagca gcaccgctgg caacgacaac   120

```
ggatacccat gtaaactggt gtccagtggg ccctgcgctt catcaaataa tggtgccctt    180
tttacgaatt ttactttaca aactgcaacg ccgaccaccg ctattagtca ggacttatat    240
gcaatgggca caacaggaat aacatcagaa aatgcccttt ttcaaatgaa gtcaatgaat    300
aatgaaatat catcagttaa taataacaac agcaacaccc ctacgattat taccacgtca    360
caggaagaaa ctaatgctgg aaatgtacat ggcgataccg gtggcaattc tttgcaaaat    420
tctgaagatg acaacttttc ttccagttct accaccaaat gcttactctc ttccacttct    480
tcgctatcaa taaatcaacg agaagcagca gcagctgctt atggtccaga taccgatatt    540
cctaggggta aactagaagt tacaataata gaagcacgtg acctagtcac tagatcaaag    600
gattcacagc cttatgttgt ttgtactttt gagagttcag agttcatttc taatggtcct    660
gagtcactag gcgccattaa taataacaac aataacaaca acaataatca gcataatcaa    720
aaccagcata ttaacaacaa caacgaaaat accaaccctg acgctgctag ccagcatcat    780
aataataaca gtggttggaa cggttctcag ttaccatcga taaagagca cttgaagaaa    840
aaacccottt atacacacag atcatcttcc caattagatc agctaaactc ttgctcttca    900
gtaaccgatc cgagcaaacg ttcttctaat tcttcgtcgg gttcttcaaa tggtccaaag    960
aatgatagtt cacatccaat atggcatcac aagacaacgt ttgatgtttt gggatctcac   1020
tcggaattag atatttctgt ttatgatgct gcccacgacc atatgttctt aggccaagtt   1080
agactgtatc caatgattca taatttagca catgcttccc aacaccaatg gcacagtttg   1140
aaacctcgcg ttattgatga agttgtgtcc ggtgatattt taatcaaatg gacttacaaa   1200
cagacaaaga aaagacatta tggcccacaa gattttgaag ttcttcgatt attgggtaag   1260
ggtacttttg gccaagtcta ccaagttaag aagaaagaca ctcaaagaat ttatgcaatg   1320
aaagttctct ccaagaaagt tattgtcaag aaaaatgaga tcgcccacac aattggcgaa   1380
agaaatatcc tagtcacgac agcgtccaaa tcgtccccat tcattgtcgg attgaagttt   1440
tcctttcaaa caccaacaga tctgtatttg gtcactgatt atatgagtgg tggagaatta   1500
ttctggcatt tacaaaagga gggccgtttt tcggaagaca gagcgaaatt ctatatcgct   1560
gagttagtcc tagcgttaga acatttacac gataacgata tcgtttacag ggacctaaag   1620
cctgaaaaca ttctactcga tgccaacggt aacatcgctc tttgcgattt tggtctttct   1680
aaagctgact tgaaggatag aacaaacaca ttttgcggca ccacggaata cctggcacca   1740
gaattgttac tggacgaaac cggctacacc aaaatggtcg atttctggtc tctaggtgtt   1800
ttgatatttg aaatgtgttg tggttggtcc ccttttcttg cggaaaataa tcaaaaaatg   1860
taccaaaaaa ttgcctttgg taaagtcaaa ttccccagag acgtactgtc acaagagggg   1920
aggtcttttg taaagggttt actaaacaga accccaaac atagactcgg tgccattgat   1980
gatggaagag aactacgagc tcatccattt ttcgcagata tcgactggga ggccttgaag   2040
cagaaaaaaa ttccaccacc tttcaaacct cacctagtct cggagacgga tacctcgaat   2100
tttgacccag agttcacaac agcttcaact tcatacatga acaagcacca gccgatgatg   2160
actgctaccc cgctatctcc agccatgcaa gcaaagtttg ctggtttcac ctttgttgat   2220
gagtccgcca tcgatgaaca cgttaataac aacagaaaat tcctacaaaa ctcgtacttt   2280
atggaacctg gttcctttat cccgggaaat ccaaacttac ctccagacga agatgtcatc   2340
gatgatgacg gggacgagga catcaatgat ggattcaacc aagagaaaaa tatgaacaac   2400
agccattcgc agatggactt cgacggcgac caacacatgg atgacgaatt tgtcagtgga   2460
agattcgaaa tatga                                                    2475
```

<210> SEQ ID NO 3
<211> LENGTH: 588
<212> TYPE: PRT
<213> ORGANISM: Saccharomyces cerevisiae

<400> SEQUENCE: 3

```
Met Ser Thr Leu Ser Asp Ser Asp Thr Glu Thr Glu Val Val Ser Arg
1               5                   10                  15

Asn Leu Cys Gly Ile Val Asp Ile Gly Ser Asn Gly Ile Arg Phe Ser
            20                  25                  30

Ile Ser Ser Lys Ala Ala His His Ala Arg Ile Met Pro Cys Val Phe
        35                  40                  45

Lys Asp Arg Val Gly Leu Ser Leu Tyr Glu Val Gln Tyr Asn Thr His
    50                  55                  60

Thr Asn Ala Lys Cys Pro Ile Pro Arg Asp Ile Ile Lys Glu Val Cys
65                  70                  75                  80

Ser Ala Met Lys Arg Phe Lys Leu Ile Cys Asp Asp Phe Gly Val Pro
                85                  90                  95

Glu Thr Ser Val Arg Val Ile Ala Thr Glu Ala Thr Arg Asp Ala Ile
            100                 105                 110

Asn Ala Asp Glu Phe Val Asn Ala Val Tyr Gly Ser Thr Gly Trp Lys
        115                 120                 125

Val Glu Ile Leu Gly Gln Glu Asp Glu Thr Arg Val Gly Ile Tyr Gly
    130                 135                 140

Val Val Ser Ser Phe Asn Thr Val Arg Gly Leu Tyr Leu Asp Val Ala
145                 150                 155                 160

Gly Gly Ser Thr Gln Leu Ser Trp Val Ile Ser Ser His Gly Glu Val
                165                 170                 175

Lys Gln Ser Ser Lys Pro Val Ser Leu Pro Tyr Gly Ala Gly Thr Leu
            180                 185                 190

Leu Arg Arg Met Arg Thr Asp Asp Asn Arg Ala Leu Phe Tyr Glu Ile
        195                 200                 205

Lys Glu Ala Tyr Lys Asp Ala Ile Glu Lys Ile Gly Ile Pro Gln Glu
    210                 215                 220

Met Ile Asp Asp Ala Lys Lys Glu Gly Gly Phe Asp Leu Trp Thr Arg
225                 230                 235                 240

Gly Gly Gly Leu Arg Gly Met Gly His Leu Leu Tyr Gln Ser Glu
                245                 250                 255

Gly Tyr Pro Ile Gln Thr Ile Ile Asn Gly Tyr Ala Cys Thr Tyr Glu
            260                 265                 270

Glu Phe Ser Ser Met Ser Asp Tyr Leu Phe Leu Lys Gln Lys Ile Pro
        275                 280                 285

Gly Ser Ser Lys Glu His Lys Ile Phe Lys Val Ser Asp Arg Arg Ala
    290                 295                 300

Leu Gln Leu Pro Ala Val Gly Leu Phe Met Ser Ala Val Phe Glu Ala
305                 310                 315                 320

Ile Pro Gln Ile Lys Ala Val His Phe Ser Glu Gly Gly Val Arg Glu
                325                 330                 335

Gly Ser Leu Tyr Ser Leu Leu Pro Lys Glu Ile Arg Ala Gln Asp Pro
            340                 345                 350

Leu Leu Ile Ala Ser Arg Pro Tyr Ala Pro Leu Leu Thr Glu Lys Tyr
        355                 360                 365

Leu Tyr Leu Leu Arg Thr Ser Ile Pro Gln Glu Asp Ile Pro Glu Ile
    370                 375                 380
```

```
Val Asn Glu Arg Ile Ala Pro Ala Leu Cys Asn Leu Ala Phe Val His
385                 390                 395                 400

Ala Ser Tyr Pro Lys Glu Leu Gln Pro Thr Ala Ala Leu His Val Ala
            405                 410                 415

Thr Arg Gly Ile Ile Ala Gly Cys His Gly Leu Ser His Arg Ala Arg
        420                 425                 430

Ala Leu Ile Gly Ile Ala Leu Cys Ser Arg Trp Gly Gly Asn Ile Pro
    435                 440                 445

Glu Ser Glu Glu Lys Tyr Ser Gln Glu Leu Glu Gln Val Val Leu Arg
450                 455                 460

Glu Gly Asp Lys Ala Glu Ala Leu Arg Ile Val Trp Trp Thr Lys Tyr
465                 470                 475                 480

Ile Gly Thr Ile Met Tyr Val Ile Cys Gly Val His Pro Gly Gly Asn
            485                 490                 495

Ile Arg Asp Asn Val Phe Asp Phe His Val Ser Lys Arg Ser Glu Val
        500                 505                 510

Glu Thr Ser Leu Lys Glu Leu Ile Asp Asp Ala Asn Thr Thr Lys
    515                 520                 525

Val Lys Glu Glu Ser Thr Arg Lys Asn Arg Gly Tyr Glu Val Val Val
530                 535                 540

Arg Ile Ser Lys Asp Asp Leu Lys Thr Ser Ala Ser Val Arg Ser Arg
545                 550                 555                 560

Ile Ile Thr Leu Gln Lys Lys Val Arg Lys Leu Ser Arg Gly Ser Val
            565                 570                 575

Glu Arg Val Lys Ile Gly Val Gln Phe Tyr Glu Glu
        580                 585

<210> SEQ ID NO 4
<211> LENGTH: 1767
<212> TYPE: DNA
<213> ORGANISM: Saccharomyces cerevisiae

<400> SEQUENCE: 4
atgtcaacac ttagcgatag tgataccgag actgaggtcg tgtcgagaaa cttgtgtgga    60
atcgtcgaca taggttctaa tggtattcgt tttagtatat cttccaaggc tgcacatcat   120
gcaagaatta tgccttgtgt ttttaaagat agggttggtc tttctctata cgaagttcaa   180
tataatacac atacgaacgc aaaatgccct attcccagag atattataaa agaggtttgt   240
tctgccatga agagattcaa attaatttgc gatgattttg gtgtacctga actagtgtc    300 agagtaattg caacagaagc cacgcgagat gctattaacg cggatgaatt tgttaatgct   360
gtttacggta gcactggctg aaagtagaa atattaggcc aggaagatga aactagggtc    420
ggcatatatg gtgttgtttc ctcatttaat acagtaagag gtctatatct agatgtggca   480
ggtggtagta ctcagttatc atgggtaata agctcgcacg gagaagtcaa gcaatccagc   540
aaacctgtat ctttgccata tggagctgga actcttttga aagaatgag aacagatgat   600 aatagggcac ttttttatga gattaaagaa gcgtacaaag atgcgattga aaaaattggt   660
atacctcaag aaatgattga tgacgccaag aaagaaggtg gatttgacct tggacccgt    720 gggggtggtt taagaggtat gggacatctg cttctttacc agtcggaagg ttatcccatc   780
caaacaataa ttaacggata tgcttgcact tatgaagaat tctcgtctat gtcagattat   840
ctattcctaa acaaaaaat accaggttct tcaaaagagc ataaaatatt taaggtttct   900
gatagaaggg ctttacaact tcctgccgtt ggtttgttca tgagtgctgt tttgaagcg    960 attccccaga tcaaagctgt acattttagt gagggtggtg ttcgagaggg ttcacttat   1020
```

```
tctcttcttc caaagaaat tcgtgcacaa gatccattgc taattgcgtc ccgtccttat      1080
gctccattac ttactgaaaa atatctatat ctattgagaa catcaatccc acaagaagat      1140
ataccagaaa tagtaaacga aaggattgct cctgctttat gtaacttagc atttgttcat      1200
gcctcttatc caaggagtt acaaccaaca gctgcattac atgttgctac aagagggata      1260
atagccggct gtcatggatt atctcacaga gctagagcgc tgataggaat tgctctatgt      1320
agtagatggg gcggcaacat tccggaatct gaagaaaaat actcccaaga attagaacaa      1380
gtagttctac gcgaaggtga taaagctgaa gcattgagaa ttgtatggtg gacgaagtat      1440
attggtacga ttatgtatgt gatttgcggt gttcatccag gtggtaatat cagagataac      1500
gtatttgatt ccatgtttc taagcgtagt gaggtggaga ccagtttaaa agaattaatc      1560
attgatgatg caaacactac aaaggtaaaa gaagaatcca cgcgtaaaaa tcgcgggtat      1620
gaagtggttg tgagaattag taaggacgat cttaaaacaa gtgcttccgt tcgttccaga      1680
attatcacgc tacaaaagaa agtacgcaag ctatctagag gaagtgtaga gagggttaaa      1740
attggcgtgc aattttatga agaataa                                         1767
```

<210> SEQ ID NO 5
<211> LENGTH: 439
<212> TYPE: PRT
<213> ORGANISM: Saccharomyces cerevisiae

<400> SEQUENCE: 5

```
Met Val Thr Lys His Gln Ile Glu Glu Asp His Leu Asp Gly Ala Thr
1               5                   10                  15

Thr Asp Pro Glu Val Lys Arg Val Lys Leu Glu Asn Asn Val Glu Glu
            20                  25                  30

Ile Gln Pro Glu Gln Ala Glu Thr Asn Lys Gln Glu Gly Thr Asp Lys
        35                  40                  45

Glu Asn Lys Gly Lys Phe Glu Lys Glu Thr Glu Arg Ile Gly Gly Ser
    50                  55                  60

Glu Val Val Thr Asp Val Glu Lys Gly Ile Val Lys Phe Glu Phe Asp
65                  70                  75                  80

Gly Val Glu Tyr Thr Phe Lys Glu Arg Pro Ser Val Val Glu Glu Asn
                85                  90                  95

Glu Gly Lys Ile Glu Phe Arg Val Val Asn Asn Asp Asn Thr Lys Glu
            100                 105                 110

Asn Met Met Val Leu Thr Gly Leu Lys Asn Ile Phe Gln Lys Gln Leu
        115                 120                 125

Pro Lys Met Pro Lys Glu Tyr Ile Ala Arg Leu Val Tyr Asp Arg Ser
    130                 135                 140

His Leu Ser Met Ala Val Ile Arg Lys Pro Leu Thr Val Val Gly Gly
145                 150                 155                 160

Ile Thr Tyr Arg Pro Phe Asp Lys Arg Glu Phe Ala Glu Ile Val Phe
                165                 170                 175

Cys Ala Ile Ser Ser Thr Glu Gln Val Arg Gly Tyr Gly Ala His Leu
            180                 185                 190

Met Asn His Leu Lys Asp Tyr Val Arg Asn Thr Ser Asn Ile Lys Tyr
        195                 200                 205

Phe Leu Thr Tyr Ala Asp Asn Tyr Ala Ile Gly Tyr Phe Lys Lys Gln
    210                 215                 220

Gly Phe Thr Lys Glu Ile Thr Leu Asp Lys Ser Ile Trp Met Gly Tyr
225                 230                 235                 240
```

```
Ile Lys Asp Tyr Glu Gly Gly Thr Leu Met Gln Cys Ser Met Leu Pro
                245                 250                 255

Arg Ile Arg Tyr Leu Asp Ala Gly Lys Ile Leu Leu Leu Gln Glu Ala
            260                 265                 270

Ala Leu Arg Arg Lys Ile Arg Thr Ile Ser Lys Ser His Ile Val Arg
        275                 280                 285

Pro Gly Leu Glu Gln Phe Lys Asp Leu Asn Asn Ile Lys Pro Ile Asp
    290                 295                 300

Pro Met Thr Ile Pro Gly Leu Lys Glu Ala Gly Trp Thr Pro Glu Met
305                 310                 315                 320

Asp Ala Leu Ala Gln Arg Pro Lys Arg Gly Pro His Asp Ala Ala Ile
                325                 330                 335

Gln Asn Ile Leu Thr Glu Leu Gln Asn His Ala Ala Ala Trp Pro Phe
            340                 345                 350

Leu Gln Pro Val Asn Lys Glu Glu Val Pro Asp Tyr Tyr Asp Phe Ile
        355                 360                 365

Lys Glu Pro Met Asp Leu Ser Thr Met Glu Ile Lys Leu Glu Ser Asn
    370                 375                 380

Lys Tyr Gln Lys Met Glu Asp Phe Ile Tyr Asp Ala Arg Leu Val Phe
385                 390                 395                 400

Asn Asn Cys Arg Met Tyr Asn Gly Glu Asn Thr Ser Tyr Tyr Lys Tyr
                405                 410                 415

Ala Asn Arg Leu Glu Lys Phe Phe Asn Asn Lys Val Lys Glu Ile Pro
            420                 425                 430

Glu Tyr Ser His Leu Ile Asp
        435

<210> SEQ ID NO 6
<211> LENGTH: 2128
<212> TYPE: DNA
<213> ORGANISM: Saccharomyces cerevisiae

<400> SEQUENCE: 6
tcttaaacac ttatgggcag caaaaaatgc gtctttcttc cctcgtctgt tgttttatgt      60
agggcgtaat gatgtttgct tgtcaacaaa tgaatacgta cagaagagaa ttctagccaa     120
ggcaattatt gcatactgca agtactgagt acgttaacgt tgctagaata acattaaatg     180
agatgtagca atgcagatcc ttcctcagta ggcttaatgc tccactagaa ttttttgacca    240 gccactattt gctttttttcg caatcctttt caatactcga gagcaaagac aaaaaaaata    300
agacatgtag tgcgctgtat ggaaaagaat taattagaac tttacaaacg cgtgttaaac    360
aggcatattt aagtgtttgg acctaaacaa tatatcgact attgaaattc ttacgcaaga    420
ttttttatag ttggatattc atatattctt acaactctct ctactttcag ttttttgaag    480
ctatatgtat cattatatac gtttatggat ttttcaaacc taaacaatta tactgcgtaa    540
atgtttgatt aagcaataaa taaaacaaa ggattggtaa gggaagaccg tgagccgccc     600
aaaagtcttc agttaactca ggttcgtatt ctacattaga tggtcacaaa acatcagatt    660
gaagaggatc acttggatgg agctacgacg gatcccgaag ttaaacgggt aaaattagaa    720
aacaacgttg aagaaataca acctgagcag gctgagacca ataacaaga gggcaccgat    780 aaagagaata aggaaagtt cgagaaagaa actgagagaa taggaggatc tgaagtggtt    840
acagatgtgg aaaaaggaat tgtcaaattt gaatttgatg gtgttgaata cacattcaaa    900
gagagaccca gtgtcgtaga ggaaaatgaa ggtaaaattg agtttagggt ggtgaataat    960
gataatacta agaaaaacat gatggtccta actggattaa aaaacatttt tcaaaagcaa   1020
```

```
ttaccaaaaa tgcccaaaga atacattgcc aggttagtct atgatcgaag tcatctttcc    1080
atggctgtca ttaggaagcc attgactgtc gtaggtggca taacatatcg acctttcgat    1140
aagagagaat tcgcagaaat tgttttctgt gccatcagtt cgacggaaca ggtacgcggt    1200
tatggtgcgc atctaatgaa tcacttaaaa gactatgtta gaaataccte gaacataaaa    1260 tattttttga catatgcaga taattacgct attggatact ttaaaaagca aggcttcact    1320
aaagaaatca cgttggataa aagtatatgg atgggatata ttaaagatta tgaaggtggt    1380
acgctgatgc aatgttctat gttaccaaga atacgatatt tggacgcagg taagattcta    1440
ttattacaag aagcggccct gcgaagaaaa ataagaacga tttcgaaatc gcatattgta    1500
aggcctggtt tagagcaatt caaagactta acaatatca aaccgattga tccaatgact    1560
attcctggct tgaaagaagc cggctggact cccgagatgg atgcgttggc acaacgtccc    1620
aagcgtggtc cacacgatgc agcaatacag aatatactca cagagctaca aaatcatgca    1680
gcagcttggc ccttcttaca acccgttaat aaagaggagg tccccgacta ttatgatttt    1740
atcaaagagc caatggactt gagcaccatg gaaataaaat tagagagcaa caaatatcag    1800
aagatggaag acttcatata tgatgccaga ttggtgttta acaattgccg aatgtacaat    1860
ggcgagaata cgtcgtatta caagtatgct aataggctag agaaattctt caataataaa    1920
gtaaaagaaa tacctgaata ttctcacctt attgattaat gcgtagaaga agcttttccg    1980
ctactattcc tttcgaagaa gaaataaatg tttagtacgg cgagacgatg tgatcaattg    2040
aggttatttt actactttc ctttcatttt tgtaaggttt tctttctttg ttagtgtgac    2100
gttggtattt acctttatgt aactatat                                       2128
```

<210> SEQ ID NO 7
<211> LENGTH: 2470
<212> TYPE: PRT
<213> ORGANISM: Saccharomyces cerevisiae

<400> SEQUENCE: 7

```
Met Glu Pro His Glu Glu Gln Ile Trp Lys Ser Lys Leu Leu Lys Ala
1               5                  10                  15

Ala Asn Asn Asp Met Asp Met Asp Arg Asn Val Pro Leu Ala Pro Asn
            20                  25                  30

Leu Asn Val Asn Met Asn Met Lys Met Asn Ala Ser Arg Asn Gly Asp
        35                  40                  45

Glu Phe Gly Leu Thr Ser Ser Arg Phe Asp Gly Val Val Ile Gly Ser
    50                  55                  60

Asn Gly Asp Val Asn Phe Lys Pro Ile Leu Glu Lys Ile Phe Arg Glu
65                  70                  75                  80

Leu Thr Ser Asp Tyr Lys Glu Glu Arg Lys Leu Ala Ser Ile Ser Leu
                85                  90                  95

Phe Asp Leu Leu Val Ser Leu Glu His Glu Leu Ser Ile Glu Glu Phe
            100                 105                 110

Gln Ala Val Ser Asn Asp Ile Asn Asn Lys Ile Leu Glu Leu Val His
        115                 120                 125

Thr Lys Lys Thr Ser Thr Arg Val Gly Ala Val Leu Ser Ile Asp Thr
    130                 135                 140

Leu Ile Ser Phe Tyr Ala Tyr Thr Glu Arg Leu Pro Asn Glu Thr Ser
145                 150                 155                 160

Arg Leu Ala Gly Tyr Leu Arg Gly Leu Ile Pro Ser Asn Asp Val Glu
                165                 170                 175
```

-continued

```
Val Met Arg Leu Ala Ala Lys Thr Leu Gly Lys Leu Ala Val Pro Gly
                180                 185                 190
Gly Thr Tyr Thr Ser Asp Phe Val Glu Phe Glu Ile Lys Ser Cys Leu
            195                 200                 205
Glu Trp Leu Thr Ala Ser Thr Glu Lys Asn Ser Phe Ser Ser Ser Lys
        210                 215                 220
Pro Asp His Ala Lys His Arg Ala Leu Leu Ile Ile Thr Ala Leu Ala
225                 230                 235                 240
Glu Asn Cys Pro Tyr Leu Leu Tyr Gln Tyr Leu Asn Ser Ile Leu Asp
                245                 250                 255
Asn Ile Trp Arg Ala Leu Arg Asp Pro His Leu Val Ile Arg Ile Asp
            260                 265                 270
Ala Ser Ile Thr Leu Ala Lys Cys Leu Ser Thr Leu Arg Asn Arg Asp
        275                 280                 285
Pro Gln Leu Thr Ser Gln Trp Val Gln Arg Leu Ala Thr Ser Cys Glu
290                 295                 300
Tyr Gly Phe Gln Val Asn Thr Leu Glu Cys Ile His Ala Ser Leu Leu
305                 310                 315                 320
Val Tyr Lys Glu Ile Leu Phe Leu Lys Asp Pro Phe Leu Asn Gln Val
                325                 330                 335
Phe Asp Gln Met Cys Leu Asn Cys Ile Ala Tyr Glu Asn His Lys Ala
            340                 345                 350
Lys Met Ile Arg Glu Lys Ile Tyr Gln Ile Val Pro Leu Leu Ala Ser
        355                 360                 365
Phe Asn Pro Gln Leu Phe Ala Gly Lys Tyr Leu His Gln Ile Met Asp
370                 375                 380
Asn Tyr Leu Glu Ile Leu Thr Asn Ala Pro Ala Lys Lys Ile Pro His
385                 390                 395                 400
Leu Lys Asp Asp Lys Pro Gln Ile Leu Ile Ser Ile Gly Asp Ile Ala
                405                 410                 415
Tyr Glu Val Gly Pro Asp Ile Ala Pro Tyr Val Lys Gln Ile Leu Asp
            420                 425                 430
Tyr Ile Glu His Asp Leu Gln Thr Lys Phe Lys Phe Arg Lys Lys Phe
        435                 440                 445
Glu Asn Glu Ile Phe Tyr Cys Ile Gly Arg Leu Ala Val Pro Leu Gly
450                 455                 460
Pro Val Leu Gly Lys Leu Leu Asn Arg Asn Ile Leu Asp Leu Met Phe
465                 470                 475                 480
Lys Cys Pro Leu Ser Asp Tyr Met Gln Glu Thr Phe Gln Ile Leu Thr
                485                 490                 495
Glu Arg Ile Pro Ser Leu Gly Pro Lys Ile Asn Asp Glu Leu Leu Asn
            500                 505                 510
Leu Val Cys Ser Thr Leu Ser Gly Thr Pro Phe Ile Gln Pro Gly Ser
        515                 520                 525
Pro Met Glu Ile Pro Ser Phe Ser Arg Glu Arg Ala Arg Glu Trp Arg
530                 535                 540
Asn Lys Ser Ile Leu Gln Lys Thr Gly Glu Ser Asn Asp Asp Asn Asn
545                 550                 555                 560
Asp Ile Lys Ile Ile Ile Gln Ala Phe Arg Met Leu Lys Asn Ile Lys
                565                 570                 575
Ser Arg Phe Ser Leu Val Glu Phe Val Arg Ile Val Ala Leu Ser Tyr
            580                 585                 590
Ile Glu His Thr Asp Pro Arg Val Arg Lys Leu Ala Ala Leu Thr Ser
        595                 600                 605
```

```
Cys Glu Ile Tyr Val Lys Asp Asn Ile Cys Lys Gln Thr Ser Leu His
    610                 615                 620

Ser Leu Asn Thr Val Ser Glu Val Leu Ser Lys Leu Leu Ala Ile Thr
625                 630                 635                 640

Ile Ala Asp Pro Leu Gln Asp Ile Arg Leu Glu Val Leu Lys Asn Leu
                    645                 650                 655

Asn Pro Cys Phe Asp Pro Gln Leu Ala Gln Pro Asp Asn Leu Arg Leu
                660                 665                 670

Leu Phe Ile Ala Leu His Asp Glu Ser Phe Asn Ile Gln Ser Val Ala
            675                 680                 685

Met Glu Leu Val Gly Arg Leu Ser Ser Val Asn Pro Ala Tyr Val Ile
        690                 695                 700

Pro Ser Ile Arg Lys Ile Leu Glu Leu Leu Thr Lys Leu Lys Phe
705                 710                 715                 720

Ser Thr Ser Ser Arg Glu Lys Glu Thr Ala Ser Leu Leu Cys Thr
                    725                 730                 735

Leu Ile Arg Ser Ser Lys Asp Val Ala Lys Pro Tyr Ile Glu Pro Leu
                740                 745                 750

Leu Asn Val Leu Leu Pro Lys Phe Gln Asp Thr Ser Ser Thr Val Ala
            755                 760                 765

Ser Thr Ala Leu Arg Thr Ile Gly Glu Leu Ser Val Val Gly Gly Glu
        770                 775                 780

Asp Met Lys Ile Tyr Leu Lys Asp Leu Phe Pro Leu Ile Ile Lys Thr
785                 790                 795                 800

Phe Gln Asp Gln Ser Asn Ser Phe Lys Arg Glu Ala Ala Leu Lys Ala
                    805                 810                 815

Leu Gly Gln Leu Ala Ala Ser Ser Gly Tyr Val Ile Asp Pro Leu Leu
                820                 825                 830

Asp Tyr Pro Glu Leu Leu Gly Ile Leu Val Asn Ile Leu Lys Thr Glu
            835                 840                 845

Asn Ser Gln Asn Ile Arg Arg Gln Thr Val Thr Leu Ile Gly Ile Leu
        850                 855                 860

Gly Ala Ile Asp Pro Tyr Arg Gln Lys Glu Arg Glu Val Thr Ser Thr
865                 870                 875                 880

Thr Asp Ile Ser Thr Glu Gln Asn Ala Pro Pro Ile Asp Ile Ala Leu
                    885                 890                 895

Leu Met Gln Gly Met Ser Pro Ser Asn Asp Glu Tyr Tyr Thr Thr Val
                900                 905                 910

Val Ile His Cys Leu Leu Lys Ile Leu Lys Asp Pro Ser Leu Ser Ser
            915                 920                 925

Tyr His Thr Ala Val Ile Gln Ala Ile Met His Ile Phe Gln Thr Leu
        930                 935                 940

Gly Leu Lys Cys Val Ser Phe Leu Asp Gln Ile Ile Pro Thr Ile Leu
945                 950                 955                 960

Asp Val Met Arg Thr Cys Ser Gln Ser Leu Leu Glu Phe Tyr Phe Gln
                    965                 970                 975

Gln Leu Cys Ser Leu Ile Ile Ile Val Arg Gln His Ile Arg Pro His
                980                 985                 990

Val Asp Ser Ile Phe Gln Ala Ile  Lys Asp Phe Ser Ser  Val Ala Lys
            995                 1000                1005

Leu Gln  Ile Thr Leu Val Ser  Val Ile Glu Ala Ile  Ser Lys Ala
    1010                1015                1020

Leu Glu  Gly Glu Phe Lys Arg  Leu Val Pro Leu Thr  Leu Thr Leu
```

-continued

```
              1025                1030                1035
Phe Leu Val Ile Leu Glu Asn Asp Lys Ser Asp Lys Val Leu
    1040                1045                1050

Ser Arg Arg Val Leu Arg Leu Leu Glu Ser Phe Gly Pro Asn Leu
    1055                1060                1065

Glu Gly Tyr Ser His Leu Ile Thr Pro Lys Ile Val Gln Met Ala
    1070                1075                1080

Glu Phe Thr Ser Gly Asn Leu Gln Arg Ser Ala Ile Ile Thr Ile
    1085                1090                1095

Gly Lys Leu Ala Lys Asp Val Asp Leu Phe Glu Met Ser Ser Arg
    1100                1105                1110

Ile Val His Ser Leu Leu Arg Val Leu Ser Ser Thr Thr Ser Asp
    1115                1120                1125

Glu Leu Ser Lys Val Ile Met Asn Thr Leu Ser Leu Leu Leu Ile
    1130                1135                1140

Gln Met Gly Thr Ser Phe Ala Ile Phe Ile Pro Val Ile Asn Glu
    1145                1150                1155

Val Leu Met Lys Lys His Ile Gln His Thr Ile Tyr Asp Asp Leu
    1160                1165                1170

Thr Asn Arg Ile Leu Asn Asn Asp Val Leu Pro Thr Lys Ile Leu
    1175                1180                1185

Glu Ala Asn Thr Thr Asp Tyr Lys Pro Ala Glu Gln Met Glu Ala
    1190                1195                1200

Ala Asp Ala Gly Val Ala Lys Leu Pro Ile Asn Gln Ser Val Leu
    1205                1210                1215

Lys Ser Ala Trp Asn Ser Ser Gln Gln Arg Thr Lys Glu Asp Trp
    1220                1225                1230

Gln Glu Trp Ser Lys Arg Leu Ser Ile Gln Leu Leu Lys Glu Ser
    1235                1240                1245

Pro Ser His Ala Leu Arg Ala Cys Ser Asn Leu Ala Ser Met Tyr
    1250                1255                1260

Tyr Pro Leu Ala Lys Glu Leu Phe Asn Thr Ala Phe Ala Cys Val
    1265                1270                1275

Trp Thr Glu Leu Tyr Ser Gln Tyr Gln Glu Asp Leu Ile Glu Ser
    1280                1285                1290

Leu Cys Ile Ala Leu Ser Ser Pro Leu Asn Pro Pro Glu Ile His
    1295                1300                1305

Gln Thr Leu Leu Asn Leu Val Glu Phe Met Glu His Asp Asp Lys
    1310                1315                1320

Ala Leu Pro Ile Pro Thr Gln Ser Leu Gly Glu Tyr Ala Glu Arg
    1325                1330                1335

Cys His Ala Tyr Ala Lys Ala Leu His Tyr Lys Glu Ile Lys Phe
    1340                1345                1350

Ile Lys Glu Pro Glu Asn Ser Thr Ile Glu Ser Leu Ile Ser Ile
    1355                1360                1365

Asn Asn Gln Leu Asn Gln Thr Asp Ala Ala Ile Gly Ile Leu Lys
    1370                1375                1380

His Ala Gln Gln His His Ser Leu Gln Leu Lys Glu Thr Trp Phe
    1385                1390                1395

Glu Lys Leu Glu Arg Trp Glu Asp Ala Leu His Ala Tyr Asn Glu
    1400                1405                1410

Arg Glu Lys Ala Gly Asp Thr Ser Val Ser Val Thr Leu Gly Lys
    1415                1420                1425
```

```
Met Arg Ser Leu His Ala Leu Ala Glu Trp Glu Gln Leu Ser Gln
1430                1435                1440

Leu Ala Ala Arg Lys Trp Lys Val Ser Lys Leu Gln Thr Lys Lys
1445                1450                1455

Leu Ile Ala Pro Leu Ala Ala Gly Ala Arg Gly Gly Ser Gly Glu
1460                1465                1470

Trp Asp Met Leu Asp Glu Tyr Ile Ser Val Met Lys Pro Lys Ser
1475                1480                1485

Pro Asp Lys Glu Phe Phe Asp Ala Ile Leu Tyr Leu His Lys Asn
1490                1495                1500

Asp Tyr Asp Asn Ala Ser Lys His Ile Leu Asn Ala Arg Asp Leu
1505                1510                1515

Leu Val Thr Glu Ile Ser Ala Leu Ile Asn Glu Ser Tyr Asn Arg
1520                1525                1530

Ala Tyr Ser Val Ile Val Arg Thr Gln Ile Ile Thr Glu Phe Glu
1535                1540                1545

Glu Ile Ile Lys Tyr Lys Gln Leu Pro Pro Asn Ser Glu Lys Lys
1550                1555                1560

Leu His Tyr Gln Asn Leu Trp Thr Lys Arg Leu Leu Gly Cys Gln
1565                1570                1575

Lys Asn Val Asp Leu Trp Gln Arg Val Leu Arg Ile Arg Ser Leu
1580                1585                1590

Val Ile Lys Pro Lys Gln Asp Leu Gln Ile Trp Ile Lys Phe Ala
1595                1600                1605

Asn Leu Cys Arg Lys Ser Gly Arg Met Arg Leu Ala Asn Lys Ala
1610                1615                1620

Leu Asn Met Leu Leu Glu Gly Gly Thr Ile Leu Val Tyr Gln Ile
1625                1630                1635

Arg Ser Lys Pro Pro Pro Val Val Tyr Ala Gln Leu Lys Tyr
1640                1645                1650

Ile Trp Ala Thr Gly Ala Tyr Lys Glu Ala Leu Asn His Leu Ile
1655                1660                1665

Gly Phe Thr Ser Arg Leu Ala His Asp Leu Gly Leu Asp Pro Asn
1670                1675                1680

Asn Met Ile Ala Gln Ser Val Lys Leu Ser Ser Ala Ser Thr Ala
1685                1690                1695

Pro Tyr Val Glu Glu Tyr Thr Lys Leu Leu Ala Arg Cys Phe Leu
1700                1705                1710

Lys Gln Gly Glu Trp Arg Ile Ala Thr Gln Pro Asn Trp Arg Asn
1715                1720                1725

Thr Asn Pro Asp Ala Ile Leu Gly Ser Tyr Leu Leu Ala Thr His
1730                1735                1740

Phe Asp Lys Asn Trp Tyr Lys Ala Trp His Asn Trp Ala Leu Ala
1745                1750                1755

Asn Phe Glu Val Ile Ser Met Val Gln Glu Glu Thr Lys Leu Asn
1760                1765                1770

Gly Gly Lys Asn Asp Asp Asp Asp Thr Ala Val Asn Asn Asp
1775                1780                1785

Asn Val Arg Ile Asp Gly Ser Ile Leu Gly Ser Gly Ser Leu Thr
1790                1795                1800

Ile Asn Gly Asn Arg Tyr Pro Leu Glu Leu Ile Gln Arg His Val
1805                1810                1815

Val Pro Ala Ile Lys Gly Phe Phe His Ser Ile Ser Leu Leu Glu
1820                1825                1830
```

-continued

```
Thr Ser Cys Leu Gln Asp Thr Leu Arg Leu Ser Thr Leu Leu Phe
    1835                1840                1845

Asn Phe Gly Gly Ile Lys Glu Val Ser Gln Ala Met Tyr Glu Gly
    1850                1855                1860

Phe Asn Leu Met Lys Ile Glu Asn Trp Leu Glu Val Leu Pro Gln
    1865                1870                1875

Leu Ile Ser Arg Ile His Gln Pro Asp Pro Thr Val Ser Asn Ser
    1880                1885                1890

Leu Leu Ser Leu Leu Ser Asp Leu Gly Lys Ala His Pro Gln Ala
    1895                1900                1905

Leu Val Tyr Pro Leu Thr Val Ala Ile Lys Ser Glu Ser Val Ser
    1910                1915                1920

Arg Gln Lys Ala Ala Leu Ser Ile Ile Glu Lys Ile Arg Ile His
    1925                1930                1935

Ser Pro Val Leu Val Asn Gln Ala Glu Leu Val Ser His Glu Leu
    1940                1945                1950

Ile Arg Val Ala Val Leu Trp His Glu Leu Trp Tyr Glu Gly Leu
    1955                1960                1965

Glu Asp Ala Ser Arg Gln Phe Phe Val Glu His Asn Ile Glu Lys
    1970                1975                1980

Met Phe Ser Thr Leu Glu Pro Leu His Lys His Leu Gly Asn Glu
    1985                1990                1995

Pro Gln Thr Leu Ser Glu Val Ser Phe Gln Lys Ser Phe Gly Arg
    2000                2005                2010

Asp Leu Asn Asp Ala Tyr Glu Trp Leu Asn Asn Tyr Lys Lys Ser
    2015                2020                2025

Lys Asp Ile Asn Asn Leu Asn Gln Ala Trp Asp Ile Tyr Tyr Asn
    2030                2035                2040

Val Phe Arg Lys Ile Thr Arg Gln Ile Pro Gln Leu Gln Thr Leu
    2045                2050                2055

Asp Leu Gln His Val Ser Pro Gln Leu Leu Ala Thr His Asp Leu
    2060                2065                2070

Glu Leu Ala Val Pro Gly Thr Tyr Phe Pro Gly Lys Pro Thr Ile
    2075                2080                2085

Arg Ile Ala Lys Phe Glu Pro Leu Phe Ser Val Ile Ser Ser Lys
    2090                2095                2100

Gln Arg Pro Arg Lys Phe Ser Ile Lys Gly Ser Asp Gly Lys Asp
    2105                2110                2115

Tyr Lys Tyr Val Leu Lys Gly His Glu Asp Ile Arg Gln Asp Ser
    2120                2125                2130

Leu Val Met Gln Leu Phe Gly Leu Val Asn Thr Leu Leu Lys Asn
    2135                2140                2145

Asp Ser Glu Cys Phe Lys Arg His Leu Asp Ile Gln Gln Tyr Pro
    2150                2155                2160

Ala Ile Pro Leu Ser Pro Lys Ser Gly Leu Leu Gly Trp Val Pro
    2165                2170                2175

Asn Ser Asp Thr Phe His Val Leu Ile Arg Glu His Arg Asp Ala
    2180                2185                2190

Lys Lys Ile Pro Leu Asn Ile Glu His Trp Val Met Leu Gln Met
    2195                2200                2205

Ala Pro Asp Tyr Glu Asn Leu Thr Leu Leu Gln Lys Ile Glu Val
    2210                2215                2220

Phe Thr Tyr Ala Leu Asp Asn Thr Lys Gly Gln Asp Leu Tyr Lys
```

| | | | | | | | | | | |
|---|---|---|---|---|---|---|---|---|---|---|
| | | 2225 | | | 2230 | | | 2235 | | |

Ile Leu Trp Leu Lys Ser Arg Ser Ser Glu Thr Trp Leu Glu Arg
2240                 2245                 2250

Arg Thr Thr Tyr Thr Arg Ser Leu Ala Val Met Ser Met Thr Gly
2255                 2260                 2265

Tyr Ile Leu Gly Leu Gly Asp Arg His Pro Ser Asn Leu Met Leu
2270                 2275                 2280

Asp Arg Ile Thr Gly Lys Val Ile His Ile Asp Phe Gly Asp Cys
2285                 2290                 2295

Phe Glu Ala Ala Ile Leu Arg Glu Lys Tyr Pro Glu Lys Val Pro
2300                 2305                 2310

Phe Arg Leu Thr Arg Met Leu Thr Tyr Ala Met Glu Val Ser Gly
2315                 2320                 2325

Ile Glu Gly Ser Phe Arg Ile Thr Cys Glu Asn Val Met Arg Val
2330                 2335                 2340

Leu Arg Asp Asn Lys Glu Ser Leu Met Ala Ile Leu Glu Ala Phe
2345                 2350                 2355

Ala Leu Asp Pro Leu Ile His Trp Gly Phe Asp Leu Pro Pro Gln
2360                 2365                 2370

Lys Leu Thr Glu Gln Thr Gly Ile Pro Leu Pro Leu Ile Asn Pro
2375                 2380                 2385

Ser Glu Leu Leu Arg Lys Gly Ala Ile Thr Val Glu Glu Ala Ala
2390                 2395                 2400

Asn Met Glu Ala Glu Gln Gln Asn Glu Thr Arg Asn Ala Arg Ala
2405                 2410                 2415

Met Leu Val Leu Arg Arg Ile Thr Asp Lys Leu Thr Gly Asn Asp
2420                 2425                 2430

Ile Lys Arg Phe Asn Glu Leu Asp Val Pro Glu Gln Val Asp Lys
2435                 2440                 2445

Leu Ile Gln Gln Ala Thr Ser Ile Glu Arg Leu Cys Gln His Tyr
2450                 2455                 2460

Ile Gly Trp Cys Pro Phe Trp
2465                 2470

<210> SEQ ID NO 8
<211> LENGTH: 7413
<212> TYPE: DNA
<213> ORGANISM: Saccharomyces cerevisiae

<400> SEQUENCE: 8

| | |
|---|---|
| atggaaccgc atgaggagca gatttggaag agtaaacttt tgaaagcggc taacaacgat | 60 |
| atggacatgg atagaaatgt gccgttggca ccgaatctga atgtgaatat gaacatgaaa | 120 |
| atgaatgcga gcaggaacgg ggatgaattc ggtctgactt ctagtaggtt tgatggagtg | 180 |
| gtgattggca gtaatgggga tgtaaatttt aagcccattt tggagaaaat ttccgcgaa | 240 |
| ttaaccagtg attacaagga ggaacgaaaa ttggccagta tttcattatt tgatctacta | 300 |
| gtatccttgg aacatgaatt gtcgatagaa gagttccaag cagtttcaaa tgacataaac | 360 |
| aataagattt tggagctggt ccatacaaaa aaaacgagca ctagggtagg ggctgttcta | 420 |
| tccatagaca ctttgatttc attctacgca tatactgaaa ggttgcctaa cgaaacttca | 480 |
| cgactggctg gttaccttcg agggctaata ccttctaatg atgtagaggt catgagactc | 540 |
| gctgcaaaga ctctgggcaa gttagccgtt ccaggaggta catataccct tgatttcgtg | 600 |
| gaatttgaga taaagtcttg cttagaatgg cttactgcct ccacggaaaa gaattcattc | 660 |

```
tcgagttcga agccagacca tgctaaacat gctgcgcttc tgattataac agcgttggca    720
gagaattgtc cttatttact ctaccaatac ttgaattcca tactagataa catttggaga    780
gcactaagag acccacattt ggtgatcaga attgatgcgt ccattacatt ggccaaatgt    840 cttccaccc tacgaaatag ggatcctcag ttaactagcc agtgggtgca gagattggct     900
acaagttgtg aatacggatt tcaagtaaac acattagaat gcatccatgc aagtttgttg    960
gtttataagg aaatcttgtt tttgaaggat cccttttga atcaagtgtt cgaccaaatg     1020
tgtctaaatt gcatagctta tgaaaatcat aaagcgaaaa tgattagaga aagatttac     1080 cagattgttc ccctattagc atcgttcaat cctcaattat ttgctggcaa atatttgcac    1140
caaattatgg acaactattt agagatttta accaatgctc cagcaaataa aataccacat    1200
ctcaaagatg acaaaccaca gatttaata tcgattggtg atattgcata tgaagtcggg     1260
cccgatatcg caccttatgt gaaacaaatt cttgattata ttgaacatga tttacagacg    1320
aaattcaaat tcagaaagaa atttgaaaat gaaattttct actgcatcgg aagattggca    1380
gttcccttgg gccccgttct aggtaaatta ttaaacagaa atatactgga cctgatgttc    1440
aaatgccctc tttccgacta tatgcaggaa acgtttcaaa ttctgactga gagaatacca    1500
tcactaggcc ccaaaataaa tgacgagttg cttaacctag tctgttcaac cttatctgga    1560
acaccattta tccagccagg gtcaccaatg gagataccat cgttttcgag agaaagagca    1620
agagaatgga gaaataaaaa catcctacag aaaactggtg aaagtaacga tgataataat    1680
gatataaaaa tcattataca agcttttaga atgttaaaaa atatcaaaag cagattttcg    1740
ttggtggaat tcgtgagaat tgttgcactt tcttacattg agcatacaga tcccagagta    1800
aggaaactag ctgcgttgac atcttgtgaa attacgtca aggataacat ctgcaaacaa     1860
acatcactac actctctgaa cactgtatct gaagtgttat caaagcttct agccattacg    1920
attgcggacc ctttacaaga tatccgttta gaagttttaa agaatcttaa tccatgtttc    1980
gatccccagt tggcacaacc agataatttg agactcttgt ttactgcact gcacgatgag    2040
tcgttcaata ttcagtcagt agcaatggag cttgtcggta ggttgtcttc cgtaaaccct    2100
gcatacgtca tcccatcgat aagaaaaata ctactggaac tgctaacaaa attaaaattc    2160
tcaacttctt ctcgagaaaa ggaagaaact gccagtttgt tatgtactct tatcaggtcg    2220
agtaaagatg ttgcgaaacc ttatatcgaa cctcttttaa atgttctttt accaaaattc    2280
caagatacct cttcaacggt tgcatcaact gcactgagaa ctataggtga gctatctgtt    2340 gtaggggggcg aagatatgaa gatatatctt aaggatttgt ttcctttaat tatcaaaaca   2400
tttcaggatc aatcaaactc tttcaagaga gaagctgcac ttaaggccct tggtcaactt    2460
gcagcctcat ctggttacgt gatagatcct ttactcgact atcccgaatt attgggtata    2520
ttggtgaata tattgaagac agaaaactct caaaatatta ggagacaaac agtcactttg    2580
ataggtatac tgggagctat cgacccatat cgccaaaaag aacgtgaggt tacctctact    2640
accgatatat ctacagaaca gaacgccccg cctatcgaca ttgctcttct catgcagggc    2700
atgtctcctt cgaatgatga gtattatacc actgttgtca ttcactgcct gctaaaaatc    2760
ctaaaagatc catccctatc atcttaccac actgccgtga tccaagcgat tatgcatatt    2820
tttcaaaccc ttggtctaaa atgtgtttca ttccttggacc agatcatccc aactattttg    2880
gacgtaatgc gtacatgctc tcagtcacta ttagaatttt acttccaaca gctttgctct    2940
ttgattatta tcgtaaggca acacataaga cctcatgtcg attctatatt ccaggctatc    3000 aaagatttt cttcggttgc taagctacaa ataacgcttg taagtgttat tgaagcaata    3060
```

```
tcaaaggctc tggagggtga attcaaaaga ttggtccctc ttactctgac cttgttcctt    3120
gtaattttgg agaatgacaa gtctagtgac aaggtcctct ccagaagggt attgagactg    3180
ttagaatcgt ttggtcctaa cttagaaggt tattcgcatt tgattacacc caagatagtt    3240
caaatggcag aattcaccag cgggaaccta caaaggtctg caataattac tattggcaaa    3300
ctggccaagg atgttgacct ttttgagatg tcctcaagaa ttgttcactc tttacttagg    3360
gtactaagtt caacaacgag tgacgaactc tcaaaagtca ttatgaatac tttaagtcta    3420
ctgctaatac aaatgggcac atcctttgct atcttcatcc ctgtcattaa tgaagtttta    3480
atgaagaaac atattcaaca cacaatatat gatgacttga caaacagaat attaaacaat    3540
gatgttttac ccacaaaaat tcttgaagca aatacaacgg attataagcc cgcggaacaa    3600
atggaggcag cagatgctgg ggtcgcaaaa ttacctataa accaatcagt tttgaaaagt    3660
gcatggaatt ctagccaaca aagaactaaa gaagattggc aggaatggag caaacgtcta    3720
tccattcaat tattaaaaga gtcaccctcc catgctctaa gagcttgttc aaatcttgca    3780
agcatgtatt atccactagc caaagaactt tttaataccg cattcgcatg tgtttggacc    3840
gaactttata gccaatatca agaagattta attgggtcat tatgtatagc cttatcttct    3900
cccttaaatc caccagaaat acatcaaaca ttgttaaacc tggtagaatt tatggaacac    3960
gatgacaagg cattaccaat accaactcaa agcctgggcg agtatgctga agatgtcac    4020
gcctatgcca aagcgctaca ttataaagag attaaattta ttaaagagcc tgagaactca    4080
actattgaat cattgatcag cattaacaac cagctgaatc aaacggatgc tgcaattggt    4140
atattaaagc atgcccaaca acatcattca cttcaattaa aggagacatg gtttgaaaaa    4200
ttagagcgtt gggaagatgc actacatgct tataatgaac gtgaaaaggc aggtgatact    4260
tccgtgagcg ttacactcgg taagatgaga tcccttcatg cccttggcga atgggaacag    4320
ttgtcgcaat tggcagctag aaagtggaaa gtttcgaagc tacaaactaa gaagctaata    4380
gctcccttgg cagctggtgc tgcgtggggg ttgggagagt gggatatgct tgagcaatat    4440
atcagcgtta tgaaacctaa atctccagat aaggaatttt ttgatgcaat tttatacttg    4500
cacaagaatg attacgacaa tgctagtaag catatattaa cgccagaga tttgcttgtg    4560
actgaaattt ccgcgttgat caatgaaagt tataatagag catatagcgt tattgttaga    4620
actcaaaataa taacagagtt tgaggaaatc atcaagtata aacaattgcc acctaattcc    4680
gagaaaaaac ttcactatca aaatctttgg acaaaaagac tgctgggctg ccaaaaaaat    4740
gtcgattttat ggcaaagagt gcttagagta agatcattgg taataaagcc caagcaagac    4800
ctgcaaatat ggataaaatt tgcaaatttg tgcagaaaat ctggtagaat gaggctagca    4860
aataaggcat tgaatatgct actagaagga ggcaacgatc ctagtttacc aaatacgttc    4920
aaagctcctc ccccagttgt ttacgcgcaa ctaaaatata tttgggctac aggagcttat    4980
aaagaagcat taaccacttt gataggattt acatccaggt tagcgcatga tcttggtttg    5040
gatccgaata atatgatcgc gcaaagtgtc aaactctcaa gtgcaagtac tgctccgtat    5100
gttgaggaat acacaaaatt attagctcga tgttttttaa agcaaggtga gtggagaata    5160
gcaacacaac cgaactggag aaacacaaat ccggatgcaa ttcttggttc ttatctattg    5220
gctacacatt tcgataaaaa ttggtacaag gcatggcata attgggcctt agctaatttt    5280
gaagtaatat ccatggttca ggaagagact aagctcaacg gaggtaagaa tgatgatgat    5340
gatgacacgg cagttaataa tgataatgtg cggattgacg gtagtatcct aggaagtggt    5400
tctttgacta ttaatggcaa cagataccccg ctagagctta ttcaaagaca tgttgttcca    5460
```

```
gcgatcaagg gctttttca ttcaatatct ctattagaaa caagttgttt gcaagacacg    5520
ttgaggttat tgactctttt atttaacttt ggtggtatta agaagtctc acaagccatg    5580 tatgaaggct tcaatttgat gaaaatagag aactggcttg aagtcttacc acagttgatc    5640
tctcgtatac atcagccaga tcctacgtg agtaattccc ttttgtcgtt gctttctgat    5700
ttagggaaag ctcatccaca agctctcgtg tatcctttaa ctgtcgcgat caagtctgaa    5760
tctgtttcaa gacaaaaagc ggctcttca ataatagaga aaattaggat tcatagtcca    5820
gtcctggtaa accaggcaga attagttagt cacgagttga tcagagtagc cgttctatgg    5880
cacgaattat ggtatgaagg actggaagat gcgagccgcc aattttcgt tgaacataac    5940 atagaaaaaa tgttttctac tttagaacct ttacataaac acttaggcaa tgagcctcaa    6000
acgttaagtg aggtatcgtt tcagaaatca tttggtagag atttgaacga tgcctacgaa    6060
tggttgaata actacaaaaa gtcaaaagac atcaataatt tgaaccaagc ttgggatatt    6120
tattataacg tcttcagaaa aataacacgt caaataccac agttacaaac cttagactta    6180
cagcatgttt ctccccagct tctggctact catgatctcg aattggctgt tcctgggaca    6240
tatttcccag gaaaacctac cattagaata gcgaagtttg agccattatt ttctgtgatc    6300
tcttcgaagc aaaggccaag aaaattctcc atcaagggta gcgacggtaa agattataaa    6360 tacgtttaa agggacatga agatataaga caagatagcc ttgttatgca attatttggt    6420
ctagttaaca ctttgttgaa gaatgattca gagtgtttca agagacattt ggatatccaa    6480
caatacccgg ctattccatt gtcgcctaaa tctggtttac taggatgggt accaaatagt    6540
gacacattcc acgttttgat cagagaacac cgtgatgcca aaaaaattcc gttgaacatt    6600
gaacattggg ttatgttaca aatggccccc gattatgaga atttgactct tttacaaaaa    6660
attgaagtat tcacgtacgc tttagataat acaaaaggcc aagacctta taaaatatta    6720 tggttaaaga gtaggtcgtc agagacatgg ctagaacgta gaacaactta tacgagatct    6780
ttagcagtta tgtccatgac tggttatatt ctgggactag gtgatcgcca tccaagcaac    6840
ctgatgctag atagaatcac cggtaaagtt atccacattg atttcggcga ttgttttgaa    6900
gctgccatct aagagaaaaa gtatccagaa aaagtgccat ttagactaac taggatgtta    6960
acatacgcaa tggaagttag tggaattgaa ggcagtttcc gaattacttg tgaaaatgtc    7020
atgagagtct taagagataa taaagaatca ttaatggcga tcttggaagc ttttgcgctt    7080
gatcctttga tccattgggg atttgattta ccgccacaaa aacttactga gcaaactgga    7140
attcctttgc cgttgattaa tcctagtgaa ttattaagga aggggcaat tactgtcgaa    7200 gaagcggcaa atatggaagc agaacaacaa aatgagacca aaaacgccag agcaatgctt    7260
gttttgagac gtattacaga taaattaacg ggcaatgata tcaagaggtt caatgaatta    7320
gacgtccctg agcaggttga taaactgatc caacaagcca cttctattga aaggttatgt    7380
caacattata ttggatggtg cccattctgg tga                                 7413
```

<210> SEQ ID NO 9
<211> LENGTH: 471
<212> TYPE: PRT
<213> ORGANISM: Saccharomyces cerevisiae

<400> SEQUENCE: 9

Met Ser Ile Cys Pro His Ile Gln Gln Val Phe Gln Asn Glu Lys Ser
1               5                   10                  15

Lys Asp Gly Val Leu Lys Thr Cys Asn Ala Ala Arg Tyr Ile Leu Asn
            20                  25                  30

```
His Ser Val Pro Lys Glu Lys Phe Leu Asn Thr Met Lys Cys Gly Thr
        35                  40                  45

Cys His Glu Ile Asn Ser Gly Ala Thr Phe Met Cys Leu Gln Cys Gly
    50                  55                  60

Phe Cys Gly Cys Trp Asn His Ser His Phe Leu Ser His Ser Lys Gln
 65                  70                  75                  80

Ile Gly His Ile Phe Gly Ile Asn Ser Asn Asn Gly Leu Leu Phe Cys
                85                  90                  95

Phe Lys Cys Glu Asp Tyr Ile Gly Asn Ile Asp Leu Ile Asn Asp Ala
            100                 105                 110

Ile Leu Ala Lys Tyr Trp Asp Asp Val Cys Thr Lys Thr Met Val Pro
        115                 120                 125

Ser Met Glu Arg Arg Asp Gly Leu Ser Gly Leu Ile Asn Met Gly Ser
    130                 135                 140

Thr Cys Phe Met Ser Ser Ile Leu Gln Cys Leu Ile His Asn Pro Tyr
145                 150                 155                 160

Phe Ile Arg His Ser Met Ser Gln Ile His Ser Asn Asn Cys Lys Val
                165                 170                 175

Arg Ser Pro Asp Lys Cys Phe Ser Cys Ala Leu Asp Lys Ile Val His
            180                 185                 190

Glu Leu Tyr Gly Ala Leu Asn Thr Lys Gln Ala Ser Ser Ser Ser Thr
        195                 200                 205

Ser Thr Asn Arg Gln Thr Gly Phe Ile Tyr Leu Leu Thr Cys Ala Trp
    210                 215                 220

Lys Ile Asn Gln Asn Leu Ala Gly Tyr Ser Gln Asp Ala His Glu
225                 230                 235                 240

Phe Trp Gln Phe Ile Ile Asn Gln Ile His Gln Ser Tyr Val Leu Asp
                245                 250                 255

Leu Pro Asn Ala Lys Glu Val Ser Arg Ala Asn Asn Lys Gln Cys Glu
            260                 265                 270

Cys Ile Val His Thr Val Phe Glu Gly Ser Leu Glu Ser Ser Ile Val
        275                 280                 285

Cys Pro Gly Cys Gln Asn Asn Ser Lys Thr Thr Ile Asp Pro Phe Leu
    290                 295                 300

Asp Leu Ser Leu Asp Ile Lys Asp Lys Lys Leu Tyr Glu Cys Leu
305                 310                 315                 320

Asp Ser Phe His Lys Lys Glu Gln Leu Lys Asp Phe Asn Tyr His Cys
                325                 330                 335

Gly Glu Cys Asn Ser Thr Gln Asp Ala Ile Lys Gln Leu Gly Ile His
            340                 345                 350

Lys Leu Pro Ser Val Leu Val Leu Gln Leu Lys Arg Phe Glu His Leu
        355                 360                 365

Leu Asn Gly Ser Asn Arg Lys Leu Asp Asp Phe Ile Glu Phe Pro Thr
    370                 375                 380

Tyr Leu Asn Met Lys Asn Tyr Cys Ser Thr Lys Glu Lys Asp Lys His
385                 390                 395                 400

Ser Glu Asn Gly Lys Val Pro Asp Ile Ile Tyr Glu Leu Ile Gly Ile
                405                 410                 415

Val Ser His Lys Gly Thr Val Asn Glu Gly His Tyr Ile Ala Phe Cys
            420                 425                 430

Lys Ile Ser Gly Gly Gln Trp Phe Lys Phe Asn Asp Ser Met Val Ser
        435                 440                 445

Ser Ile Ser Gln Glu Glu Val Leu Lys Glu Gln Ala Tyr Leu Leu Phe
    450                 455                 460
```

Tyr Thr Ile Arg Gln Val Asn
465                 470

<210> SEQ ID NO 10
<211> LENGTH: 1416
<212> TYPE: DNA
<213> ORGANISM: Saccharomyces cerevisiae

<400> SEQUENCE: 10

```
atgagcattt gtccacatat acagcaagta tttcagaatg aaaagtctaa agatggggtt      60
ctaaaaacgt gcaatgctgc caggtatata ttaaatcatt ccgtacccaa ggaaaaattc     120
ttaaacacca tgaaatgtgg tacatgccac gaaataaact ctggtgcaac tttcatgtgt     180
ctacaatgtg gattttgtgg atgttggaac cattcgcatt ttctctctca cagtaaacag     240
attggtcaca tatttggtat caactcaaat aatggccttt tattttgctt caaatgtgag     300
gactatatag ggaatatcga tctgattaac gatgctatcc tagcgaagta ttgggacgac     360
gtgtgcacaa agaccatggt tcctagcatg gaaagaagag atgggctttc tggcctgatc     420
aacatgggat ccacttgttt catgagtagt attctccaat gtctaatcca taccccttac     480
tttattaggc actcaatgag tcaaattcat tctaataatt gtaaagtgcg ttctccagat     540
aaatgttttt catgtgcact cgataaaatt gttcatgaac tttatggagc gctgaataca     600
aagcaagctt cttcgtcatc tacatctact aatcggcaaa ccggattcat atatctttta     660
acttgtgcct ggaaaatcaa tcaaaatcta gcagggtatt cacaacaaga tgctcatgaa     720
ttttggcagt ttataattaa ccaaatccac caaagctatg ttcttgattt gccaaatgcc     780
aaggaagtca gcagagcaaa taataagcag tgtgaatgca tagtgcatac tgtgtttgag     840
ggctccttgg aaagttctat tgtgtgtcca ggctgtcaaa taattcaaa gacaaccatt      900
gatccattct tggatctttc tctggatatc aaggataaga aaaaacttta tgaatgtctt     960
gacagttttcc ataaaaaga acagttgaag gatttcaact atcattgtgg ggagtgtaac    1020
agcactcaag atgcaataaa gcaactaggc atacacaaat taccatcggt tttggttttg    1080
caattgaaaa gattcgaaca cctacttaat ggaagtaaca gaaaactaga cgattttatt    1140
gaatttccaa cttatttaaa tatgaaaaat tactgttcaa cgaaggaaaa agataagcat    1200
tctgaaaatg gcaaggttcc agacattatt acgaattaa tcggtattgt ttcccacaag    1260
gggacggtta tgagggaca ttatattgca ttttgtaaaa tttctggagg gcaatggttt    1320
aaattcaatg attccatggt ctcctctata tctcaagaag aggttttaaa ggaacaggca    1380
tatttattat tctacaccat tcgtcaagta aattga                              1416
```

<210> SEQ ID NO 11
<211> LENGTH: 1332
<212> TYPE: PRT
<213> ORGANISM: Saccharomyces cerevisiae

<400> SEQUENCE: 11

Met Thr Glu Arg Ile Pro Ile Lys Asn Tyr Gln Arg Thr Asn Ala Lys
1               5                   10                  15

Ala Leu Leu Lys Leu Thr Glu Lys Leu Phe Asn Lys Asn Phe Phe Asp
            20                  25                  30

Leu Tyr Leu Thr Ser Gln Gln Leu Val Val Leu Glu Tyr Leu Leu Ser
        35                  40                  45

Ile Ser Ser Glu Glu Asp Lys Leu Lys Ala Trp Asp Tyr Phe Leu Lys
    50                  55                  60

```
Gly Asn Ile Ala Leu Asn Val Glu Lys Ser Phe Pro Leu Thr Gln Glu
 65                  70                  75                  80

Glu Glu His His Gly Ala Val Ser Pro Ala Val Asp Thr Arg Ser Asp
                 85                  90                  95

Asp Val Ser Ser Gln Thr Ile Lys Asp Asn Asn Thr Asn Thr Asn
            100                 105                 110

Thr Ser Ile Ser Asn Glu Asn His Val Glu Asn Glu Ile Glu Asp Lys
        115                 120                 125

Gly Asp Asn Ala Ile Ala Asn Glu Asp Asn Phe Val Asn Asn Asp Glu
    130                 135                 140

Ser Asp Asn Val Glu Glu Asp Leu Phe Lys Leu Asp Leu Glu Asp Leu
145                 150                 155                 160

Lys Gln Gln Ile Ser Gly Thr Arg Phe Ile Gly Asn Leu Ser Leu Lys
                165                 170                 175

Ile Arg Tyr Val Leu Trp Gln Cys Ala Ile Asp Tyr Ile Tyr Cys Asp
            180                 185                 190

Arg Asn Glu Phe Gly Asp Glu Asn Asp Thr Glu Tyr Thr Leu Leu Asp
        195                 200                 205

Val Glu Glu Lys Glu Glu Glu Ile Gly Lys Asn Glu Lys Pro Gln
    210                 215                 220

Asn Lys Glu Gly Ile Ser Lys Phe Ala Glu Asp Glu Tyr Asp Asp
225                 230                 235                 240

Glu Asp Glu Asn Tyr Asp Glu Asp Ser Thr Asp Val Lys Asn Val Asp
                245                 250                 255

Asp Pro Pro Lys Asn Leu Asp Ser Ile Ser Ser Asn Ile Glu Ile
            260                 265                 270

Asp Asp Glu Arg Arg Leu Val Leu Asn Ile Ser Ile Ser Lys Glu Thr
        275                 280                 285

Leu Ser Lys Leu Lys Thr Asn Asn Val Glu Glu Ile Met Gly Asn Trp
    290                 295                 300

Asn Lys Ile Tyr His Ser Phe Glu Tyr Asp Lys Glu Thr Met Ile Lys
305                 310                 315                 320

Arg Leu Lys Leu Glu Glu Ser Asp Lys Met Ile Glu Lys Gly Lys Lys
                325                 330                 335

Lys Arg Ser Arg Ser Asp Leu Glu Ala Ala Thr Asp Glu Gln Asp Arg
            340                 345                 350

Glu Asn Thr Asn Asp Glu Pro Asp Thr Asn Gln Lys Leu Pro Thr Pro
        355                 360                 365

Glu Gly Ser Thr Phe Ser Asp Thr Gly Asn Lys Arg Pro Lys Gln Ser
    370                 375                 380

Asn Leu Asp Leu Thr Val Asn Leu Gly Ile Glu Asn Leu Ser Leu Lys
385                 390                 395                 400

His Leu Leu Ser Ser Ile Gln Gln Lys Lys Ser Gln Leu Gly Ile Ser
                405                 410                 415

Asp Tyr Glu Leu Lys His Leu Ile Met Asp Val Arg Lys Asn Arg Ser
            420                 425                 430

Lys Trp Thr Ser Asp Glu Arg Ile Gly Gln Glu Leu Tyr Glu Ala
        435                 440                 445

Cys Glu Lys Val Val Leu Glu Leu Arg Asn Tyr Thr Glu His Ser Thr
    450                 455                 460

Pro Phe Leu Asn Lys Val Ser Lys Arg Glu Ala Pro Asn Tyr His Gln
465                 470                 475                 480

Ile Ile Lys Lys Ser Met Asp Leu Asn Thr Val Leu Lys Lys Leu Lys
                485                 490                 495
```

```
Ser Phe Gln Tyr Asp Ser Lys Gln Glu Phe Val Asp Asp Ile Met Leu
            500                 505                 510

Ile Trp Lys Asn Cys Leu Thr Tyr Asn Ser Asp Pro Ser His Phe Leu
        515                 520                 525

Arg Gly His Ala Ile Ala Met Gln Lys Lys Ser Leu Gln Leu Ile Arg
    530                 535                 540

Met Ile Pro Asn Ile Thr Ile Arg Asn Arg Ala Asp Leu Glu Lys Glu
545                 550                 555                 560

Ile Glu Asp Met Glu Lys Asp Lys Asp Tyr Glu Leu Asp Glu Glu Glu
                565                 570                 575

Glu Val Ala Gly Ser Gly Arg Lys Gly Leu Asn Met Gly Ala His Met
            580                 585                 590

Leu Ala Lys Glu Asn Gly Lys Val Ser Glu Lys Asp Ser Ser Lys Thr
        595                 600                 605

Val Lys Asp Glu Ala Pro Thr Asn Asp Asp Lys Leu Thr Ser Val Ile
    610                 615                 620

Pro Glu Gly Glu Lys Glu Lys Asp Lys Thr Ala Ser Ser Thr Val Thr
625                 630                 635                 640

Val His Glu Asn Val Asn Lys Asn Glu Ile Lys Glu Asn Gly Lys Asn
                645                 650                 655

Glu Glu Gln Asp Met Val Glu Glu Ser Ser Lys Thr Glu Asp Ser Ser
            660                 665                 670

Lys Asp Ala Asp Ala Ala Lys Lys Asp Thr Glu Asp Gly Leu Gln Asp
        675                 680                 685

Lys Thr Ala Glu Asn Lys Glu Ala Gly Glu Asn Asn Glu Glu Glu Glu
    690                 695                 700

Asp Asp Asp Asp Glu Asp Glu Asp Met Val Asp Ser Gln Ser
705                 710                 715                 720

Tyr Leu Leu Glu Lys Asp Asp Asp Arg Asp Leu Glu Ile Ser Val
                725                 730                 735

Trp Lys Thr Val Thr Ala Lys Val Arg Ala Glu Ile Cys Leu Lys Arg
            740                 745                 750

Thr Glu Tyr Phe Lys Asn Gly Lys Leu Asn Ser Asp Ser Glu Ala Phe
        755                 760                 765

Leu Lys Asn Pro Gln Arg Met Lys Arg Phe Asp Gln Leu Phe Leu Glu
    770                 775                 780

Tyr Lys Glu Gln Lys Ala Leu Glu Ser Tyr Arg Gln Lys Ile Glu Gln
785                 790                 795                 800

Asn Ser Ile Met Lys Asn Gly Phe Gly Thr Val Leu Lys Gln Glu Asp
                805                 810                 815

Asp Asp Gln Leu Gln Phe His Asn Asp His Ser Leu Asn Gly Asn Glu
            820                 825                 830

Ala Phe Glu Lys Gln Pro Asn Asp Ile Glu Leu Asp Asp Thr Arg Phe
        835                 840                 845

Leu Gln Glu Tyr Asp Ile Ser Asn Ala Ile Pro Asp Ile Val Tyr Glu
    850                 855                 860

Gly Val Asn Thr Lys Thr Leu Asp Lys Met Glu Asp Ala Ser Val Asp
865                 870                 875                 880

Arg Met Leu Gln Asn Gly Ile Asn Lys Gln Ser Arg Phe Leu Ala Asn
                885                 890                 895

Lys Asp Leu Gly Leu Thr Pro Lys Met Asn Gln Asn Ile Thr Leu Ile
            900                 905                 910

Gln Gln Ile Arg His Ile Cys His Lys Ile Ser Leu Ile Arg Met Leu
```

-continued

```
                915                 920                 925
Gln Ser Pro Leu Ser Ala Gln Asn Ser Arg Ser Asn Pro Asn Ala Phe
    930                 935                 940
Leu Asn Asn His Ile Tyr Asn Tyr Thr Ile Ile Asp Asp Ser Leu Asp
945                 950                 955                 960
Ile Asp Pro Val Ser Gln Leu Pro Thr His Asp Tyr Lys Asn Asn Arg
                965                 970                 975
Glu Leu Ile Trp Lys Phe Met His Lys Asn Ile Ser Lys Val Ala Met
                    980                 985                 990
Ala Asn Gly Phe Glu Thr Ala His Pro Ser Ala Ile Asn Met Leu Thr
                995                 1000                1005
Glu Ile Ala Gly Asp Tyr Leu Ser Asn Leu Ile Lys Thr Leu Lys
    1010                1015                1020
Leu His His Glu Thr Asn Ser Leu Asn Arg Gly Thr Asn Val Glu
    1025                1030                1035
Met Leu Gln Thr Thr Leu Leu Glu Asn Gly Ile Asn Arg Pro Asp
    1040                1045                1050
Asp Leu Phe Ser Tyr Val Glu Ser Glu Phe Gly Lys Lys Thr Lys
    1055                1060                1065
Lys Leu Gln Asp Ile Lys Gln Lys Leu Glu Ser Phe Leu Arg Ala
    1070                1075                1080
Leu Leu Arg Pro Thr Leu Gln Glu Leu Ser Glu Arg Asn Phe Glu
    1085                1090                1095
Asp Glu Ser Gln Ser Phe Phe Thr Gly Asp Phe Ala Ser Glu Leu
    1100                1105                1110
Thr Gly Glu Asp Phe Phe Gly Phe Arg Glu Leu Gly Leu Glu Lys
    1115                1120                1125
Glu Phe Gly Val Leu Ser Ser Val Pro Leu Gln Leu Leu Thr
    1130                1135                1140
Thr Gln Phe Gln Thr Val Asp Gly Glu Thr Lys Val Gln Ala Lys
    1145                1150                1155
Lys Ile Gln Pro Glu Glu Ser Asp Ser Ile Val Tyr Lys Lys Ile
    1160                1165                1170
Thr Lys Gly Met Leu Asp Ala Gly Ser Phe Trp Asn Thr Leu Leu
    1175                1180                1185
Pro Leu Leu Gln Lys Asp Tyr Glu Arg Ser Lys Ala Tyr Ile Ala
    1190                1195                1200
Lys Gln Ser Lys Ser Ser Ala Asn Asp Lys Thr Ser Met Thr Ser
    1205                1210                1215
Thr Glu Asp Asn Ser Phe Ala Leu Leu Glu Glu Asp Gln Phe Val
    1220                1225                1230
Ser Lys Lys Thr Ala Thr Lys Ala Arg Leu Pro Pro Thr Gly Lys
    1235                1240                1245
Ile Ser Thr Thr Tyr Lys Lys Lys Pro Ile Ala Ser Ala Phe Ile
    1250                1255                1260
Leu Pro Glu Glu Asp Leu Glu Asn Asp Val Lys Ala Asp Pro Thr
    1265                1270                1275
Thr Thr Val Asn Ala Lys Val Gly Ala Glu Asn Asp Gly Asp Ser
    1280                1285                1290
Ser Leu Phe Leu Arg Thr Pro Gln Pro Leu Asp Pro Leu Asp Met
    1295                1300                1305
Asp Asp Ala Phe Asp Asp Thr Asn Met Gly Ser Asn Ser Ser Phe
    1310                1315                1320
```

Ser Leu  Ser Leu  Pro Arg Leu  Asn Gln
    1325              1330

<210> SEQ ID NO 12
<211> LENGTH: 3999
<212> TYPE: DNA
<213> ORGANISM: Saccharomyces cerevisiae

<400> SEQUENCE: 12

| | | | | | |
|---|---|---|---|---|---|
| atgactgaaa | gaataccaat | aaagaattat | caaagaacaa | atgccaaagc | tttacttaaa | 60 |
| ttgactgaaa | aacttttttaa | caagaacttt | tttgatctct | atttaacctc | tcagcaattg | 120 |
| gtcgttcttg | aatacctgct | gtcgatttca | agtgaagaag | acaaactgaa | agcatgggac | 180 |
| tatttcttaa | agggaaacat | agcattaaat | gtcgaaaaat | catttccatt | aacccaagaa | 240 |
| gaagaacatc | acggagcggt | ctctcctgcc | gttgacacac | gatcagatga | tgtatcatca | 300 |
| caaacaatta | aggacaataa | caatactaat | accaacacca | gtatcagcaa | tgaaaatcat | 360 |
| gttgaaaatg | aaattgaaga | taaaggcgat | aacgcaaatg | caaatgaaga | taattttgtg | 420 |
| aataatgacg | aaagtgataa | tgttgaagaa | gacttattca | aattagatct | agaggacttg | 480 |
| aagcagcaaa | taagcggaac | aaggtttatt | ggaaacttat | ccttgaaaat | cagatacgtc | 540 |
| ttgtggcagt | gcgccataga | ttatatatac | tgtgatcgta | atgagtttgg | tgatgaaaat | 600 |
| gatacagaat | acaccctatt | agatgttgaa | gagaaggagg | aagaggaaat | tggtaaaaat | 660 |
| gagaagccac | aaaacaaaga | aggtatttcg | aagttcgccg | aggatgaaga | ttacgacgat | 720 |
| gaagacgaga | actatgatga | agacagtaca | gacgtaaaaa | atgtcgatga | tcctccaaaa | 780 |
| aatctcgatt | ctatttcctc | ttctaatatc | gaaattgacg | atgaacgacg | cttggtgcta | 840 |
| aatatctcaa | tatcaaaaga | aacactgtca | agttaaaaaa | caataatgt | agaagaaatt | 900 |
| atgggaaatt | ggaacaaaat | ttaccacagt | tttgaatacg | ataaagaaac | tatgataaag | 960 |
| cgattaaaac | ttgaagaaag | cgataaaatg | atagagaaag | gaagaagaa | acgaagtcga | 1020 |
| agtgatttag | aagcagctac | cgatgaacaa | gatcgcgaaa | atacaaatga | tgagccagat | 1080 |
| actaatcaaa | aattgcccac | tcctgaaggt | tcaacattca | gcgatactgg | gaacaagcgc | 1140 |
| cccaaacaaa | gtaatttaga | tttaacagtc | aatctaggca | tcgaaaattt | atcattaaag | 1200 |
| caccttctat | catctatcca | gcaaaaaaaa | tcccaattag | gaatatcaga | ttacgaatta | 1260 |
| aaacatctga | ttatggatgt | cagaaaaaat | cggtcaaaat | ggacatcgga | tgaaagaatt | 1320 |
| gggcaagagg | aattatacga | agcctgtgaa | aaggttgttt | tggaacttag | aaactacact | 1380 |
| gagcattcta | caccatttct | gaataaagtg | agcaaaagag | aagcccccaa | ttatcatcaa | 1440 |
| atcatcaaaa | agtccatgga | cctgaatact | gttttaaaaa | aactgaaaag | ctttcaatat | 1500 |
| gactccaaac | aagaatttgt | agacgatatt | atgctaatat | ggaaaaattg | tttgacctat | 1560 |
| aattcagatc | cttcacattt | tttgagaggg | catgctattg | ctatgcagaa | gaaatctctt | 1620 |
| cagttgattc | gcatgattcc | aaaatatcaca | atccgaaaca | gggctgattt | agaaaaggaa | 1680 |
| attgaagata | tggaaaaaga | caaagactac | gaattagatg | aggaagagga | agttgctggt | 1740 |
| tctggaagaa | aaggattgaa | tatgggagct | catatgttgg | ccaaagagaa | tggcaaggtg | 1800 |
| tcagaaaaag | atagctctaa | aaccgtcaag | gatgaagcac | caaccaatga | tgacaaacta | 1860 |
| acttctgtca | tccctgaggg | ggaaaaagag | aaagataaaa | ctgcttcatc | tactgtaacg | 1920 |
| gtacacgaaa | atgtaaataa | gaacgaaata | aagaaaatg | ggaaaatga | agagcaagat | 1980 |
| atggttgagg | aaagtagtaa | gactgaggat | tcatcaaaag | atgctgatgc | tgccaaaaag | 2040 |
| gatacggaag | acggactaca | agataaaact | gcagaaaata | aggaggctgg | ggaaaataat | 2100 |

```
gaagaggaag aggatgatga tgacgaagat gaagacgaag acatggtcga ctcccaatct   2160
tatttacttg aaaaggatga cgatagagac gatttggaaa tatccgtgtg aaaactgta    2220 actgccaaag ttcgtgcgga aatttgctta aaagaactg aatattttaa aaatggaaaa   2280
ttaaatagtg attcagaggc gttttgaaa acccacaaa gaatgaaaag gttcgaccag    2340 cttttcttg aatataaga gcagaaagct ttagaatcat atcgtcaaaa aatagagcaa    2400
aattccatta tgaaaatgg ctttggaaca gtactaaaac aggaagacga tgaccaattg    2460
cagtttcata tgatcactc tttaaatgga atgaagctt ttgaaaagca acccaatgat    2520
attgagttag atgataccag attcctacag gaatatgata ttagtaacgc cattcctgac   2580
atagtatacg agggagtaaa tactaaaaca ttagacaaga tggaagacgc ttccgtggac   2640
cgcatgcttc aaaatggtat caacaaacaa agcagatttc tggctaacaa ggatttagga   2700
ctaacaccta aaatgaacca aaatatcaca ctgattcagc aaattaggca catatgccat   2760
aaaatatccc tgatcagaat gttacagagc ccttatcgg ctcaaaactc cagaagcaat   2820
cccaacgctt tccttaacaa ccacatttat aattcacta ttattgatga ctcactcgat    2880
attgatccgg tgtcacagct tccaacgcat gattacaaaa caacaggga gctgatatgg    2940 aaattcatgc ataagaacat atctaaggtt gctatggcca atgggtttga aactgcccat    3000
ccatcagcaa taaacatgct tactgaaatc gccgggatt acctatctaa tctgataaag    3060
actttgaagc ttcatcatga aactaactcc ttaaatagag gaacaaatgt ggaaatgctg    3120
caaacaacac tgttggaaaa cggtatcaac aggccagacg atctattttc ctatgttgaa    3180
tctgaatttg gtaaaaaaac taagaaactt caggacatca aacagaaact agaaagcttt    3240
ttgagagcct tattaaggcc aactttgcag gagttgtccg agagaaactt tgaagacgag    3300
agccaaagct tttttacagg tgactttgcc agcgaattga ctggtgaaga cttctttggt    3360
tttagagagc ttggattaga aaaggagttt ggagttttga gttcatctgt tccattacag    3420
ttactgacta ctcagtttca aactgttgac ggggaaacca aagtgcaggc caaaaagatc    3480
caaccggaag aatcagacag cattgtgtat aagaaaatta caaaaggtat gctggatgct    3540
ggttcattct ggaatactct acttccccta ttacaaaaag attatgaacg ttccaaggcc    3600
tatatagcaa agcaaagcaa gtcatctgca aatgataaaa cctcaatgac ttccacagaa    3660
gacaattctt tcgctttact agaagaggat cagtttgtct caaagaaaac cgcaacgaag    3720
gcaagattac ctcctactgg taagataagt accacataca aaagaaacc gatcgcaagc    3780 gcgtttatac ttccagaaga agacttggaa aacgacgtaa aagcggatcc aacaacaact    3840
gtaaacgcca aagtgggtgc agaaaatgat ggagattctt ccttatttt gcgaacgcct    3900 caaccttag atcctttgga tatggatgat gcttttgatg ataccaatat gggcagcaat    3960
agttcattta gcttgagcct tcctcgcctt aatcaataa                          3999
```

<210> SEQ ID NO 13
<211> LENGTH: 602
<212> TYPE: PRT
<213> ORGANISM: Saccharomyces cerevisiae

<400> SEQUENCE: 13

```
Met Asp Glu Val Asp Asp Ile Leu Ile Asn Asn Gln Val Val Asp Asp
1               5                   10                  15

Glu Glu Asp Asp Glu Glu Met Leu Ser Gly Leu Glu Asn Asp Ser Lys
            20                  25                  30

Gln Asp Leu Glu Gly Asn Asp Asp Gly Gly Glu Asp Glu Glu Asp Asp
```

```
                    35                  40                  45
Asp Asp Asp Asp Glu Asp Asp Asp Glu Asp Glu Arg Glu Asp
 50                  55                  60
Asp Asp Glu Gln Glu Asp Asp Gly Glu Asp Asp Ala Ala Arg Met
 65                  70                  75                  80
Asp Lys Thr Ala Thr Pro Thr Asn Glu His Gln His Asp Glu Gln Lys
                 85                  90                  95
Ala Ala Ala Ala Gly Ala Gly Gly Ala Gly Asp Ser Gly Asp Ala Val
                100                 105                 110
Thr Lys Ile Gly Ser Glu Asp Val Lys Leu Ser Asp Val Asp Gly Gly
                115                 120                 125
Val Gly Ser Arg Glu Ala Ser Ser Thr His Glu Ala Ser Ala Asn
130                 135                 140
Gly Glu Val Tyr Glu Tyr Tyr Lys His Met Leu Asn Ala Ala Gln Ile
145                 150                 155                 160
Ala Asp Ser Tyr Asn Ile Tyr Pro Thr Ala Ala Ile Pro Ile Gln Thr
                165                 170                 175
His Val Asn Ala Leu Ala Val Ser Arg Gly Leu Lys Tyr Leu Phe Leu
                180                 185                 190
Gly Gly Ser Asp Gly Tyr Ile Arg Lys Tyr Asp Leu Leu Asn Thr Leu
                195                 200                 205
Glu Gly Lys Leu Ser Leu Thr Ile Leu Gln Lys His Ser Leu Ala Glu
                210                 215                 220
Ser Ile Gln Asn Ala Gly Ile Leu Gln Ser Tyr Trp Glu Asn Glu Ile
225                 230                 235                 240
Pro Gln Lys Lys Ser Glu Met Lys Leu Ser Ala Asn Lys Thr Asp Tyr
                245                 250                 255
Glu Pro Lys Val Ser Pro Val His Ser Leu Glu Val Gln Ser Glu Cys
                260                 265                 270
Leu Phe Ile Leu Ser Gly Leu Gln Asn Gly Gly Ile Thr Met Gln Gly
                275                 280                 285
Val Arg Tyr Met Glu Gly Ser Ile Ala His Tyr Phe Lys Gly Arg Asn
                290                 295                 300
Gly His Thr Gln Ile Val Asn Ile Leu Arg Leu Asn Gly Gln Glu Asp
305                 310                 315                 320
Arg Phe Leu Ser Gly Ser Trp Asp Lys Arg Leu Leu Glu Trp Asp Leu
                325                 330                 335
Gln Thr Gly Asp Ile Val Asn Glu Phe Lys Lys Ser Arg Ser Glu Leu
                340                 345                 350
Ser Ser Leu Glu Met Arg Pro Leu Tyr Ser Ser Val Asp Val Ser Gly
                355                 360                 365
Asn Val Asn Ser Gly Lys Glu Asn Glu Asn Ala Asp Asp Asp Met Asp
                370                 375                 380
Ser Leu Phe Gly Asp Glu Asp Glu Asp Lys Gln Asp Ala Gly Asn
385                 390                 395                 400
Glu Pro Val Glu Thr Gly Asp Gly Ser Asn Gly Glu Glu Asn Lys Glu
                405                 410                 415
Gln Ile Ser Glu Glu Ser Leu Asn Ile Val Tyr Asp Glu Ser Val Phe
                420                 425                 430
Met Thr Ser Gly Leu Asn Gly Ser Val His Ile Trp Asp Arg Arg Met
                435                 440                 445
Thr Gln Ser Pro Ala Leu Ser Leu Glu Arg Gly Ala Gly Val Pro Pro
450                 455                 460
```

|  |  |  |  |  |  |  |  |  |  |  |  |
|---|---|---|---|---|---|---|---|---|---|---|---|
| Trp | Cys | Leu | Ser | Ala | Cys | Trp | Gly | Val | Asp | Gly | Asp | His | Val | Tyr | Ala |
| 465 |  |  |  | 470 |  |  |  |  | 475 |  |  |  |  | 480 |  |

Trp Cys Leu Ser Ala Cys Trp Gly Val Asp Gly Asp His Val Tyr Ala
465                 470                 475                 480

Gly Arg Arg Asn Ala Cys Val Glu Gln Phe Asp Leu Lys Met Pro Ser
                485                 490                 495

Lys Pro Ile His Asn Leu Lys Leu Pro Ser Ile Ser Gly Pro Val Ser
            500                 505                 510

Cys Val Lys Ala Met Pro Asn Asn Lys His Leu Leu Cys Ala Ser Arg
        515                 520                 525

Asp Asn Ile Arg Leu Tyr Asn Val Glu Ile Ala Val Asp Ala Ser Asn
    530                 535                 540

Ser Thr Thr Lys Ser Ser Lys Val Pro Phe Leu Ile Val Pro Gly His
545                 550                 555                 560

His Gly Gly Ile Ile Ser Asn Leu Tyr Leu Asp Pro Thr Ser Arg Phe
                565                 570                 575

Ile Ile Ser Thr Ser Gly Asn Arg Gly Trp Gln Gly Asn Ser Thr Asp
            580                 585                 590

Thr Thr Leu Ile Tyr Asp Ile Asp Leu Glu
        595                 600

<210> SEQ ID NO 14
<211> LENGTH: 1809
<212> TYPE: DNA
<213> ORGANISM: Saccharomyces cerevisiae

<400> SEQUENCE: 14

| | | | | |
|---|---|---|---|---|
| atggacgagg | ttgacgatat | tctaattaac | aaccaggtgg | tggatgacga | ggaggatgac | 60 |
| gaagagatgc | tgagtgggct | ggaaaacgac | tcaaagcagg | acctcgaggg | gaatgatgac | 120 |
| ggtggtgaag | atgaagagga | tgacgatgat | gatgatgagg | acgatgatga | tgacgaggac | 180 |
| gaacgagagg | acgacgatga | acaggaggac | gacgatggtg | aggacgacgc | cgcaagaatg | 240 |
| gataagactg | ctacaccgac | gaatgagcac | cagcatgatg | agcaaaaggc | tgctgctgct | 300 |
| ggtgctggcg | gtgcaggcga | tagtggcgat | gctgttacta | agattggatc | cgaggatgtg | 360 |
| aaattgagcg | atgttgatgg | aggagtgggg | tccaggaag | catcttcctc | tacacacgaa | 420 |
| gcctctgcta | atggagaggt | ttatgagtac | tataagcaca | tgttgaatgc | cgcacagatt | 480 |
| gcggattcgt | acaatatcta | ccccacggca | gccataccca | tccagacgca | cgtcaatgcg | 540 |
| ttggccgtgt | ccagggggtct | caagtacctg | tttttgggcg | gtagcgatgg | atacataagg | 600 |
| aagtacgact | tgctgaacac | gcttgagggg | aaactttctc | taactatcct | gcagaagcat | 660 |
| tcgttggctg | agtctattca | gaacgcgggt | atcttgcagt | cgtactggga | aaatgagatc | 720 |
| ccgcagaaaa | aatcagaaat | gaaactctcc | gctaataaga | cagattacga | gcccaaagtt | 780 |
| agccccgttc | attctttgga | agtccaaagc | gaatgcctct | ttatactgag | cgggctacag | 840 |
| aatggtggga | ttaccatgca | gggcgttcgc | tacatggagg | ggagcattgc | gcactatttt | 900 |
| aagggcagga | atgacatac | ccaaatcgtt | aacatactga | gattaaacgg | tcaagaggac | 960 |
| aggttttttga | gtggttcctg | ggataagcgt | cttttggaat | gggatttgca | gacgggtgac | 1020 |
| atagttaatg | agtttaaaaa | atcaaggtct | gaattgtcat | ctttggaaat | gcggccgctg | 1080 |
| tactcgtccg | tggatgtgtc | cggtaacgtc | aacagtggta | agagaatga | aaatgcagat | 1140 |
| gacgatatgg | attctctgtt | tggtgatgaa | gacgaagacg | aaaagcaaga | tgctggcaac | 1200 |
| gaacccgtcg | agacggggga | tggttctaat | ggtgaagaga | acaaagaaca | gatatctgaa | 1260 |
| gaatctttga | acatagtcta | tgatgaatcc | gttttatga | cctcagggtt | gaacggttcc | 1320 |
| gtgcatattt | gggaccgacg | catgacgcag | tcgccagcat | tgtctctgga | gagaggtgca | 1380 |

```
ggcgtcccac cgtggtgttt gtccgcatgt tggggtgtag atggtgatca tgtgtatgca   1440
gggagaagga atgcctgtgt ggagcagttt gacttgaaga tgccctcgaa acctatccat   1500
aatttgaaac tgccttctat ttcagggcct gtctcttgtg ttaaagccat gcctaataac   1560
aagcatttac tatgtgcatc gcgggataat atcagattgt acaacgttga aattgcagta   1620
gatgcttcga attcgactac aaagagttct aaagtgccgt tcctcatcgt gccgggccat   1680
cacggtggta ttatatcaaa cttatacctc gaccccactt caagatttat aataagcaca   1740
agtggcaaca gaggctggca ggggaattct acggacacga cccttattta cgatatagac   1800
ttagaatag                                                           1809
```

<210> SEQ ID NO 15
<211> LENGTH: 633
<212> TYPE: PRT
<213> ORGANISM: Saccharomyces cerevisiae

<400> SEQUENCE: 15

```
Met Ser Ser Asn Asn Thr Asn Thr Ala Pro Ala Asn Ala Asn Ser
1               5                   10                  15

Ser His His His His His His His His His His Gly His
                20                  25                  30

Gly Gly Ser Asn Ser Thr Leu Asn Asn Pro Lys Ser Ser Leu Ala Asp
            35                  40                  45

Gly Ala His Ile Gly Asn Tyr Gln Ile Val Lys Thr Leu Gly Glu Gly
        50                  55                  60

Ser Phe Gly Lys Val Lys Leu Ala Tyr His Thr Thr Gly Gln Lys
65                  70                  75                  80

Val Ala Leu Lys Ile Ile Asn Lys Lys Val Leu Ala Lys Ser Asp Met
                85                  90                  95

Gln Gly Arg Ile Glu Arg Glu Ile Ser Tyr Leu Arg Leu Leu Arg His
            100                 105                 110

Pro His Ile Ile Lys Leu Tyr Asp Val Ile Lys Ser Lys Asp Glu Ile
        115                 120                 125

Ile Met Val Ile Glu Tyr Ala Gly Asn Glu Leu Phe Asp Tyr Ile Val
    130                 135                 140

Gln Arg Asp Lys Met Ser Glu Gln Glu Ala Arg Arg Phe Phe Gln Gln
145                 150                 155                 160

Ile Ile Ser Ala Val Glu Tyr Cys His Arg His Lys Ile Val His Arg
                165                 170                 175

Asp Leu Lys Pro Glu Asn Leu Leu Leu Asp Glu His Leu Asn Val Lys
            180                 185                 190

Ile Ala Asp Phe Gly Leu Ser Asn Ile Met Thr Asp Gly Asn Phe Leu
        195                 200                 205

Lys Thr Ser Cys Gly Ser Pro Asn Tyr Ala Ala Pro Glu Val Ile Ser
    210                 215                 220

Gly Lys Leu Tyr Ala Gly Pro Glu Val Asp Val Trp Ser Cys Gly Val
225                 230                 235                 240

Ile Leu Tyr Val Met Leu Cys Arg Arg Leu Pro Phe Asp Asp Glu Ser
                245                 250                 255

Ile Pro Val Leu Phe Lys Asn Ile Ser Asn Gly Val Tyr Thr Leu Pro
            260                 265                 270

Lys Phe Leu Ser Pro Gly Ala Ala Gly Leu Ile Lys Arg Met Leu Ile
        275                 280                 285

Val Asn Pro Leu Asn Arg Ile Ser Ile His Glu Ile Met Gln Asp Asp
```

```
                290                   295                   300
Trp Phe Lys Val Asp Leu Pro Glu Tyr Leu Leu Pro Pro Asp Leu Lys
305                 310                 315                 320

Pro His Pro Glu Glu Asn Glu Asn Asn Asp Ser Lys Lys Asp Gly
            325                 330                 335

Ser Ser Pro Asp Asn Asp Glu Ile Asp Asp Asn Leu Val Asn Ile Leu
            340                 345                 350

Ser Ser Thr Met Gly Tyr Glu Lys Asp Glu Ile Tyr Glu Ser Leu Glu
            355                 360                 365

Ser Ser Glu Asp Thr Pro Ala Phe Asn Glu Ile Arg Asp Ala Tyr Met
370                 375                 380

Leu Ile Lys Glu Asn Lys Ser Leu Ile Lys Asp Met Lys Ala Asn Lys
385                 390                 395                 400

Ser Val Ser Asp Glu Leu Asp Thr Phe Leu Ser Gln Ser Pro Pro Thr
                405                 410                 415

Phe Gln Gln Gln Ser Lys Ser His Gln Lys Ser Gln Val Asp His Glu
            420                 425                 430

Thr Ala Lys Gln His Ala Arg Arg Met Ala Ser Ala Ile Thr Gln Gln
            435                 440                 445

Arg Thr Tyr His Gln Ser Pro Phe Met Asp Gln Tyr Lys Glu Glu Asp
450                 455                 460

Ser Thr Val Ser Ile Leu Pro Thr Ser Leu Pro Gln Ile His Arg Ala
465                 470                 475                 480

Asn Met Leu Ala Gln Gly Ser Pro Ala Ala Ser Lys Ile Ser Pro Leu
                485                 490                 495

Val Thr Lys Lys Ser Lys Thr Arg Trp His Phe Gly Ile Arg Ser Arg
                500                 505                 510

Ser Tyr Pro Leu Asp Val Met Gly Glu Ile Tyr Ile Ala Leu Lys Asn
            515                 520                 525

Leu Gly Ala Glu Trp Ala Lys Pro Ser Glu Glu Asp Leu Trp Thr Ile
            530                 535                 540

Lys Leu Arg Trp Lys Tyr Asp Ile Gly Asn Lys Thr Asn Thr Asn Glu
545                 550                 555                 560

Lys Ile Pro Asp Leu Met Lys Met Val Ile Gln Leu Phe Gln Ile Glu
                565                 570                 575

Thr Asn Asn Tyr Leu Val Asp Phe Lys Phe Asp Gly Trp Glu Ser Ser
            580                 585                 590

Tyr Gly Asp Asp Thr Thr Val Ser Asn Ile Ser Glu Asp Glu Met Ser
            595                 600                 605

Thr Phe Ser Ala Tyr Pro Phe Leu His Leu Thr Thr Lys Leu Ile Met
            610                 615                 620

Glu Leu Ala Val Asn Ser Gln Ser Asn
625                 630
```

<210> SEQ ID NO 16
<211> LENGTH: 1902
<212> TYPE: DNA
<213> ORGANISM: Saccharomyces cerevisiae

<400> SEQUENCE: 16

```
atgagcagta acaacaacac aaacacagca cctgccaatg caaattctag ccaccaccac      60
caccatcacc accatcacca ccaccatcac ggtcatggcg aagcaactc gacgctaaac     120 aatcccaagt cgtccttagc ggatggtgca catatcggga actaccaaat cgtcaaaacg     180
ctgggagagg ggtccttttgg taaagttaaa ttggcatatc ataccactac gggccaaaaa     240
```

```
gttgctctaa aaatcattaa taagaaggtt ttggcaaaga gtgatatgca gggcagaatt      300
gaaagagaaa tatcttatct gagactctta agacaccccc acatcatcaa actgtatgat      360
gttatcaaat ccaaagatga aatcattatg gttatagagt acgccgggaa cgaattgttt      420
gactatattg ttcagagaga caaaatgagc gagcaagagg caagaagatt tttccagcag      480
atcatcagtg ccgtcgagta ctgccatagg acaaaattg tccatagaga tctgaagcct       540
gaaaacttac tactagatga gcatctgaat gtaaagattg ccgattttgg tttgtcaaac      600
atcatgactg atggtaattt cttaaagact tcttgtggtt ctcccaatta tgcggctcct      660
gaagttatca gcggtaagct gtacgcaggc ccagaagtgg acgtgtggtc atgtggggtt      720
atcctttatg ttatgctttg tcgtcgtcta ccgtttgacg atgaaagcat cccagtgctt      780
ttcaagaata tcagcaacgg tgtttacacc ttgcctaaat ttttatctcc tggagctgct      840
gggctaatca aaagaatgtt aatcgttaat ccattgaaca aataagcat  tcatgaaatt      900 atgcaagacg attggttcaa agttgacctg ccagaatatc tacttccacc agatttgaaa      960
ccacacccag aagaagagaa tgaaaataat gactcaaaaa aggatggcag cagcccagat     1020
aacgatgaaa ttgatgacaa ccttgtcaat attttatcat cgaccatggg ttacgaaaaa     1080
gacgagattt atgagtcctt agaatcatca gaagacactc ctgcattcaa cgaaattagg     1140
gacgcgtaca tgttgattaa ggagaataaa tctttgatca aggatatgaa ggcaaacaaa     1200
agcgtcagtg atgaactgga tacctttctg tcccagtcac ctccaacttt tcaacaacaa     1260
agcaaatccc atcaaaagag tcaagtagat catgaaactg ccaagcaaca cgcaagaagg     1320
atggcaagtg ctatcactca acaaaggaca tatcaccaat caccttcat ggatcagtat       1380 aaagaagaag actctacagt ttccatttg cctacatctt tacctcagat ccacagagct      1440
aatatgttag cacaaggttc gccagctgcc tctaaaatat ctcctcttgt aacgaaaaaa     1500
tctaaaacga gatggcattt tggtatacga tctcgctcat atccattaga cgttatgggt     1560
gaaatttata ttgccttgaa gaatttgggt gccgaatggg ccaagccatc tgaagaggat     1620
ttatggacta tcaaattaag gtggaaatat gatattggaa acaagacaaa cactaatgaa     1680
aaaatacctg atttaatgaa aatggtaatt caattatttc aaattgaaac caataattat     1740
ttggtggatt tcaaatttga cggctgggaa agtagttatg gagatgatac tactgtttct     1800
aatatttctg aagatgaaat gagtactttt tcagcctacc cattttaca  tttaacaaca     1860 aaactaatta tggaattagc cgttaacagt caaagcaatt ga                        1902
```

<210> SEQ ID NO 17
<211> LENGTH: 713
<212> TYPE: PRT
<213> ORGANISM: Saccharomyces cerevisiae

<400> SEQUENCE: 17

```
Met Ser Pro Ser Ala Val Gln Ser Ser Lys Leu Glu Glu Gln Ser Ser
1               5                   10                  15

Glu Ile Asp Lys Leu Lys Ala Lys Met Ser Gln Ser Ala Ala Thr Ala
            20                  25                  30

Gln Arg Lys Lys Glu His Glu Tyr Glu His Leu Thr Ser Val Lys Ile
        35                  40                  45

Val Pro Gln Arg Pro Ile Ser Asp Arg Leu Gln Pro Ala Ile Ala Thr
    50                  55                  60

His Tyr Ser Pro His Leu Asp Gly Leu Gln Asp Tyr Gln Arg Leu His
65                  70                  75                  80
```

```
Lys Glu Ser Ile Glu Asp Pro Ala Lys Phe Phe Gly Ser Lys Ala Thr
                85                  90                  95
Gln Phe Leu Asn Trp Ser Lys Pro Phe Asp Lys Val Phe Ile Pro Asp
            100                 105                 110
Pro Lys Thr Gly Arg Pro Ser Phe Gln Asn Asn Ala Trp Phe Leu Asn
        115                 120                 125
Gly Gln Leu Asn Ala Cys Tyr Asn Cys Val Asp Arg His Ala Leu Lys
    130                 135                 140
Thr Pro Asn Lys Lys Ala Ile Ile Phe Glu Gly Asp Glu Pro Gly Gln
145                 150                 155                 160
Gly Tyr Ser Ile Thr Tyr Lys Glu Leu Leu Glu Glu Val Cys Gln Val
                165                 170                 175
Ala Gln Val Leu Thr Tyr Ser Met Gly Val Arg Lys Gly Asp Thr Val
            180                 185                 190
Ala Val Tyr Met Pro Met Val Pro Glu Ala Ile Ile Thr Leu Leu Ala
        195                 200                 205
Ile Ser Arg Ile Gly Ala Ile His Ser Val Val Phe Ala Gly Phe Ser
    210                 215                 220
Ser Asn Ser Leu Arg Asp Arg Ile Asn Asp Gly Asp Ser Lys Val Val
225                 230                 235                 240
Ile Thr Thr Asp Glu Ser Asn Arg Gly Gly Lys Val Ile Glu Thr Lys
                245                 250                 255
Arg Ile Val Asp Asp Ala Leu Arg Glu Thr Pro Gly Val Arg His Val
            260                 265                 270
Leu Val Tyr Arg Lys Thr Asn Asn Pro Ser Val Ala Phe His Ala Pro
        275                 280                 285
Arg Asp Leu Asp Trp Ala Thr Glu Lys Lys Tyr Lys Thr Tyr Tyr
    290                 295                 300
Pro Cys Thr Pro Val Asp Ser Glu Asp Pro Leu Phe Leu Leu Tyr Thr
305                 310                 315                 320
Ser Gly Ser Thr Gly Ala Pro Lys Gly Val Gln His Ser Thr Ala Gly
                325                 330                 335
Tyr Leu Leu Gly Ala Leu Leu Thr Met Arg Tyr Thr Phe Asp Thr His
            340                 345                 350
Gln Glu Asp Val Phe Phe Thr Ala Gly Asp Ile Gly Trp Ile Thr Gly
        355                 360                 365
His Thr Tyr Val Val Tyr Gly Pro Leu Leu Tyr Gly Cys Ala Thr Leu
    370                 375                 380
Val Phe Glu Gly Thr Pro Ala Tyr Pro Asn Tyr Ser Arg Tyr Trp Asp
385                 390                 395                 400
Ile Ile Asp Glu His Lys Val Thr Gln Phe Tyr Val Ala Pro Thr Ala
                405                 410                 415
Leu Arg Leu Leu Lys Arg Ala Gly Asp Ser Tyr Ile Glu Asn His Ser
            420                 425                 430
Leu Lys Ser Leu Arg Cys Leu Gly Ser Val Gly Glu Pro Ile Ala Ala
        435                 440                 445
Glu Val Trp Glu Trp Tyr Ser Glu Lys Ile Gly Lys Asn Glu Ile Pro
    450                 455                 460
Ile Val Asp Thr Tyr Trp Gln Thr Glu Ser Gly Ser His Leu Val Thr
465                 470                 475                 480
Pro Leu Ala Gly Gly Val Thr Pro Met Lys Pro Gly Ser Ala Ser Phe
                485                 490                 495
Pro Phe Phe Gly Ile Asp Ala Val Val Leu Asp Pro Asn Thr Gly Glu
            500                 505                 510
```

```
Glu Leu Asn Thr Ser His Ala Glu Gly Val Leu Ala Val Lys Ala Ala
            515                 520                 525
Trp Pro Ser Phe Ala Arg Thr Ile Trp Lys Asn His Asp Arg Tyr Leu
        530                 535                 540
Asp Thr Tyr Leu Asn Pro Tyr Pro Gly Tyr Tyr Phe Thr Gly Asp Gly
545                 550                 555                 560
Ala Ala Lys Asp Lys Asp Gly Tyr Ile Trp Ile Leu Gly Arg Val Asp
                565                 570                 575
Asp Val Val Asn Val Ser Gly His Arg Leu Ser Thr Ala Glu Ile Glu
            580                 585                 590
Ala Ala Ile Ile Glu Asp Pro Ile Val Ala Glu Cys Ala Val Val Gly
        595                 600                 605
Phe Asn Asp Asp Leu Thr Gly Gln Ala Val Ala Ala Phe Val Val Leu
610                 615                 620
Lys Asn Lys Ser Ser Trp Ser Thr Ala Thr Asp Asp Glu Leu Gln Asp
625                 630                 635                 640
Ile Lys Lys His Leu Val Phe Thr Val Arg Lys Asp Ile Gly Pro Phe
                645                 650                 655
Ala Ala Pro Lys Leu Ile Ile Leu Val Asp Asp Leu Pro Lys Thr Arg
            660                 665                 670
Ser Gly Lys Ile Met Arg Arg Ile Leu Arg Lys Ile Leu Ala Gly Glu
        675                 680                 685
Ser Asp Gln Leu Gly Asp Val Ser Thr Leu Ser Asn Pro Gly Ile Val
    690                 695                 700
Arg His Leu Ile Asp Ser Val Lys Leu
705                 710

<210> SEQ ID NO 18
<211> LENGTH: 2142
<212> TYPE: DNA
<213> ORGANISM: Saccharomyces cerevisiae

<400> SEQUENCE: 18
atgtcgccct ctgccgtaca atcatcaaaa ctagaagaac agtcaagtga aattgacaag      60
ttgaaagcaa aaatgtccca gtctgccgcc actgcgcagc agaagaagga acatgagtat     120
gaacatttga cttcggtcaa gatcgtgcca caacggccca tctcagatag actgcagccc     180
gcaattgcta cccactattc tccacacttg acgggttgca aggactatca gcgcttgcac     240
aaggagtcta ttgaagaccc tgctaagttc ttcggttcta agctacccaa attttaaac     300
tggtctaagc cattcgataa ggtgttcatc ccagacccta aaacgggcag gccctccttc     360
cagaacaatg catggttcct caacggccaa ttaaacgcct gttacaactg tgttgacaga     420
catgccttga agactcctaa caagaaagcc attattttcg aaggtgacga gcctggccaa     480
ggctattcca ttacctacaa ggaactactt gaagaagttt gtcaagtggc acaagtgctg     540
acttactcta tgggcgttcg caagggcgat actgttgccg tgtacatgcc tatggtccca     600
gaagcaatca taaccttgtt ggccatttcc cgtatcggtg ccattcactc cgtagtcttt     660
gccgggtttt cttccaactc cttgagagat cgtatcaacg atggggactc taaagttgtc     720
atcactacag atgaatccaa cagaggtggt aaagtcattg agactaaaag aattgttgat     780
gacgcgctaa gagagacccc aggcgtgaga cacgtcttgg tttatagaaa gaccaacaat     840
ccatctgttg ctttccatgc ccccagagat ttggattggg caacagaaaa gaagaaatac     900
aagacctact atccatgcac acccgttgat tctgaggatc cattattctt gttgtatacg     960
```

```
tctggttcta ctggtgcccc caagggtgtt caacattcta ccgcaggtta cttgctggga    1020
gctttgttga ccatgcgcta cacttttgac actcaccaag aagacgtttt cttcacagct    1080
ggagacattg gctggattac aggccacact tatgtggttt atggtcccctt actatatggt   1140
tgtgccactt tggtctttga agggactcct gcgtacccaa attactcccg ttattgggat    1200
attattgatg aacacaaagt cacccaattt tatgttgcgc caactgcttt gcgtttgttg    1260
aaaagagctg gtgattccta catcgaaaat cattccttaa aatctttgcg ttgcttgggt    1320
tcggtcggtg agccaattgc tgctgaagtt tgggagtggt actctgaaaa aataggtaaa    1380
aatgaaatcc ccattgtaga cacctactgg caaacagaat ctggttcgca tctggtcacc    1440
ccgctggctg gtggtgttac accaatgaaa ccgggttctg cctcattccc cttcttcggt    1500
attgatgcag ttgttcttga ccctaacact ggtgaagaac ttaacaccag ccacgcagag    1560
ggtgtccttg ccgtcaaagc tgcatggcca tcatttgcaa gaactatttg gaaaaatcat    1620
gataggtatc tagacactta tttgaaccct taccctggct actatttcac tggtgatggt    1680
gctgcaaagg ataaggatgg ttatatctgg attttgggtc gtgtagacga tgtggtgaac    1740
gtctctggtc accgtctgtc taccgctgaa attgaggctg ctattatcga agatccaatt    1800
gtggccgagt gtgctgttgt cggattcaac gatgacttga ctggtcaagc agttgctgca    1860
tttgtggtgt tgaaaaacaa atctagttgg tccaccgcaa cagatgatga attacaagat    1920
atcaagaagc atttggtctt tactgttaga aaagacatcg gccatttgc  cgcaccaaaa    1980
ttgatcattt tagtggatga cttgcccaag acaagatccg gcaaaattat gagacgtatt    2040
ttaagaaaaa tcctagcagg agaaagtgac caactaggcg acgtttctac attgtcaaac    2100
cctggcattg ttagacatct aattgattcg gtcaagttgt aa                       2142
```

<210> SEQ ID NO 19
<211> LENGTH: 1119
<212> TYPE: PRT
<213> ORGANISM: Saccharomyces cerevisiae

<400> SEQUENCE: 19

```
Met Thr Glu Arg Ile Pro Ile Lys Asn Tyr Gln Arg Thr Asn Ala Lys
1               5                   10                  15

Ala Leu Leu Lys Leu Thr Glu Lys Leu Phe Asn Lys Asn Phe Phe Asp
                20                  25                  30

Leu Tyr Leu Thr Ser Gln Gln Leu Val Val Leu Glu Tyr Leu Leu Ser
            35                  40                  45

Ile Ser Ser Glu Glu Asp Lys Leu Lys Ala Trp Asp Tyr Phe Leu Lys
        50                  55                  60

Gly Asn Ile Ala Leu Asn Val Glu Lys Ser Phe Pro Leu Thr Gln Glu
65                  70                  75                  80

Glu Glu His His Gly Ala Val Ser Pro Ala Val Asp Thr Arg Ser Asp
                85                  90                  95

Asp Val Ser Ser Gln Thr Ile Lys Asp Asn Asn Thr Asn Thr Asn
                100                 105                 110

Thr Ser Ile Ser Asn Glu Asn His Val Glu Asn Glu Ile Glu Asp Lys
            115                 120                 125

Gly Asp Asn Ala Ile Ala Asn Glu Asp Asn Phe Val Asn Asn Asp Glu
        130                 135                 140

Ser Asp Asn Val Glu Glu Asp Leu Phe Lys Leu Asp Leu Glu Asp Leu
145                 150                 155                 160

Lys Gln Gln Ile Ser Gly Thr Arg Phe Ile Gly Asn Leu Ser Leu Lys
                165                 170                 175
```

```
Ile Arg Tyr Val Leu Trp Gln Cys Ala Ile Asp Tyr Ile Tyr Cys Asp
            180                 185                 190

Arg Asn Glu Phe Gly Asp Glu Asn Asp Thr Glu Tyr Thr Leu Leu Asp
            195                 200                 205

Val Glu Lys Glu Glu Glu Glu Ile Gly Lys Asn Glu Lys Pro Gln
210                 215                 220

Asn Lys Glu Gly Ile Ser Lys Phe Ala Glu Asp Glu Tyr Asp Asp
225                 230                 235                 240

Glu Asp Glu Asn Tyr Asp Glu Asp Ser Thr Asp Val Lys Asn Val Asp
                245                 250                 255

Asp Pro Pro Lys Asn Leu Asp Ser Ile Ser Ser Asn Ile Glu Ile
            260                 265                 270

Asp Asp Glu Arg Arg Leu Val Leu Asn Ile Ser Ile Ser Lys Glu Thr
            275                 280                 285

Leu Ser Lys Leu Lys Thr Asn Asn Val Glu Glu Ile Met Gly Asn Trp
    290                 295                 300

Asn Lys Ile Tyr His Ser Phe Glu Tyr Asp Lys Glu Thr Met Ile Lys
305                 310                 315                 320

Arg Leu Lys Leu Glu Glu Ser Asp Lys Met Ile Glu Lys Gly Lys Lys
                325                 330                 335

Lys Arg Ser Arg Ser Asp Leu Glu Ala Ala Thr Asp Glu Gln Asp Arg
            340                 345                 350

Glu Asn Thr Asn Asp Glu Pro Asp Thr Asn Gln Lys Leu Pro Thr Pro
                355                 360                 365

Glu Gly Ser Thr Phe Ser Asp Thr Gly Asn Lys Arg Pro Lys Gln Ser
    370                 375                 380

Asn Leu Asp Leu Thr Val Asn Leu Gly Ile Glu Asn Leu Ser Leu Lys
385                 390                 395                 400

His Leu Ser Ser Ile Gln Gln Lys Lys Ser Gln Leu Gly Ile Ser
                405                 410                 415

Asp Tyr Glu Leu Lys His Leu Ile Met Asp Val Arg Lys Asn Arg Ser
            420                 425                 430

Lys Trp Thr Ser Asp Glu Arg Ile Gly Gln Glu Glu Leu Tyr Glu Ala
            435                 440                 445

Cys Glu Lys Val Val Leu Glu Leu Arg Asn Tyr Thr Glu His Ser Thr
450                 455                 460

Pro Phe Leu Asn Lys Val Ser Lys Arg Glu Ala Pro Asn Tyr His Gln
465                 470                 475                 480

Ile Ile Lys Lys Ser Met Asp Leu Asn Thr Val Leu Lys Lys Leu Lys
                485                 490                 495

Ser Phe Gln Tyr Asp Ser Lys Gln Glu Phe Val Asp Asp Ile Met Leu
            500                 505                 510

Ile Trp Lys Asn Cys Leu Thr Tyr Asn Ser Asp Pro Ser His Phe Leu
            515                 520                 525

Arg Gly His Ala Ile Ala Met Gln Lys Lys Ser Leu Gln Leu Ile Arg
    530                 535                 540

Met Ile Pro Asn Ile Thr Ile Arg Asn Arg Ala Asp Leu Glu Lys Glu
545                 550                 555                 560

Ile Glu Asp Met Glu Lys Asp Lys Asp Tyr Glu Leu Ser Glu Glu Glu
                565                 570                 575

Glu Val Ala Gly Ser Gly Arg Lys Gly Leu Asn Met Gly Ala His Met
            580                 585                 590

Leu Ala Lys Glu Asn Gly Lys Val Ser Glu Lys Asp Ser Ser Lys Thr
```

595                 600                 605
Val Lys Asp Glu Ala Pro Thr Asn Asp Lys Leu Thr Ser Val Ile
610                 615                 620

Pro Glu Gly Glu Lys Glu Lys Asp Lys Thr Ala Ser Ser Thr Val Thr
625                 630                 635                 640

Val His Glu Asn Val Asn Lys Asn Glu Ile Lys Glu Asn Gly Lys Asn
            645                 650                 655

Glu Glu Gln Asp Met Val Glu Glu Ser Ser Lys Thr Glu Asp Ser Ser
            660                 665                 670

Lys Asp Ala Asp Ala Ala Lys Lys Asp Thr Glu Asp Gly Leu Gln Asp
            675                 680                 685

Lys Thr Ala Glu Asn Lys Glu Ala Gly Glu Asn Asn Glu Glu Glu Glu
            690                 695                 700

Asp Asp Asp Asp Glu Asp Glu Asp Met Val Asp Ser Gln Ser
705                 710                 715                 720

Tyr Leu Leu Glu Lys Asp Asp Arg Asp Asp Leu Glu Ile Ser Val
                725                 730                 735

Trp Lys Thr Val Thr Ala Lys Val Arg Ala Glu Ile Cys Leu Lys Arg
            740                 745                 750

Thr Glu Tyr Phe Lys Asn Gly Lys Leu Asn Ser Asp Ser Glu Ala Phe
            755                 760                 765

Leu Lys Asn Pro Gln Arg Met Lys Arg Phe Asp Gln Leu Phe Leu Glu
            770                 775                 780

Tyr Lys Glu Gln Lys Ala Leu Glu Ser Tyr Arg Gln Lys Ile Glu Gln
785                 790                 795                 800

Asn Ser Ile Met Lys Asn Gly Phe Gly Thr Val Leu Lys Gln Glu Asp
                805                 810                 815

Asp Asp Gln Leu Gln Phe His Asn Asp His Ser Leu Asn Gly Asn Glu
            820                 825                 830

Ala Phe Glu Lys Gln Pro Asn Asp Ile Glu Leu Asp Thr Arg Phe
            835                 840                 845

Leu Gln Glu Tyr Asp Ile Ser Asn Ala Ile Pro Asp Ile Val Tyr Glu
850                 855                 860

Gly Val Asn Thr Lys Thr Leu Asp Lys Met Glu Asp Ala Ser Val Asp
865                 870                 875                 880

Arg Met Leu Gln Asn Gly Ile Asn Lys Gln Ser Arg Phe Leu Ala Asn
                885                 890                 895

Lys Asp Leu Gly Leu Thr Pro Lys Met Asn Gln Asn Ile Thr Leu Ile
            900                 905                 910

Gln Gln Ile Arg His Ile Cys His Lys Ile Ser Leu Ile Arg Met Leu
            915                 920                 925

Gln Ser Pro Leu Ser Ala Gln Asn Ser Arg Ser Asn Pro Asn Ala Phe
930                 935                 940

Leu Asn Asn His Ile Tyr Asn Tyr Thr Ile Ile Asp Asp Ser Leu Asp
945                 950                 955                 960

Ile Asp Pro Val Ser Gln Leu Pro Thr His Asp Tyr Lys Asn Asn Arg
            965                 970                 975

Glu Leu Ile Trp Lys Phe Met His Lys Asn Ile Ser Lys Val Ala Met
            980                 985                 990

Ala Asn Gly Phe Glu Thr Ala His Pro Ser Ala Ile Asn Met Leu Thr
            995                 1000                1005

Glu Ile Ala Gly Asp Tyr Leu Ser Asn Leu Ile Lys Thr Leu Lys
    1010                1015                1020

-continued

| Leu | His | His | Glu | Thr | Asn | Ser | Leu | Asn | Arg | Gly | Thr | Asn | Val | Glu |
| | 1025 | | | | 1030 | | | | | 1035 | | | | |

| Met | Leu | Gln | Thr | Thr | Leu | Leu | Glu | Asn | Gly | Ile | Asn | Arg | Pro | Asp |
| 1040 | | | | | 1045 | | | | | 1050 | | | | |

| Asp | Leu | Phe | Ser | Tyr | Val | Glu | Ser | Glu | Phe | Gly | Lys | Lys | Thr | Lys |
| | 1055 | | | | | 1060 | | | | | 1065 | | | |

| Lys | Leu | Gln | Asp | Ile | Lys | Gln | Lys | Leu | Glu | Ser | Phe | Leu | Arg | Ala |
| | 1070 | | | | | 1075 | | | | | 1080 | | | |

| Leu | Leu | Arg | Pro | Thr | Leu | Gln | Glu | Leu | Ser | Glu | Arg | Asn | Phe | Glu |
| | 1085 | | | | | 1090 | | | | | 1095 | | | |

| Asp | Glu | Ser | Gln | Ser | Phe | Phe | Thr | Gly | Asp | Phe | Ala | Ser | Glu | Leu |
| | 1100 | | | | | 1105 | | | | | 1110 | | | |

| Thr | Gly | Glu | Asp | Phe | Phe |
| | 1115 | | | | |

<210> SEQ ID NO 20
<211> LENGTH: 3357
<212> TYPE: DNA
<213> ORGANISM: Saccharomyces cerevisiae

<400> SEQUENCE: 20

```
atgactgaaa gaataccaat aaagaattat caaagaacaa atgccaaagc tttacttaaa     60
ttgactgaaa aacttttaa caagaacttt tttgatctct atttaacctc tcagcaattg    120
gtcgttcttg aatacctgct gtcgatttca agtgaagaag acaaactgaa agcatgggac    180
tatttcttaa agggaaacat agcattaaat gtcgaaaaat catttccatt aacccaagaa    240
gaagaacatc acggagcggt ctctcctgcc gttgacacac gatcagatga tgtatcatca    300
caaacaatta aggacaataa caatactaat accaacacca gtatcagcaa tgaaaatcat    360
gttgaaaatg aaattgaaga taaaggcgat aacgcaatag caaatgaaga taattttgtg    420
aataatgacg aaagtgataa tgttgaagaa gacttattca aattagatct agaggacttg    480
aagcagcaaa taagcggaac aaggtttatt ggaaacttat ccttgaaaat cagatacgtc    540
ttgtggcagt gcgccataga ttatatatac tgtgatcgta atgagtttgg tgatgaaaat    600
gatacagaat acaccctatt agatgttgaa gagaaggagg aagaggaaat tggtaaaaat    660
gagaagccac aaaacaaaga aggtatttcg aagttcgccg aggatgaaga ttacgacgat    720
gaagacgaga actatgatga agacagtaca gacgtaaaaa atgtcgatga tcctccaaaa    780
aatctcgatt ctatttcctc ttctaatatc gaaattgacg atgaacgacg cttggtgcta    840
aatatctcaa tatcaaagaa aacactgtca agttaaaaaa caataatgt agaagaaatt    900
atgggaaatt ggaacaaaat ttaccacagt tttgaatacg ataaagaaac tatgataaag    960
cgattaaaac ttgaagaaag cgataaaatg atagagaaag gaaagaagaa acgaagtcga   1020
agtgatttag aagcagctac cgatgaacaa gatcgcgaaa atacaaatga tgagccagat   1080
actaatcaaa aattgcccac tcctgaaggt tcaacattca gcgatactgg aacaagcgc    1140
cccaaacaaa gtaatttaga tttaacagtc aatctaggca tcgaaaattt atcattaaag   1200
caccttctat catctatcca gcaaaaaaaa tcccaattag gaatatcaga ttacgaatta   1260
aaacatctga ttatggatgt cagaaaaaat cggtcaaaat ggacatcgga tgaaagaatt   1320
gggcaagagg aattatacga agcctgtgaa aaggttgttt tggaacttag aaactacact   1380
gagcattcta caccatttct gaataaagtg agcaaaagag aagcccccaa ttatcatcaa   1440
atcatcaaaa agtccatgga cctgaatact gttttaaaaa aactgaaaag ctttcaatat   1500
gactccaaac aagaatttgt agacgatatt atgctaatat ggaaaaattg tttgacctat   1560
```

```
aattcagatc cttcacattt tttgagaggg catgctattg ctatgcagaa gaaatctctt    1620
cagttgattc gcatgattcc aaatatcaca atccgaaaca gggctgattt agaaaaggaa    1680
attgaagata tggaaaaaga caaagactac gaattagatg aggaagagga agttgctggt    1740
tctggaagaa aaggattgaa tatgggagct catatgttgg ccaagagaa tggcaaggtg     1800 tcagaaaaag atagctctaa aaccgtcaag gatgaagcac caaccaatga tgacaaacta    1860
acttctgtca tccctgaggg ggaaaaagag aaagataaaa ctgcttcatc tactgtaacg    1920
gtacacgaaa atgtaaataa gaacgaaata aagaaaatg ggaaaatga agagcaagat      1980 atggttgagg aaagtagtaa gactgaggat tcatcaaaag atgctgatgc tgccaaaaag    2040
gatacggaag acggactaca agataaaact gcagaaaata aggaggctgg ggaaaataat    2100
gaagaggaag aggatgatga tgacgaagat gaagacgaag acatggtcga ctcccaatct    2160
tatttacttg aaaaggatga cgatagagac gatttggaaa tatccgtgtg gaaaactgta    2220
actgccaaag ttcgtgcgga aatttgctta aaaagaactg aatattttaa aaatggaaaa    2280
ttaaatagtg attcagaggc gttttttgaaa acccacaaa gaatgaaaag gttcgaccag    2340 cttttttcttg aatataaaga gcagaaagct ttagaatcat atcgtcaaaa aatagagcaa   2400
aattccatta tgaaaaatgg ctttggaaca gtactaaaac aggaagacga tgaccaattg    2460
cagtttcata atgatcactc tttaaatgga aatgaagctt ttgaaaagca acccaatgat    2520
attgagttag atgataccag attcctacag gaatatgata ttagtaacgc cattcctgac    2580
atagtatacg agggagtaaa tactaaaaca ttagacaaga tggaagacgc ttccgtggac    2640
cgcatgcttc aaaatggtat caacaaacaa agcagatttc tggctaacaa ggatttagga    2700
ctaacaccta aaatgaacca aaatatcaca ctgattcagc aaattaggca catatgccat    2760
aaaatatccc tgatcagaat gttacagagc cctttatcgg ctcaaaactc cagaagcaat    2820
cccaacgctt tccttaacaa ccacatttat aattacacta ttattgatga ctcactcgat    2880
attgatccgg tgtcacagct tccaacgcat gattacaaaa acaacaggga gctgatatgg    2940
aaattcatgc ataagaacat atctaaggtt gctatggcca atgggtttga aactgcccat    3000
ccatcagcaa taaacatgct tactgaaatc gccggggatt acctatctaa tctgataaag    3060
actttgaagc ttcatcatga aactaactcc ttaaatagag gaacaaatgt ggaaatgctg    3120
caaacaacac tgttggaaaa cggtatcaac aggccagacg atctattttc ctatgttgaa    3180
tctgaatttg gtaaaaaaac taagaaactt caggacatca aacagaaact agaaagcttt    3240
ttgagagcct tattaaggcc aactttgcag gagttgtccg agagaaactt tgaagacgag    3300
agccaaagct tttttacagg tgactttgcc agcgaattga ctggtgaaga cttctttt      3357
```

<210> SEQ ID NO 21
<211> LENGTH: 337
<212> TYPE: PRT
<213> ORGANISM: Saccharomyces cerevisiae

<400> SEQUENCE: 21

```
Met Met Asp Lys His Lys Tyr Arg Val Glu Ile Gln Gln Met Met Phe
1               5                   10                  15

Val Ser Gly Glu Ile Asn Asp Pro Pro Val Glu Thr Thr Ser Leu Ile
            20                  25                  30

Glu Asp Ile Val Arg Gly Gln Val Ile Glu Ile Leu Leu Gln Ser Asn
        35                  40                  45

Lys Thr Ala His Leu Arg Gly Ser Arg Ser Ile Leu Pro Glu Asp Val
    50                  55                  60
```

Ile Phe Leu Ile Arg His Asp Lys Ala Lys Val Asn Arg Leu Arg Thr
65                  70                  75                  80

Tyr Leu Ser Trp Lys Asp Leu Arg Lys Asn Ala Lys Asp Gln Asp Ala
                85                  90                  95

Ser Ala Gly Val Ala Ser Gly Thr Gly Asn Pro Gly Ala Gly Gly Glu
            100                 105                 110

Asp Asp Leu Lys Lys Ala Gly Gly Glu Lys Asp Glu Lys Asp Gly
            115                 120                 125

Gly Asn Met Met Lys Val Lys Lys Ser Gln Ile Lys Leu Pro Trp Glu
        130                 135                 140

Leu Gln Phe Met Phe Asn Glu His Pro Leu Glu Asn Asn Asp Asp Asn
145                 150                 155                 160

Asp Asp Met Asp Glu Asp Glu Arg Glu Ala Asn Ile Val Thr Leu Lys
                165                 170                 175

Arg Leu Lys Met Ala Asp Asp Arg Thr Arg Asn Met Thr Lys Glu Glu
                180                 185                 190

Tyr Val His Trp Ser Asp Cys Arg Gln Ala Ser Phe Thr Phe Arg Lys
            195                 200                 205

Asn Lys Arg Phe Lys Asp Trp Ser Gly Ile Ser Gln Leu Thr Glu Gly
        210                 215                 220

Lys Pro His Asp Asp Val Ile Asp Ile Leu Gly Phe Leu Thr Phe Glu
225                 230                 235                 240

Ile Val Cys Ser Leu Thr Glu Thr Ala Leu Lys Ile Lys Gln Arg Glu
                245                 250                 255

Gln Val Leu Gln Thr Gln Lys Asp Lys Ser Gln Gln Ser Ser Gln Asp
                260                 265                 270

Asn Thr Asn Phe Glu Phe Ala Ser Ser Thr Leu His Arg Lys Lys Arg
            275                 280                 285

Leu Phe Asp Gly Pro Glu Asn Val Ile Asn Pro Leu Lys Pro Arg His
        290                 295                 300

Ile Glu Glu Ala Trp Arg Val Leu Gln Thr Ile Asp Met Arg His Arg
305                 310                 315                 320

Ala Leu Thr Asn Phe Lys Gly Gly Arg Leu Ser Ser Lys Pro Ile Ile
                325                 330                 335

Met

<210> SEQ ID NO 22
<211> LENGTH: 1014
<212> TYPE: DNA
<213> ORGANISM: Saccharomyces cerevisiae

<400> SEQUENCE: 22
atgatggaca agcataagta tcgtgtggag attcaacaga tgatgtttgt ctctggtgaa      60
attaacgacc cacccgtaga aaccacatca ctgatagaag atatagtgag gggtcaagtg     120
atagaaattc ttttacagtc aaacaaaacg gcgcatctta ggggaagtag gagcattctc     180
cctgaagacg tcattttctt gatcagacac gacaaggcca agtcaatcg tttgagaaca     240 tatctgtcat ggaaggattt gcgtaaaaac gccaaggacc aagatgctag tgccggtgta     300
gcgagtggca ctggaaatcc tggggcaggt ggtgaagatg atttgaaaaa agcaggtggt     360
ggcgagaaag acgaaaaaga tggtggaaac atgatgaagg tcaagaaatc ccaaattaag     420
ctgccatggg aattgcagtt tatgttcaat gaacatcctt tagaaaataa tgacgacaat     480
gatgatatgg atgaggatga acgagaagct aatatagtca ctttgaaaag gctgaaaatg     540

-continued

```
gctgacgata gaacacgaaa catgactaaa gaggagtacg tgcattggtc cgattgtcga        600
caggcaagtt ttacatttag gaagaataaa aggttcaagg actggtctgg aatttcgcaa        660
ttaactgagg ggaaacccca tgatgatgtg attgatatac tggggtttct aactttgag         720 attgtctgtt ctttgacgga aacagctctg aaaatcaaac aaagagaaca ggtattacag        780
actcaaaagg acaaatccca gcaatctagc caagataata ctaactttga atttgcatca        840
tccacattac atagaaagaa aagattattt gatggacctg aaaatgttat aaacccgctc        900
aaaccaaggc atatagagga agcctggaga gtactacaaa caattgacat gaggcatagg        960
gctttgacca actttaaagg tggtagactc agttctaaac caattatcat gtaa             1014
```

SCREENING METHOD FOR CELL AGING

FIELD OF INVENTION

The present invention relates to methods of screening to identify compounds which have an effect on ageing of a cell, more particularly chronological ageing of a cell, methods of diagnosing disorders related to a change in the chronological life span of a cell.

BACKGROUND

The target of rapamycin complex, TORC1, is conserved from yeast to man and has critical roles in sensing and signalling the nutrient and stress status of the cell, thus controlling the balance between cell growth[1-5] and cell survival[6-11]. In budding yeast TORC1 promotes fermentative growth on glucose and down regulates respiration[12, 13]. TORC1 contains a phosphatidylinositol kinase (PI3-K)-related kinase, either Tor1 or Tor2. The macrolide rapamycin[14], in a complex with Fpr1 (Fk506-sensitive Proline Rotamase), binds to Tor1/2 causing cells to enter a state that resembles nutrient limitation[15] probably due to a change in the substrate specificity of the Tor kinase[16]. This new state of the cell is associated with changes in patterns of gene expression, particularly genes required for respiration and stress resistance[6,10,17,18]. The expression of many TORC1 genes is dependent on the SAGA family of transcriptional co-activator complexes including SAGA (Spt-Ada-Gcn5-Acetyltransferase)[19,20], SLIK (SAGA-like)[21] and SALSA (SAGA altered, Spt8 absent)[22-24]. SAGA, SLIK and SALSA contain the lysine acetyltransferase (KAT) Gcn5[21-23], with lysine 14 on histone H3 (H3K14ac) as a substrate, but differ in their abundance, the genes they regulate and subunit composition[19,24]

The inventors have discovered that H3K18 acetylation, is central to a mechanism that controls the balance between cell growth and longevity. They have also identified a number of genes involved in the SAGA SLIK and SALSA complexes whose disruption results in an increase in chronological lifespan.

SUMMARY OF THE INVENTION

According to a first aspect of the present invention there is provided a method for increasing the chronological lifespan of a cell comprising disrupting the function of at least one of the SAGA, SLIK and/or SALSA complexes in said cell.

According to a second aspect of the present invention there is provided a method for identifying a potential modulator of the chronological life span (CLS) of a cell, comprising the steps of
  i) contacting a cell having a known Histone 3 Lysine 18 (H3K18) acetylation status with a test compound; and
  ii) determining if said compound has an effect on the acetylation status of H3K18 in said cell;
wherein, a change in the acetylation status of H3K18 in the cell indicates that the compound modulates CLS.

According to a third aspect of the present invention there is provided a modulator of the CLS of a cell identified by the method of the second aspect.

According to an fourth aspect of the present invention there is provided a method for identifying the replication status of a cell comprising identifying the acetylation state of H3K18, wherein the presence of an acetyl modification of H3K18 indicates that the cell is an actively replicating cell and the absence of an acetyl modification of H3K18 indicates a cell which is no longer replicating.

According to a fifth aspect of the present invention there is provided a method of identifying a change in the CLS of a cell comprising identifying the acetylation state of H3K18 in the cell and comparing this to the acetylation state of a control cell, wherein loss of H3K18Ac when compared to the control cell indicates an increased CLS and acquisition of H3K18Ac when compared to the control cell indicates a reduced CLS.

According to a sixth aspect of the present invention there is provided a method of diagnosing a disorder associated with a change in the CLS of a cell, said method comprising identifying the acetylation status of H3K18 in a cell previously isolated from a subject and comparing said acetylation status to the acetylation status of a control cell.

DETAILED DESCRIPTION OF THE INVENTION

It will be understood that any preferred embodiments described herein in relation to one aspect of the present invention can, where appropriate, be equally applicable to any other aspect of the invention.

According to a first aspect there is provided a meth. for increasing the chronological lifespan of a cell comprising disrupting the function of at least one of the SAGA, SLIK and/or SALSA complexes in said cell.

As used herein the term chronological life span refers to the time cells in a stationary phase culture remain viable.

It will be understood that the function of the at least one of the SAGA, SLIK and/or SALSA complexes may be disrupted directly or indirectly. These complexes play a crucial role in controlling of the acetylation state and CLS of a cell, but differ in their levels depending upon the status of the cell and its environment.

As used herein the terms directly and indirectly in relation to interaction with the recited complexes refer to an interaction with either the complex itself, or with a gene product from a gene encoding a peptide which forms part of the complex, or with the gene product from a gene which allows the complex to form.

Preferably, disruption is effected through disruption of at least one gene or a product of at least one gene selected from the group consisting of Spt3, Rtg2, Gcn5, Ubp8, Spt7, Spt8 and/or Snf1 or their homologues.

The term homologue as used herein refers to an analogous gene from a different organism which performs the same function and in general shows some degree of sequence homology. The skilled person will understand that the above genes from *S. cerevisiae* have homologues in other organisms including mammels. For example, Spt3 shows homology to human SUPT3H-203; Gcn5 shows homology to human KAT2B-001 and KAT2A-001; Spt7 shows homology to human SUPT7H and SNF1 shows homology to PRKAA1 and PRKAA2.

It will be understood that these genes encode products which form part of the SAGA, SLIK and/or SALSA complexes, or interact with said complexes in manner so as to affect acetylation of histones in a cell.

Preferably, the disruption is effected through disruption of SPT7 (SEQ ID NO:11) or SPT7-217 (SEQ ID NO:19).

As used herein the term "disrupting the function", "disruption of the function" or "disrupts the function" when used in relation to a gene or gene product refers to disrupting the expression of the gene or disrupting the activity of the encoded polypeptide. It will be further understood that any stage of gene expression between initiation of transcription and production of a mature protein can be disrupted. The skilled person will understand that this will include epigenetic means of controlling gene expression through controlling chromatin structure as well as transcriptional, translational and post translation means of controlling gene expression.

It will be understood that by disrupting expression of a gene as used herein is meant preventing or inhibiting production of a functional polypeptide by any means known in the art and that disrupting the activity of the encoded polypeptide refers to disrupting interaction of the functional polypeptide with one or more of it's binding partners such that the polypeptide does not perform it's function. The production or function may be fully or partially prevented. In one embodiment, preferably the production or function of the gene product is fully prevented, i.e. there is no active gene product. In some instances the production or function of the gene product may be disrupted such that there is only about 5%, about 10% about 20%, about 30%, about 50%, about 60%, about 70%, about 80%, about 90% or about 95% of the wild type level of expression remaining.

As used herein by inhibiting production of a functional polypeptide it is meant that the production of the gene product may be prevented or inhibited by (a) knocking out said gene; (b) post-transcriptionally silencing said gene through for example the use of iRNA or antisense RNA (gene silencing); (c) transcriptionally silencing said gene by, for example, epigenetic techniques; (d) preventing or altering the function of the gene product by the introduction of at least one point mutation; (e) post translationally inactivating the gene product.

In one preferred embodiment, expression of the gene or homologue is disrupted by iRNA.

Preferably, the cell is transformed with a plasmid/vector encoding an iRNA under control of a promoter. It will be apparent that this promoter may be a constitutive promoter and/or a tissue specific promoter.

As used herein the term iRNA refers to RNA interference (RNAi). This is a method of post-transcriptional gene silencing (PIGS) in eukaryotes induced by the direct introduction of dsRNA (Fire A, et al., (1998)).

In a further preferred embodiment expression of the gene is disrupted at the transcriptional/DNA level. Preferably, said disruption is effected by insertion of at least one nucleotide into the gene or deletion of at least one nucleotide from the gene.

In a further embodiment, the disruption of the gene is effected by introduction of at least one point mutation.

It will be understood that in the case of disruption of the interaction of the polypeptide with one or more of it's binding partners. this disruption can be by any suitable means, for example, competitive inhibition, non-competitive inhibition, mixed inhibition or uncompetitive inhibition.

The present invention encompasses the use of sequences having a degree of sequence identity or sequence homology with amino acid sequences of the polypeptides defined herein or of any nucleotide sequence encoding such a polypeptide (hereinafter referred to as a "homologous sequence(s)"). Here, the term "homologous" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 50, 60, 70, 75, 80, 85 or 90% identical, preferably at least 95%, 97%, 98% or 99% identical to the subject sequence. Typically, the homologues will comprise the same active sites etc. as the subject amino acid sequence. Although homology can also be considered in terms of similarity (i.e. amino acid residues having similar chemical properties/functions).

In the present context, a homologous sequence is taken to include nucleotide sequence which may be at least 50, 60, 70, 75, 80, 85 or 90% identical, preferably at least 95%, 97%, 98% or 99% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions).

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8 and tatian@ncbi.nlm.nih.qov), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60).

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

As used herein, the term fragment refers to a fragment of the sequence which provides and/or encodes a polypeptide which retains the functional activity and/or enhances the activity of the enzyme.

When referring to a polypeptide fragment, preferably, the fragment is at least 50 amino acids in length. More preferably, the fragment comprises at least 100, 200, 300, 400 or 500 600, 700, 800, 900 or 1000 continuous amino acids from the subject sequence, for example SEQ ID NO:19, up to and including a polypeptide comprising one amino acid less than the full length protein.

When referring to a polynucleotide fragment, preferably the fragment comprises at least 100 nucleotides, more preferably, at least 200, 500, 800, 1000, 1500 or more nucleotides, up to and including a polynucleotide comprising one nucleotide less than the full length polynucleotide.

It will be understood by the skilled person that polynucleotides encoding a particular polypeptide can differ from each other due to the degeneracy of the genetic code. Included herein are the use of such polynucleotides encoding the polypeptide of the present invention.

It will be further apparent to the skilled person that the term homologous sequence in relation to a polynucleotide sequence can refer to a sequence which binds under stringent conditions to the polynucleotide sequence.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. t. 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

In a preferred aspect, the present invention covers nucleotide sequences that can hybridise to the nucleotide sequence of the present invention under stringent conditions (e.g. 65° C. and 0.1×SSC {1×SSC=0.15 M NaCl, 0.015 M $Na_3$ Citrate pH 7.0). Where the nucleotide sequence of the invention is double-stranded, both strands of the duplex, either individually or in combination, are encompassed by the present invention. Where the nucleotide sequence is single-stranded, it is to be understood that the complementary sequence of that nucleotide sequence is also included within the scope of the present invention.

Nucleotide sequences which are not 100% homologous to the sequences of the present invention but fall within the scope of the invention can be obtained in a number of ways. Other variants of the sequences described herein may be obtained for example by probing DNA libraries made from a range of sources. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the nucleotide sequence set out in herein under conditions of medium to high stringency. Similar considerations apply to obtaining species homologues and allelic variants of the amino acid and/or nucleotide sequences of the present invention. In another aspect of the present invention there is provided a method for identifying a potential modulator of the chronological life span (CLS) of a cell, comprising the steps of i) contacting a cell having a known Histone 3 Lysine 18 (H3K18) acetylation status with a test compound; and
ii) determining if said compound has an effect the acetylation status of H3K18 in said cell;

wherein, a change in the acetylation status of H3K18 in the cell indicates that the compound modulates CLS.

It is known that modification of the histone components of chromatin often reflect whether genes are active or repressed and these changes are globally regulated by enzymes that deposit or remove specific modifications. On active genes, the chromatin is often modified by lysine (K) acetylation (ac) or methylation (me), particularly of histone H3. The inventors have identified a new lysine in histone H3 whose modification status appears to play a critical role in determining the lifespan of a cell.

As used herein, the term modulator of the chronological life span refers to a compound which has an effect on the CLS of the cell. This effect may be to increase the CLS of the cell or to decrease the CLS of the cell. It will be understood that, dependent upon the purpose to which the compound is to be put, either effect may be desirable.

It will be understood that the compound referred to herein may be any suitable compound and may be, for example, a small molecule compound or equally a biological molecule such as a peptide or nucleic acid.

Preferably, the compound interacts with at least one gene or a product of at least one gene selected from the group consisting of Spt3 (SEQ ID NO: 22), Rtg2 (SEQ ID NO: 4), Gcn5 (SEQ ID NO: 6), Ubp8 (SEQ ID NO: 10), Spt7 (SEQ ID NO: 12), Spt8 (SEQ ID NO: 14) and/or Snf1 (SEQ ID NO: 16) or their homologues.

It will be apparent to the skilled person that the gene with which the compound interacts can be identified through the use of various knock out mutant strains.

Methods of producing such strains are well known to the skilled person and include for example, insertion of one or more nucleotides into the coding region of the gene. It will be understood that, as used herein, the term product of at least one gene refers to either a nucleic acid, e.g. mRNA, or peptide product.

In a further preferred embodiment, the compound interacts with the gene designated Acs1 (SEQ ID No: 18) or a product of the gene designated Acs1.

It will be further apparent to the skilled person that the acetylation status of H3K18 can be identified by any suitable means known in the art.

In one embodiment, the acetylation status is determined by measurement of mitochondrial respiration.

It will be understood by the skilled person that any suitable method for measuring mitochondrial respiration can be used. For example, mitochondrial respiration can be measured by incubating the cells in the presence DIOC6 and visualising the cells.

In an alternative embodiment, the acetylation status is determined by indirect immunofluorescence with monoclonal antibodies against H3K18ac on live or fixed cells.

The present invention also provides methods for identifying the replication status of a cell or identifying a change in the CLS of a cell.

As used herein, the term identifying the replication status refers to identifying whether a particular cell or population of cells is actively dividing, or capable of actively dividing or whether the cell or population of cells are no longer able divide.

As used herein, the term identifying a change in the CLS of a cell refers to identifying a step change in a cell or population of cells from a state in which it/they is/are capable of actively dividing to a state in which it/they can no longer divide or vice versa.

It will be understood that this change can be deliberately induced or can occur naturally or through exposure to environmental factors.

Preferably, the cell is a mammalian cell. More preferably, the cell is a human cell. In one preferred embodiment, the cell is an induced pluripotent stem cell.

The skilled person will understand that an induced pluripotent stem cell is typically a somatic cell which has been caused to regress to a pluripotent state either by exposure to certain chemicals or through transfection with, for example, various viruses.

In a further preferred embodiment the cell is a cell suspected of being neoplastic and/or cancerous. Preferably, the cell is a cell from a sample which has previously been isolated from a patient suspected of having or at risk of developing cancer.

In a further aspect, their is provided a method of diagnosing a disorder associated with a change in the CLS of a cell, said method comprising identifying the acetylation status of H3K18 of a cell previously isolated from a subject and comparing said acetylation status to the acetylation status of a control cell.

As used herein, the term control cell refers to a cell of the same tissue type as that isolated from the subject, the control cell being isolated from healthy tissue and having a known acetylation status.

Preferably, said disorder is selected from the group comprising an age related disorder, cancer, a blood disorder, Parkinson's disease or Alzheimer's disease.

The invention will be further described with reference to the figures. References to strains in the figures refer to the strains disclosed in Table 1. In the figures:—

FIG. 1 H3K14ac by SAGA reflects growth. FIG. 1 shows Western blots showing levels of various post-translational modifications to histone H3, in various backgrounds including HA-Spt7 and Gcn5 in total cell extract prepared from cells mock-treated or treated with 10 µM rapamycin for up to 180 minutes in the BY4741 background (a, b, c, d), FY168 and FY571 (e, h), FY2 and FY2030 (f) and JR-52A (g). In panel e The version of Spt7 expressed from the spt7-217 allele in FY571 is truncated at amino acid 1119 and has lost 213 C-terminal residues.

FIG. 2 SAGA and K14ac influence ageing. Western blots showing levels of K14ac (a) and HA-Spt7 (b) in total protein prepared from $1 \times 10^8$ cells of the FY2030 background (a, b) or FY168 and FY571 (c), subject to biotinylation, growth for 10 or 20 generations in exponential culture (YPD) and isolation using magnetic streptavidin beads. Young cells (majority less than 5 generations old) were prepared from the remaining non-biotinylated cells. * indicates a processed version of histone H3.

FIG. 3 Control of SAGA, SLIK and K14ac. Western blots showing levels of H3K14ac Gcn5 or HA-Spt7 in total cell extracts prepared from the strains indicated (genotype shown in Table 1) after growth in the presence of 10 µM rapamycin (+) or mock-treated (−) for 3 hours. WT strains are BY4741.

FIG. 4 Rtg2 and SLIK determine chronological lifespan. a FY168 (WT), FY571 (Spt7-217) and rtg2Δ derivatives in exponential phase stained with DiOC6 to assess mitochondrial membrane potential (ψ). Scale bar is 10 µm. b Serial ten-fold dilutions of cells from strains indicated grown with aeration to stationary phase in CSM containing 3% glucose and plated onto YDP on the day shown to assess viability. The average lifespan (time in days to 50% drop in viability) was calculated from colony counts. c Fluorographs of total protein extracts in exponential phase treated without or with cyclohexamide to inhibit cytoplasmic translation and pulse labelled for 15 minutes with 35S methionine.

FIG. 5 shows Western blots showing levels of various post-translational modifications to histone H3 in total cell extract prepared from BY4741 in exponential or early stationary phase.

FIG. 6 a shows the effect of expressing a C-terminally truncated version of Spt7 (Spt7-217) in strain FY571 and derivatives on K14ac and gene expression. FIGS. 6b-i show the effect of growth phase and the presence of RTG2 on the induction of various genes.

Figure 10:
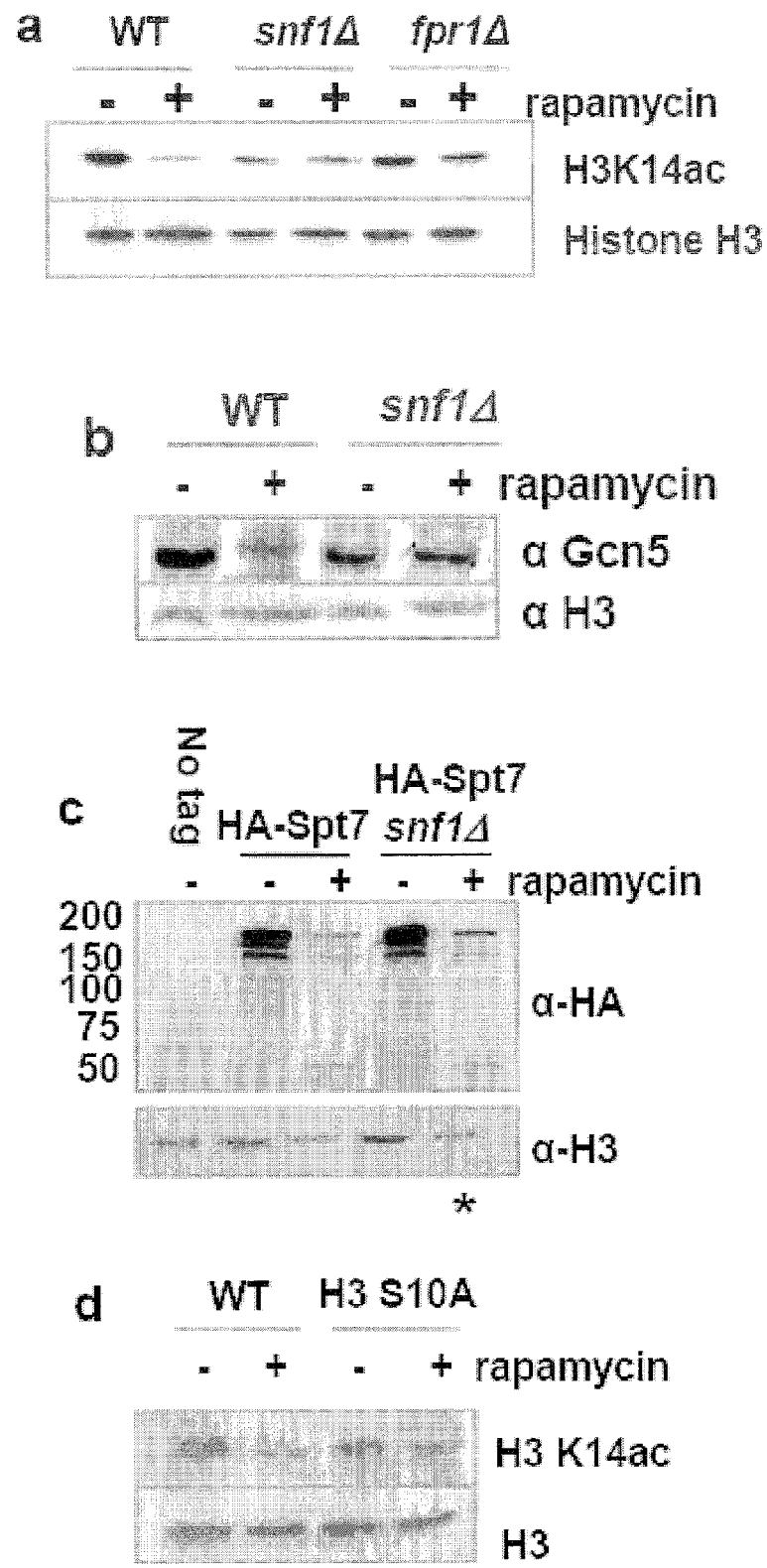
Figure 10:
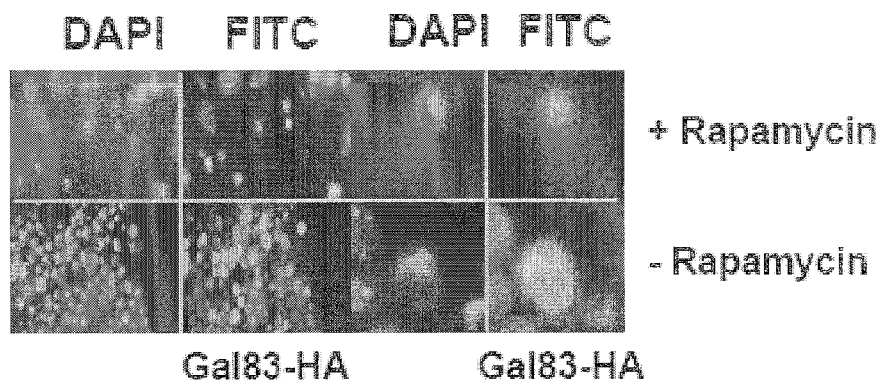
Figure 10:
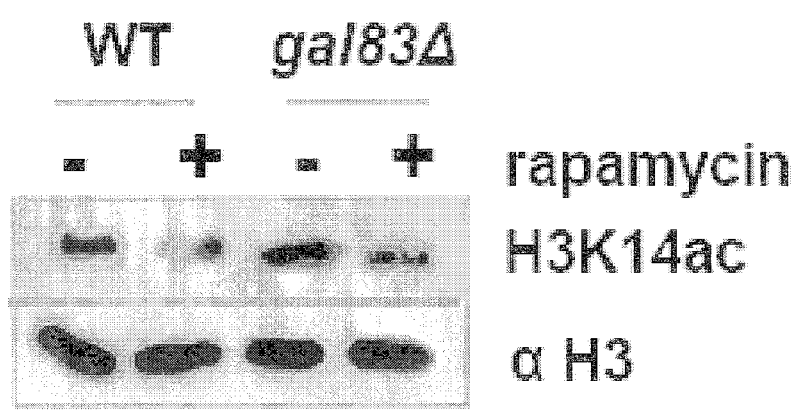
Figure 10:
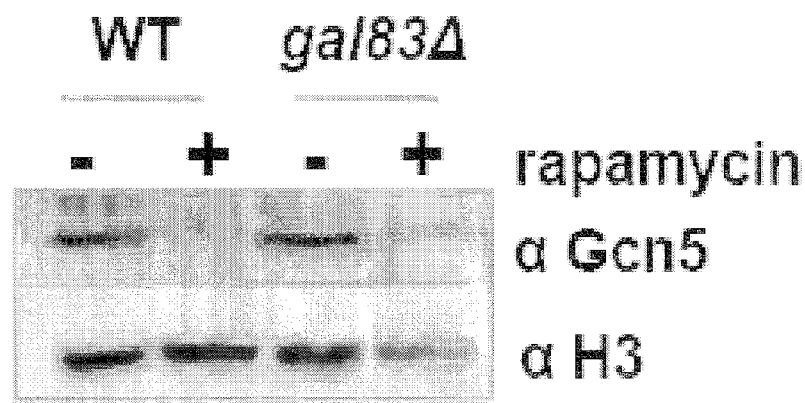

FIG. 10 shows that Snf1 is required for the rapamycin dependent reduction in K14ac on rapamycin treatment. a-d Western blots showing levels of modifications at H3 on total cell extracts prepared from the strains indicated in the LPY8056 background (d), BY4741 (a-b, f-g) or FY3 (c). n=3 for all experiments shown. e Indirect immunofluorescence with FITC tagged anti-HA antibody (right panel) or DAPI (DNA) (left panel) of Gal83-HA. Cells were treated +/−10 µM rapamycin for up to 3 hours.

Figure 11:
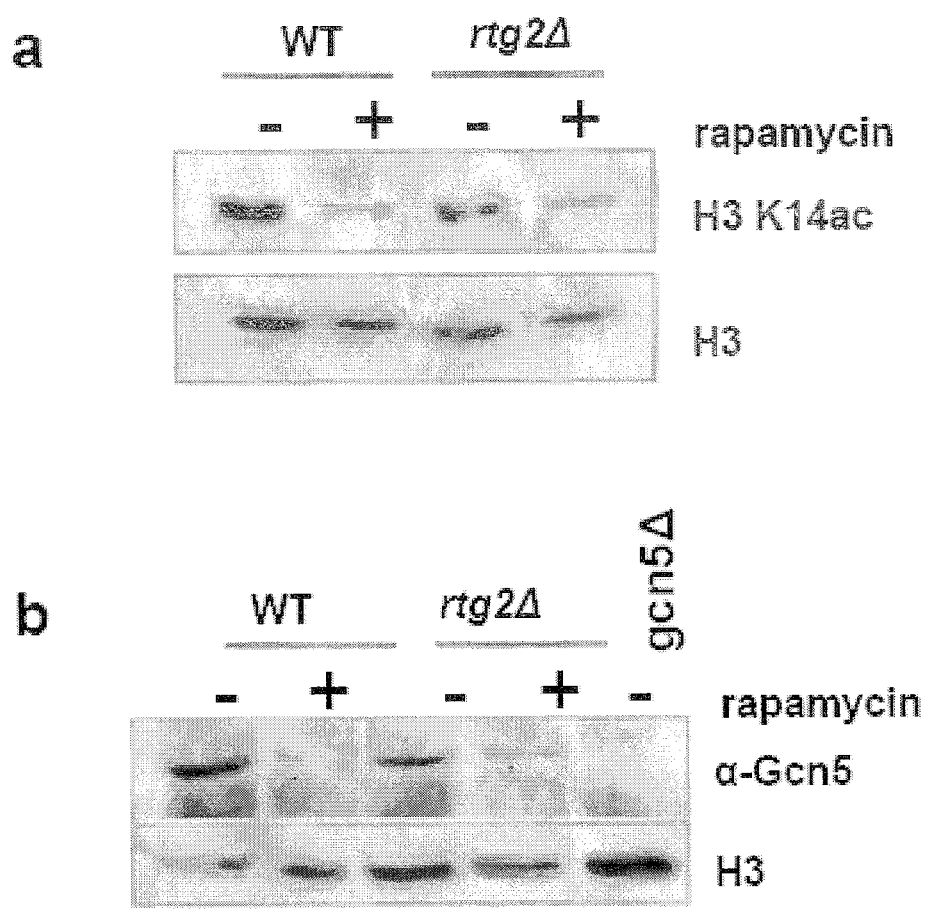

FIG. 11 shows Rtg2 is required for optimal levels of K14ac but K14ac is rapamycin sensitive in a rtg2Δ strain. Western blots showing levels of modifications at H3 (a) and Gcn5 (b) in total cell extracts prepared from the strains indicated in the BY4741 background. Cells were treated +/−10 µM rapamycin for up to 3 hours. Rtg2 is negatively regulated by the Lst8 component of TORC1[66] and this repression is relieved by loss of TORC1 signalling or rapamycin treatment. Rtg2 is a component of SLIK[11] required for the induction of the retrograde responsive genes in quiescent cells.

Figure 12:
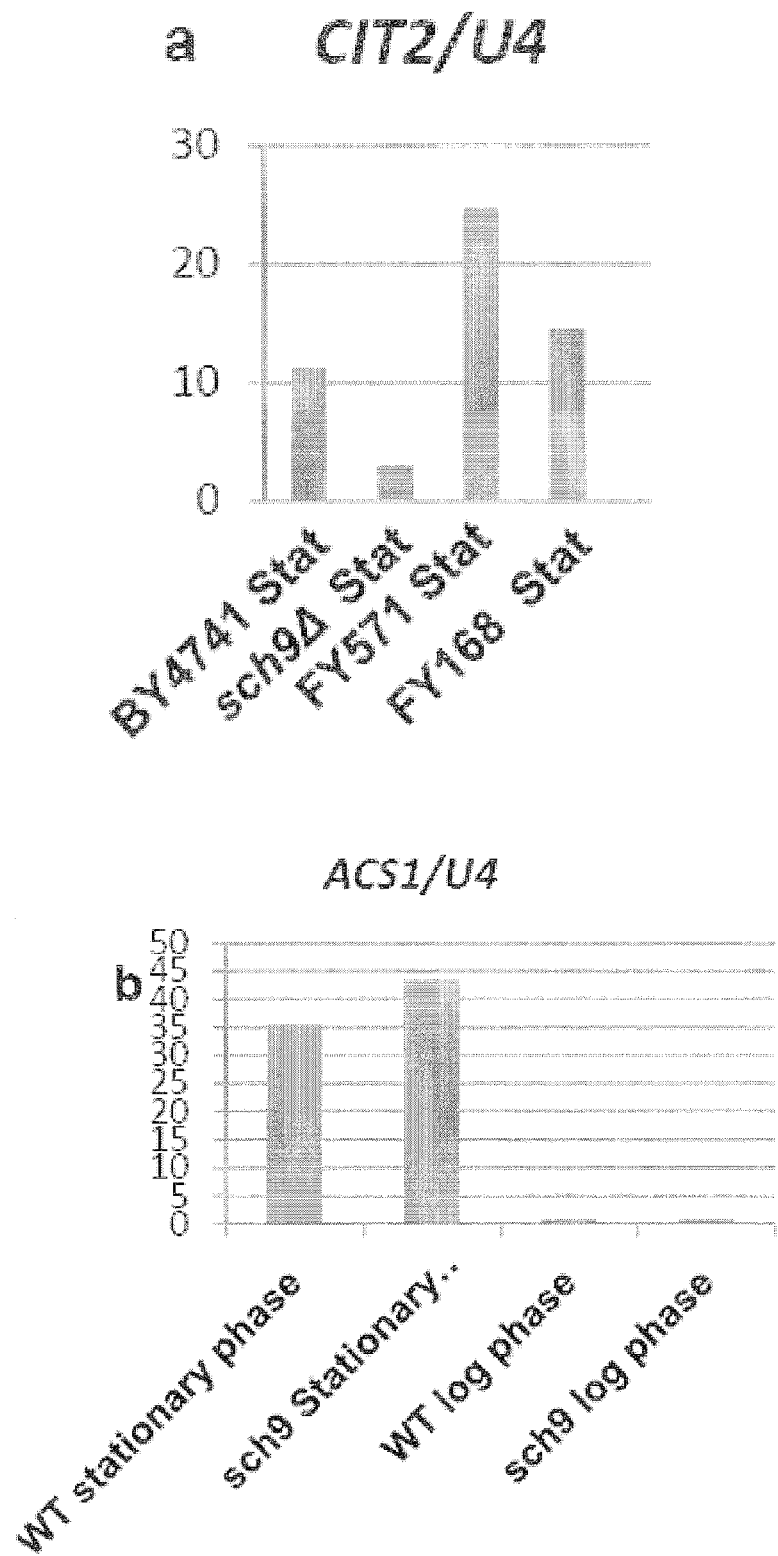
Figure 12:
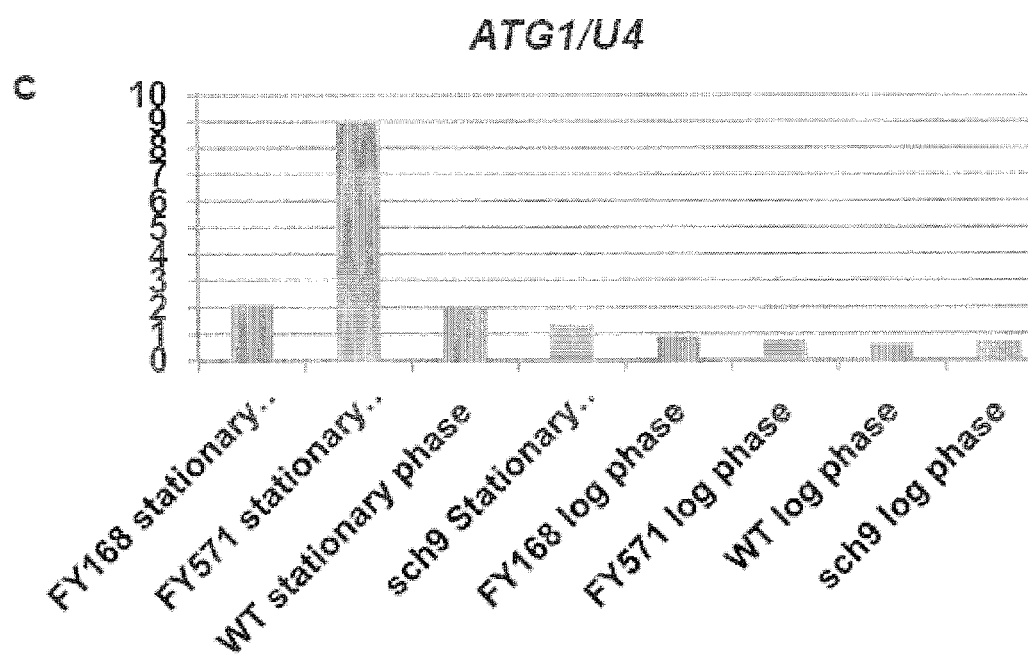

FIG. 12 shows the effect of loss of Sch9 on the inducibility of CIT2, ATG1 and ACS1 in stationary phase. This figure shows reverse transcription real time PCR quantitation of RNA for the genes shown. The results suggest that Sch9 is required to maintain the integrity of SALSA and SLIK in stationary phase cultures. Consistent with this we show that the induction of ACS1 is independent of Sch9 (data in FIG. 9 suggests that this gene is dependent on Rtg2 dependent nuclear uptake of Rtg1/3 but not on SLIK). By contrast, CIT2 (SLIK/Rtg2—dependent) and ATG1 (SALSA but not SLIK dependent) require Sch9 for their expression.

Figure 13:
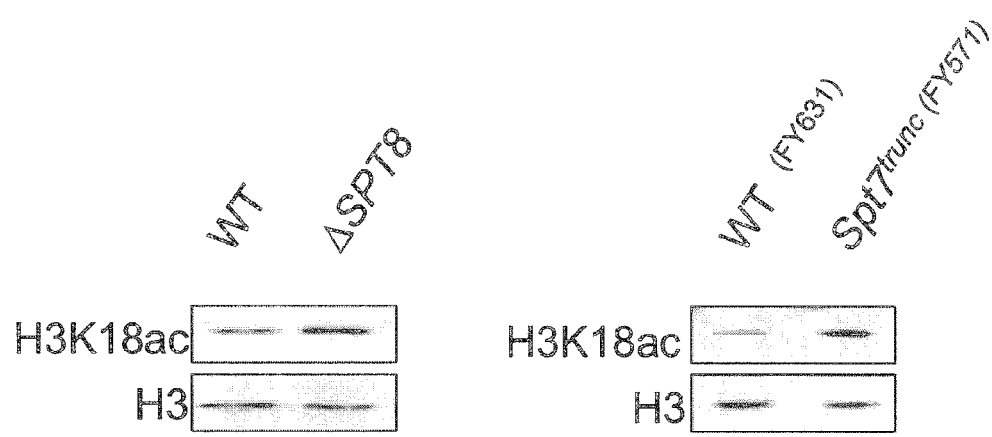

FIG. 13 is a western blot showing that disruption of the SAGA complex results in an increase H3K18 acetylation.

Figure 14:
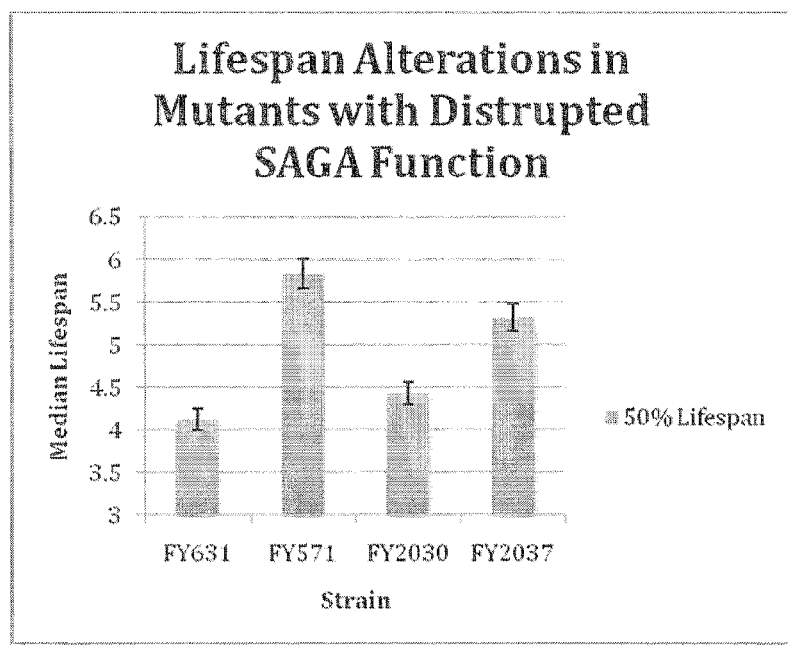

FIG. 14 is a graph showing that disruption of SAGA extends the chronological lifespan of yeast cells.

Figure 15:
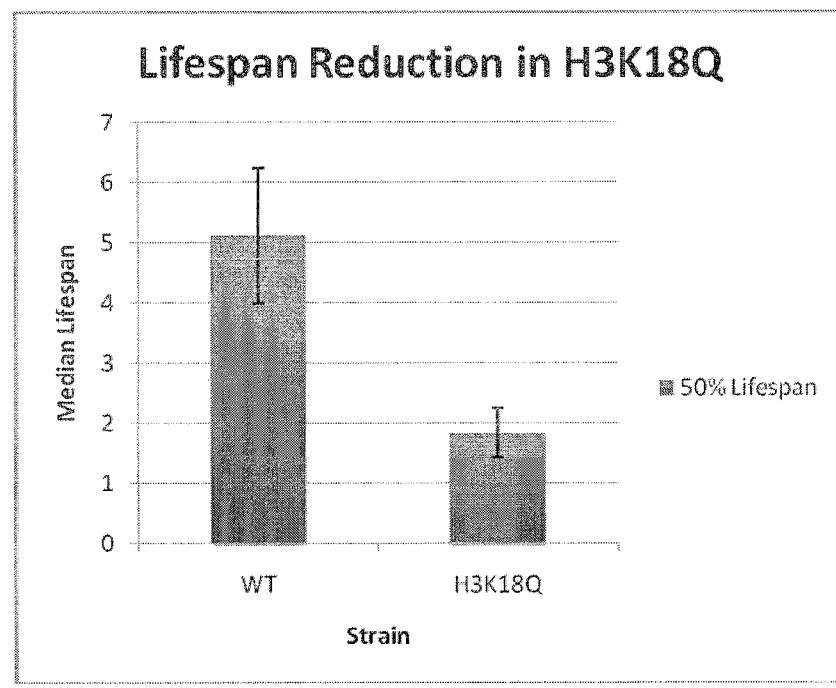

FIG. 15 is a graph showing that disruption of H3K18 acetylation results in a significant reduction in chronological lifespan of yeast cells.

Materials and Methods

Details of strains are provided in the Table 1. Yeast were grown at 30° C. in rich medium (YPD), 1% bactpopeptone, 1% Difco yeast extract (BD and Co.), 2% glucose to a density of $0.4 \times 10^6$ cells/ml and treated with 10 µM rapamycin in 90% ethanol/10% Tween20 or mock treated for up to three hours. Details for preparation of whole cell extracts, western blotting and antibodies used, preparation of RNA and RNA quantitation, chromatin immunoprecipitation (ChIP), protocols for ageing, assessment of ERCs and chronological ageing assays are set out below.

TABLE 1

| Strain | Parent | Genotype | Origin |
|---|---|---|---|
| RMY200 WT | | MATa; ade2-10; 1 his3Δ200; lys2-801; trp1Δ901; ura3-52; hht1, hhf1::LEU2; hht2, hhf2::HIS3 plus pRM200 (CEN TRP1 HHF2 HHT2) | Michael Grunstein |
| H3 K14R | RMY200 | Plus pRM200 (hht2 K14R) | Michael Grunstein |
| H3 K18R | RMY200 | plus pRM200 (hht2 K18R) | Michael Grunstein |
| YSL151 WT | | ura3-5; his3Δ20; leu2Δ; trp1Δ63 lys2-128Δ(hht1-hhf1)::LEU2; (hht2-hhf2)::HIS3; pTRP1-HHT2-HHF2 | Shelley Berger |
| H3 K4A | YSL151 | Plus pTRP1 (hht2 K4A) | Shelley Berger |
| YZS276 | | MATa; hta1-htb1Δ::LEU2 hta2-htb2Δ leu2-3,-112 his3-11,-15 trp1-1 ura3-1 ade2-1 can1-100 (pZS145 HTA1-Flag-HTB1 CEN HIS3) | David Allis |
| H2B K123R | YZS276 | Plus pZS14 (htb1 K123R) | David Allis |
| LPY8056 | | MATa; his3Δ200; leu2Δ1; ura3-52; trp1Δ63; lys2-128δ; (hht1-hhf1)Δ::LEU2 plus pRS314B (HHF2 HHT2) | Shelley Berger |
| H3 S10A | LPY8056 | Plus PRS314B (hhf2 S10A) | Shelley Berger |
| H3 K14A | LPY8056 | Plus PRS314B (hhf2 K14A) | Shelley Berger |
| H3 S10A K14A | LPY8056 | Plus PRS314B (hhf2 S10A K14A) | Shelley Berger |
| BY4741 | | MATa; his3Δ; leu2Δ; met15Δ; ura3 | Euroscarf |
| gcn5Δ | BY4741 | gcn5::KanMX | Euroscarf |
| spp1Δ | BY4741 | spp1::KanMX | Euroscarf |
| S288c | | MATa; his3Δ1; leu2Δ0; met15Δ0; ura3Δ0 | Open Biosystems |
| fpr1Δ | BY4741 | fpr1::KanMX | Euroscarf |
| fpr2Δ | BY4741 | fpr2::KanMX | Euroscarf |
| fpr3Δ | BY4741 | fpr3::KanMX | Euroscarf |
| fpr4Δ | BY4741 | fpr4::KanMX | Euroscarf |
| rim15Δ | BY4741 | rim15::KanMX | Euroscarf |
| rtg2Δ | BY4741 | rtg2::KanMX | Euroscarf |
| msn2Δ | BY4741 | msn2::KanMX | Euroscarf |
| msn4Δ | BY4741 | msn4::KanMX | Euroscarf |
| snf1Δ | BY4741 | snf1::KanMX | Euroscarf |
| sch9Δ | BY4741 | sch9::KanMX | Euroscarf |
| dot1Δ | By4741 | dot1::KanMX | Euroscarf |
| L5487 | | MATa, ura3-52, leu2::hisG | Aaron Mitchel |
| sch9Δ | L5487 | sch9::URA3 | Paul Nutton |
| Gal83-HA | BY4741 | GAL83-HA-His3MX6 | This study |
| Gcn5-HA | JR-52A | Plus pRS314 (GCN5 3HA::his5+) | Shelley Berger |
| spt20Δ | BY4741 | spt20::KanMX | Euroscarf |
| spt8Δ | BY4741 | spt8::KanMX | Euroscarf |
| FY3 | | MATa; ura3Δ0 | Fred Winston |
| FY2030 HA-Spt7 | FY3 | MATa; ura3Δ0; leu2Δ1; trp1Δ63; his4-917 δ; lys2-173R2 HA-SPT7-URA3 | Fred Winston |
| HA-Spt7 snf1Δ | FY2030 | snf1::KanMX | This study |
| HA-Spt7 sch9Δ | FY2030 | sch9::KanMX | This study |
| FY168 | | MATa; leu2Δ1; his4-917 δ; lys2-173R2 | Fred Winston |
| FY168 rtg2Δ | | rtg2::KanMX | This study |
| FY571 spt7-217 | | MATa; ura3Δ0; leu2Δ1; trp1Δ63; his4-917 δ; lys2-173R2 spt7-217 | Fred Winston |
| FY571 rtg2Δ | spt7-217 | rtg2::KanMX | This study |

Preparation of Yeast Whole Cell Extracts.

25 ml of cells were grown in YPD to an OD of ~0.4 $A_{600}$ and harvested by centrifugation. For rapamycin treated cells, cells were grown to mid-log followed by the addition of 10 µM rapamycin (Sigma R0395-1 MG) for up to 3 hours and harvested by centrifugation. Cell pellets were resuspended in 300 µl 8 M urea and broken by vortexing for 5 mins following the addition of 200 µl acid-washed glass beads (Sigma). Lysates were boiled for 5 mins in standard laemmli loading buffer.

Western Blotting.

Protein extracts were subject to electrophoresis on polyacrylamide gels using standard Tris-glycine running buffer (40% (w/v) glycine, 0.25 M Tris-base, 10% (w/v) SDS) following heating at 90° C. for 3 min. Proteins were transferred onto a nitrocellulose membrane using semi-dry transfer (Bio-Rad). Successful transfer of protein was verified by Ponceu S staining (0.1% Ponceu S, 5% acetic acid). Membranes were then blocked in PBS containing 5% dry milk or BSA for 1 hour, followed by incubation with primary antibody: 1:3000 anti-H3 (Abcam ab1791), 1:5000 anti-H3 K9ac (Upstate 07-352), 1:3000 anti-H3 K14ac (Upstate 07-353), 1:5000 anti-H3 K18ac (Upstate 07-354), 1:10,000 anti-H3 K23ac (Upstate 07-355), 1:3000 anti-H3 K27ac (Upstate 07-360), 1:5000 anti-H3 K4me1 (Upstate 07-436), 1:2000 anti-H3 K4me2 (Upstate 07-030), 1:5000 anti-H3 K4me3 (Upstate 07-473), 1:500 anti-Gcn5 (Santa Cruz sc-9078), 1:5000 anti-Tubulin (Abcam ab6160), 1:1000 Anti-HA (Roche clone 3F10 11867423001) in 5% dry milk/PBS/0.5% Tween 20. Membranes were then washed for 6×5 min in PBS and incubated for 1 hour with horseradish peroxidase conjugated secondary antibody in 5% dry milk/PBS/0.5% Tween 20, and washed for 6×5 min in PBS/0.5% Tween 20. Bound antibody was visualised using a Pico West chemiluminescence kit (Pierce Biotechnology Ltd) according to manufacturer's instructions. Multiple exposures of each film were made to ensure signals detected were not saturated. Each experiment was repeated at least 3 times.

RNA Extraction and Northern Blotting.

Extraction of RNA was performed using hot phenol extraction. 15 µg of total RNA was separated on 1.1% formaldehyde gels and transferred to Magna nylon membranes and baked at 80° C. for 2 hours. The membranes were blocked by incubation for 2 hours at 65° C. with PerfectHyb Plus (Sigma). Membranes were typically exposed for 24 hours unless otherwise stated. Levels of total RNA loaded was monitored by the rRNA species, which are equal across samples unless indicated.

Isolation of Yeast at 10 or 20 Generations of Growth.

$1\times10^8$ cells from a culture at $OD_{600}$ of 0.2 were washed in PBS, biotinylated with 3 mg of sulfo-NSH-LC-biotin at room temperature for 15 minutes, washed 6 times with PBS and added to 1 liter of pre-warmed YPD containing 2.5% glucose and incubated for 10 generations. Harvested cells were washed in PBS. 400 ul of strepavidin beads were added and incubated with the cells on ice for 2 hours in PBS. A magnetic sorter was used to select beads with biotinylated cells attached for 20 minutes on ice with occasional mixing. The mixture was washed and reselected five times using PBS. The sorted cells were added to a second liter of prewarmed YPD and grown for an additional 10 generations, sorted and washed exactly as before. Protein or DNA was isolated from the yeast using urea and glass beads (see above) for analysis by Western blotting or by preparing sphaeroplasts and extracting total DNA by phenol chloroform extraction exactly as described[51]. The total DNA extract was separated on a 0.8% agarose gel. DNA was visualized by hybridization to radiolabelled probes.

Labelling Yeast with 35S Methionine.

Exponential cultures in synthetic complete medium with glucose were treated with or without cycloheximide (250 µg/ml in 10 ml of culture), and the incubation was continued for 5 min prior to the 15-min incubation with 100 µCi of

[35S]methionine (PerkinElmer Life Sciences). Total protein was separated on a 10 or 15% SDS-PAGE gel. The gel was then treated with Enlightening (PerkinElmer Life Sciences), dried, and exposed to x-ray film for 40-72 h.

Microscopy.

Cells in exponential growth or after 2.5 days in culture (stationary phase) were incubated with the membrane-potential-sensitive dye 3,3'-dihexyloxacarbocyanine iodide (DiOC6) obtained from Molecular Probes at a concentration of 20 ng/ml for 30 minutes, washed in PBS and visualised using exposure of 1000 ms (exponential cells) or 250 ms (stationary phase cells) the FITC channel on an Olympus IX-81 fluorescence microscope with a 150 W xenon-mercury lamp and an Olympus 150X Plan NeoFluor oil-immersion objective. Brightfield images (DIC) were captures for each field.

Optimizing Conditions for Treating Cells with Rapamycin

Cells in exponential phase of growth were treated with 10 µM rapamycin in 90% ethanol/10% Tween 20 for up to 180 minutes and levels of H3K14ac and histone H3 examined. Alternatively, cells were treated with up to 20 µM rapamycin for 30 minutes. A standard set of conditions were determined and for all work in this paper involved treatment of exponentially growing cells ($0.4 \times 10^7$ cell/ml) for 2 to 3 hours with 10 µM rapamycin.

Assay Showing the Dependency of Post-translational Modifications to histone H3 on the Integrity of Factors Known to Influence Modifications on Histone H3.

Total cell extracts were prepared from LPY8056 cells expressing histone H3 with alanine (A) substitutions at S10 or K14 or both residues, BY4741 carrying deletions of SPP1, encoding a factor required specifically for H3K4me3[52] or DOT1, the methyltransferase for H3K79[53,54], or YZS276 carrying a substitution at H2BK123[55], required for H3K4me2 and H3K4me3. The modifications of lysines on histone H3 were monitored by Western blotting of total cell protein extracts using antibodies specific for each modification.

HA-Spt7 Undergoes C-terminal Processing in Cells Entering Stationary Phase or Treated with Rapamycin.

Strain FY2030, expressing an N-terminally tagged version of Spt7 from the SPT7 locus and FY3, an untagged control were used for these experiments (n=9 for a). a Cells were grown in YDP to mid-log phase, post-diauxic phase or early stationary phase and total protein extracts prepared, subject to western blot using the 3F10 monoclonal antibody to reveal the HA epitope. Positions of the molecular weight markers are shown and a blot developed to reveal histone H3 levels to act as a loading control. Three high molecular weight form of HA-Spt are present, consistent with full length Spt7 in SAGA, a C-terminally truncated form missing approx 200aa found in SLIK and form 3 who function is not known[27,25]. In addition a form that migrates at 50 kDa is also evident in these and other preparations when levels of full length Spt7 drop. b A repeat of the experiment shown above showing more extensive C-terminally truncated version of Spt7 in all three growth conditions. About three of nine experiments show a profile such as this while six show more discrete bands as in a.

Indirect Immunofluoresence

The acetylation/methylation staus of a cell was assessed using indirect immunoflurescence according to the following protocol. 10-50 ml of a fresh mid-log culture of cells per sample was used. Make fresh 30% formaldehyde (3g p-formaldehyde in 5 ml PEM, add 4M NaOH until dissolved and make up to 10 ml with PEM) and add $\frac{1}{10}^{th}$ volume of 30% formaldehyde to the culture with agitation (in conical flask). 30s later add gluteraldehyde solution to a final concentration of 0.2% (w/v). Shake at incubation temp for 90 min. Spin cells 2K 5 min then wash 3× in PBS or PEM (100 mM Pipes pH 6.9; 1 mM EGTA, 1 mM Mg2SO4). Resuspend cells in 10 ml of PEMS (PEM in 1M Sorbitol) and add 500 µl of ICN Yeast Lytic Enzyme (10 µg/ml). Incubate at 37° C. until ~80% of cells are digested (about 15 min). Wash 3× in 10 ml of PEMS. Resuspend in 10 ml of 1% Triton X100 in PEM for 30s. Wash 3× in 10 ml PEM. Roughly assess the volume of the final pellet. Resuspend in 2 ml of PEMBAL (PEM, 0.1M L-lysine, 1% BSA (globulin free), 0.1% Na Azide) and transfer a volume which will give a 20-30 µl pellet upon a subsequent spin to each of 2 Eppendorf tubes. Put on a rotating wheel for 30 min at room temp. Spin for 10 sec. Resuspend in 50 µl of primary antibody in PEMBAL (test suitable dilution) and incubate for 16 hours on rotating wheel. Wash 3× in 1 ml PEMBAL. Resuspend in 1 ml of PEMBAL and rotate on a wheel for 30 min. Resuspend in 50 µl of Goat anti-mouse Texas Red at 20 mg/ml in PEMBAL. Incubate 16 hours on rotating wheel. Wash 3× in PEMBAL. Resuspend pellet in 100 µl PEMBAL and mount on poly L-Lysine coated coverslips. Dry with hairdryer and invert on 1 µg/ml DAPI in 100% glycerol if required. Alternatively use a FITC secondary antibody at 1/200 and incubate for 1 hour at room temperature on a wheel. N.B. cover tubes with foil during incubations with secondary antibody. The cells were then visualised

EXAMPLES

H3K14ac by SAGA Reflects Growth

Figure 5:
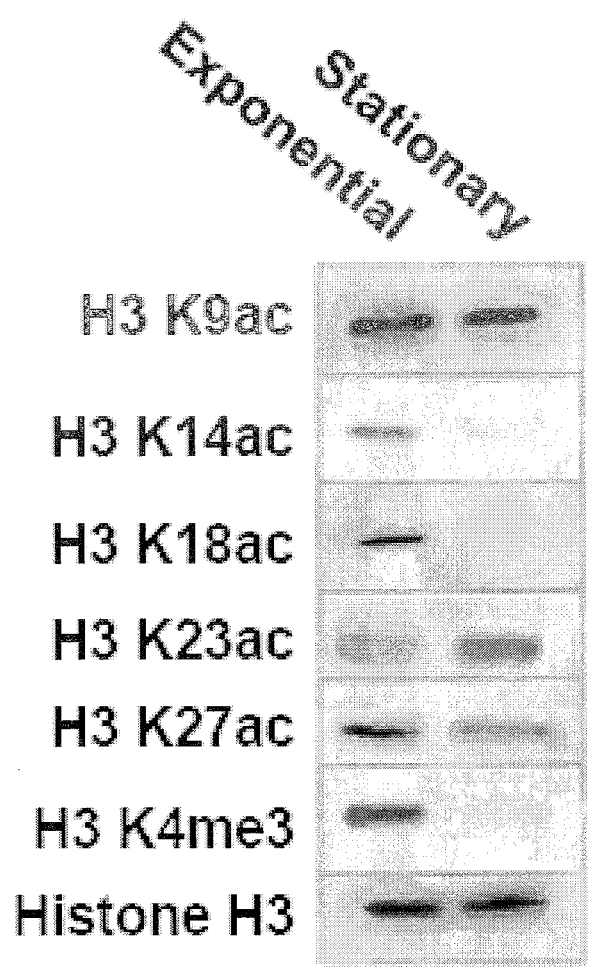

The type of post-translational modification on the histone components of chromatin often reflects whether genes are active or repressed and these changes are globally regulated by enzymes that deposit or remove specific modifications. On active genes, the chromatin is often modified by lysine (K) acetylation (ac) or methylation (me), particularly on histone H3[27]. in order to identify post-translational modifications on histone H3 that reflect cell growth, we prepared total protein extracts from yeast in exponential or early stationary phase. Large and reproducible differences in the signals on Western blots allow us to correlate changes in acetylation and methylation with cell physiology. Cells in stationary phase show reductions in K14ac, K18ac and trimethylation (me3) of K4 that are not a consequence of cell-cycle arrest (FIG. 5). These changes are similar in exponentially growing cells treated with the macrolide rapamycin, which blocks growth and proliferation[14] (FIGS. 1a and 10-11), suggesting that the presence of these modifications reflects the proliferative capacity of the cells.

Figure 1:
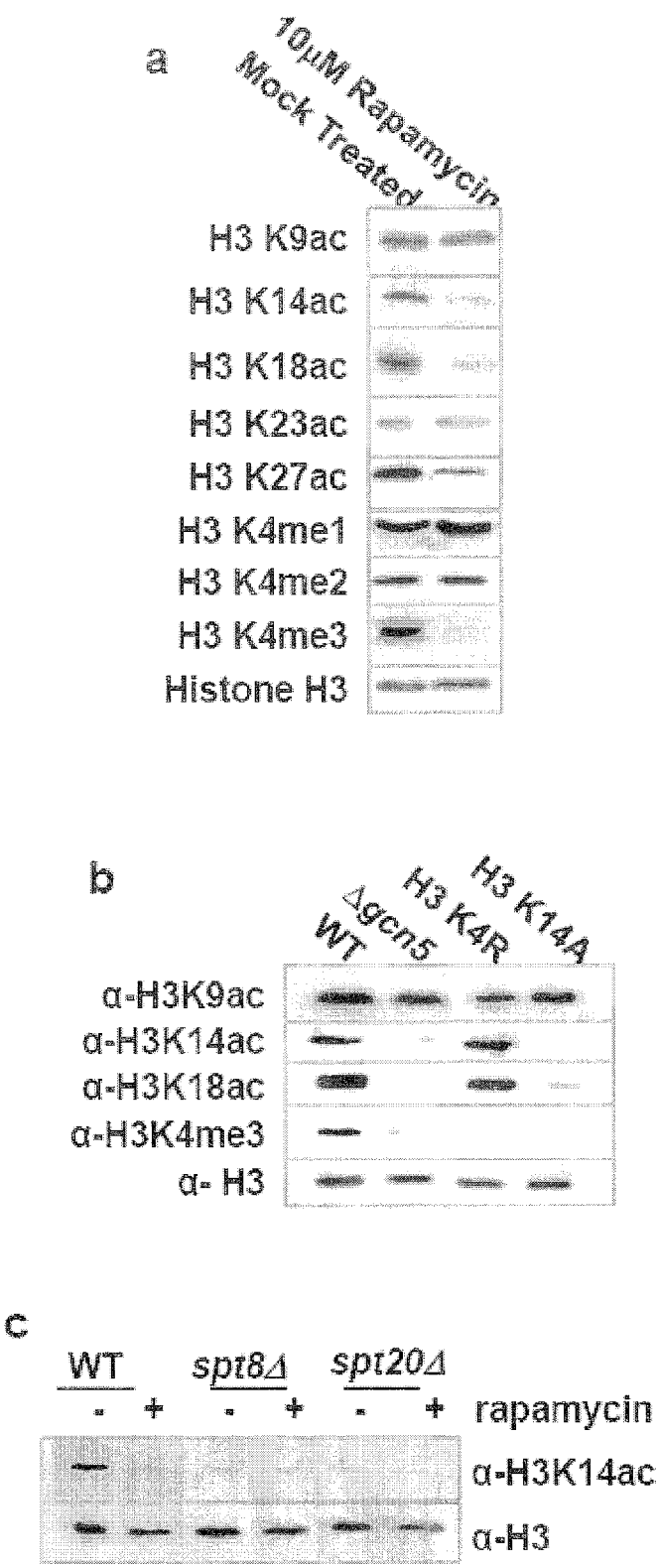
Figure 1:
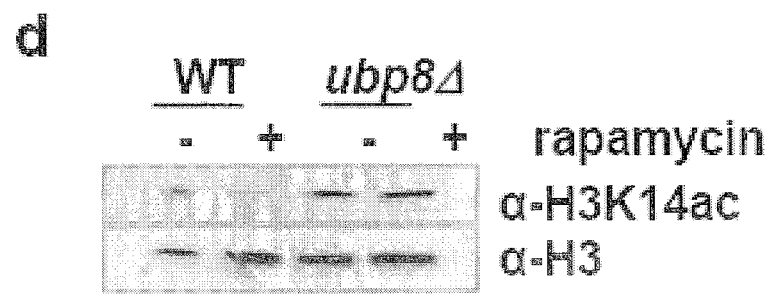
Figure 1:
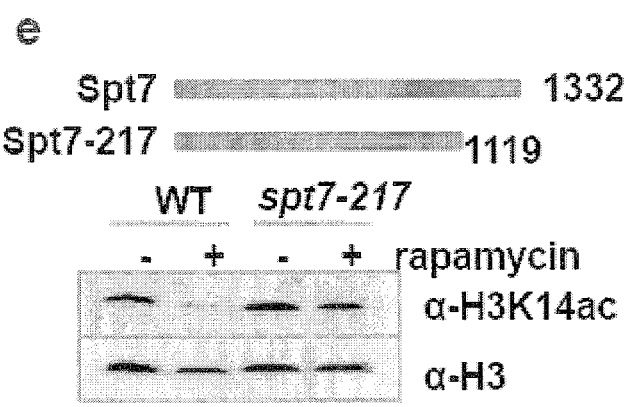
Figure 1:
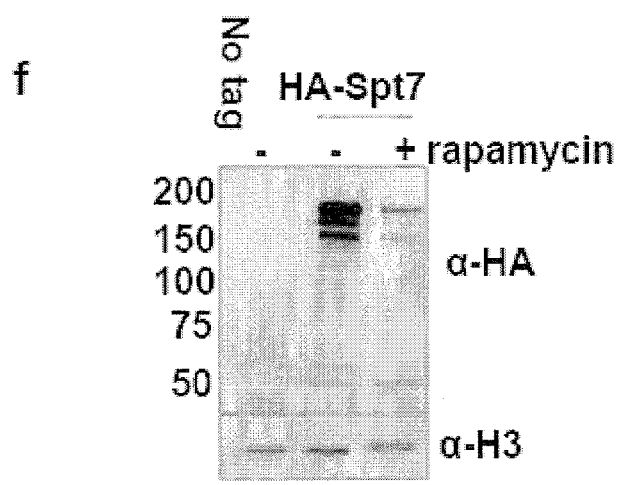
Figure 1:
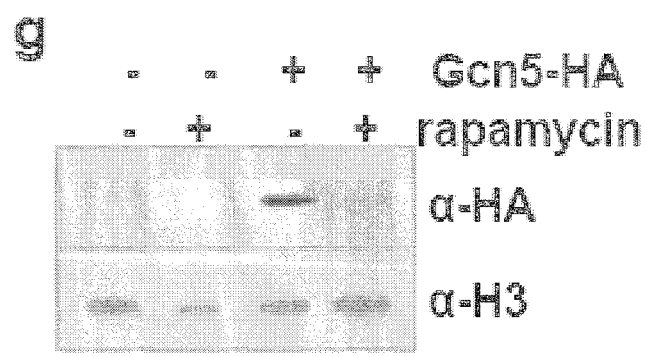
Figure 1:
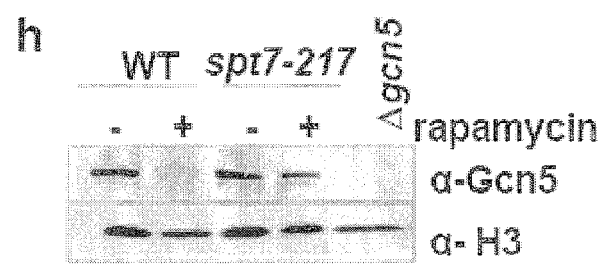
Figure 6:
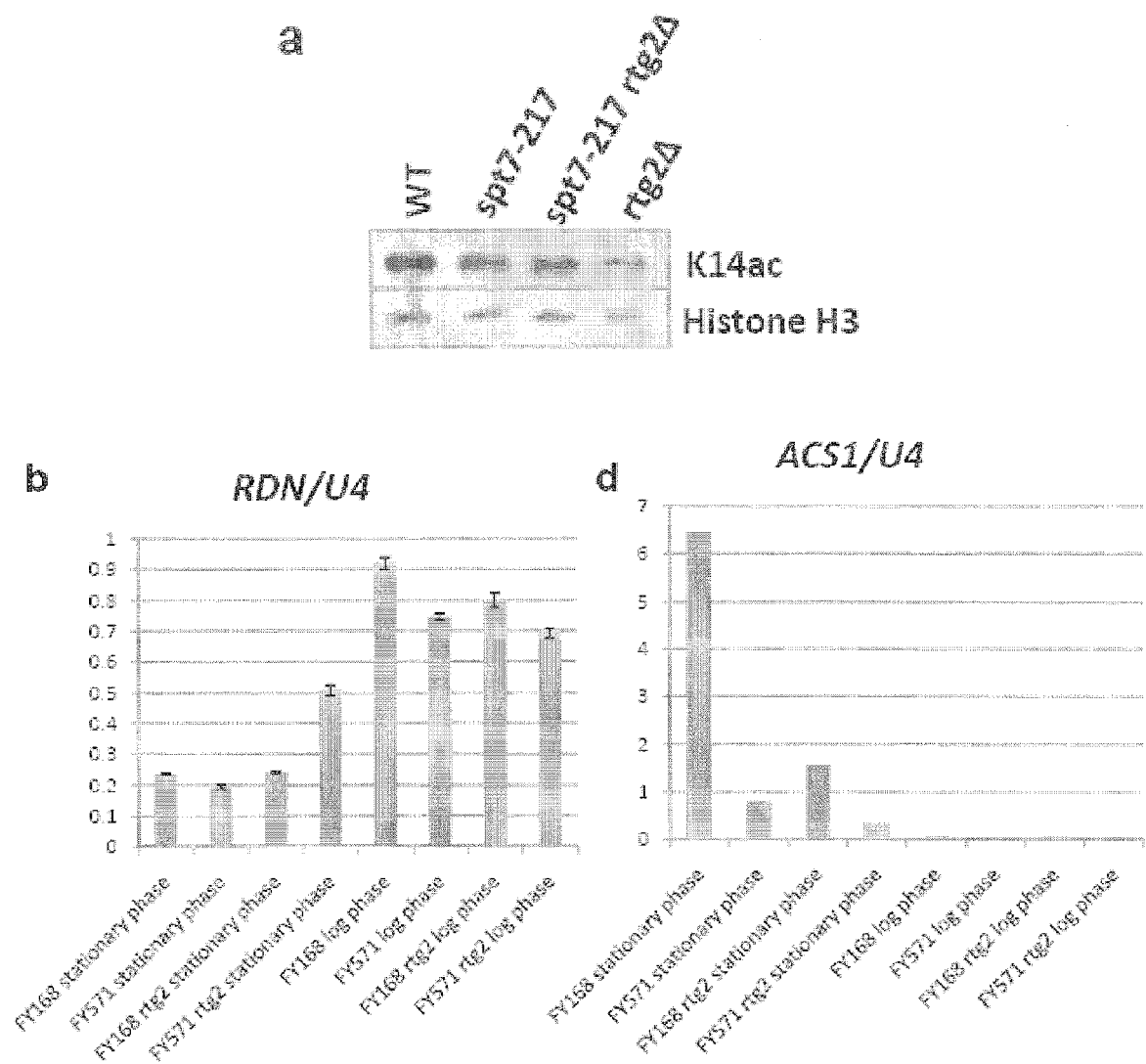
Figure 6:
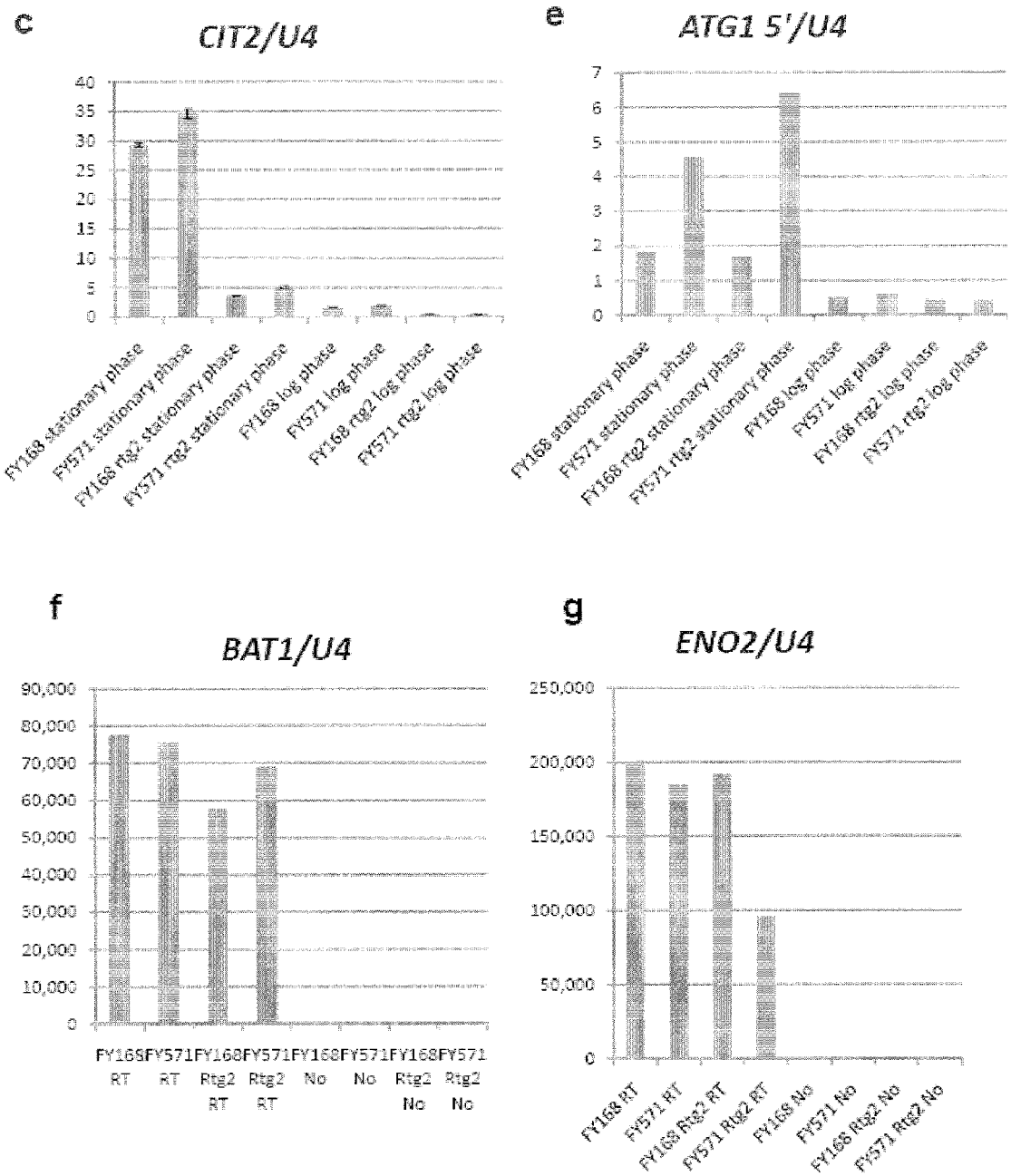
Figure 6:
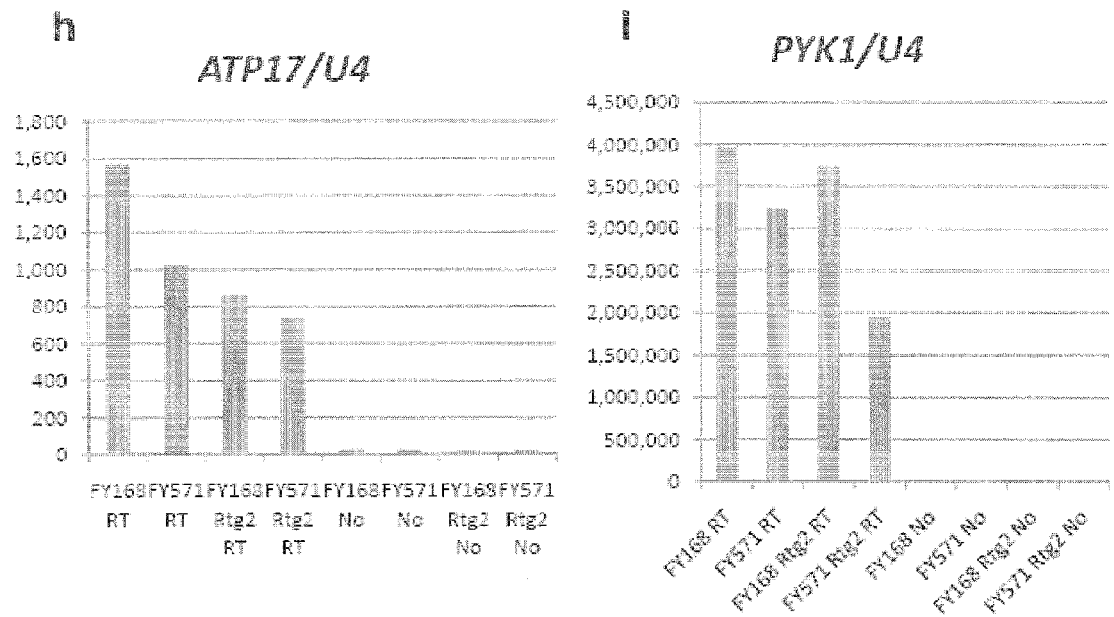

Gcn5 is the major acetyltransferase for K14 and K18 (FIG. 1b). Furthermore, the rapamycin-sensitive K14ac detectable by Western blotting is mediated by Gcn5 in SAGA (FIG. 1c). Strains lacking Spt8, specific to SAGA[22] or Spt20, required for the integrity of SAGA and SLIK/SALSA[23,31,32], have low levels of K14ac that do not detectably change when treated with rapamycin. In contrast, K14ac is resistant to rapamycin in a strain lacking Ubp8, a component of SAGA with ubiquitin protease activity required for processing the C-terminal region of Spt7[23,25] (FIG. 1b). Western blots showing levels of modifications at H3 on total cell extracts prepared from the strains indicated all in the BY4741 background are shown in FIGS. 1c-e. Cells were treated +/−10 µM rapamycin for up to 3 hours. A strain expressing Spt7 lacking the C-terminal 213aa, known as Spt7-217[33] also shows rapamycin resistant K14ac, suggesting that SLIK and SALSA are resistant to rapamycin (FIG. 1e). It is important to note that in this strain, the truncated Spt7 is expressed at levels similar to full length Spt7[33], hence the high levels of K14ac. Levels of truncated Spt7 in SLIK and SALSA are normally much lower than full length Spt7 and make a minimal contribution to global levels of K14ac[22,23,25]. Moreover, this resistance to rapamycin is consistent with roles in the activated, but not basal, expression of TATA box genes[34] that function to promote growth when glucose is depleted[18,21] (FIG. 6). Furthermore, this implicates the C-terminal 213aa of Spt7 in the rapamycin sensitivity of K14ac by SAGA as Spt8, a SAGA specific subunit, is recruited through this region[22,23]. Thus rapamycin may have differential effects on SAGA and SLIK/SALSA. SAGA is active in glucose grown cells while SLIK and SALSA are active in nutrient limited cells when TORC1 signalling is reduced (FIG. 6).

The FY168 WT strain has been engineered to express only Spt7 containing a C-terminal truncation (FY571 Spt7-217) similar to that found naturally in the SLIK/SALSA complex. The Spt7 protein is expressed at similar level to full length Spt7[10]. we investigated levels of K14ac in this strain and the influence of Rtg2, the retrograde regulator and component of SLIK on the activity of this strain. FIG. 6a to shows that the K14ac is not significantly reduced in this strain when a deletion of RTG2 is introduced. Rtg2 is required for the H3 directed HAT activity of the SLIK complex[11]. This may reflect the naturally low levels of SLIK in cells compared to this complex. In addition we tested transcriptional responses (using reverse transcription coupled to real time PCR using primers to the loci indicated; No indicates reaction with no RTase added to reaction to control for DNA contamination) in this strain in exponential growth (log) and in early stationary phase (Stat or SP). Levels of transcript were normalised to U4snRNA. Levels of this transcript drop by half in stationary phase cells (data not shown). b Levels of RDNA transcription, monitored using a primer set to the intergenic region between the 25S and 18S regions, are reduced over 7 fold in stationary phase. c The retrograde responsive gene CIT2[12] is induced in the stationary phase cells and is dependent on Rtg2 in the WT Spt7(FY168) and Spt7-217 (FY571)backgrounds, as expected. d Induction of ACS1, encoding mitochondrial acetyl CoA synthase is induced in stationary phase and is Rtg2-dependent. In cells containing high levels of the SLIK/SALSA complex the gene is not induced. SLIK/SALSA may repress ACS1 expression or alternatively, the high levels of SLIK/SALSA may sequester Rtg2 creating an RTG2 null. e The induction of ATG1, a regulator of the autophagy[13], another starvation induced response, shows no dependence on Rtg2. Instead, the strains expressing Spt7-217 show a more than two fold increase in ATG1 mRNA levels under starvation conditions suggesting a role for the SALSA complex. The patterns of expression of these three genes may define how the SLIK/SALSA complexes contribute to gene regulation. We propose that ATG1 is dependent on SALSA and independent of SLIK and Rtg2. By contrast, CIT2 requires the SLIK complex for its activation while ACS1 is dependent on Rtg2 but not SLIK (The Rtg2 function to regulate nuclear uptake of Rtg1/3 as activators). Expression at a number of other loci is also monitored (f-i) in log phase. Modifications of lysines on histone H3 are monitored by Western blotting of total protein extracts using antibodies specific to the modification or protein indicated. n=2 for each experiment. Total protein and RNA were prepared from the same cultures for the experiment shown.

Figure 7:
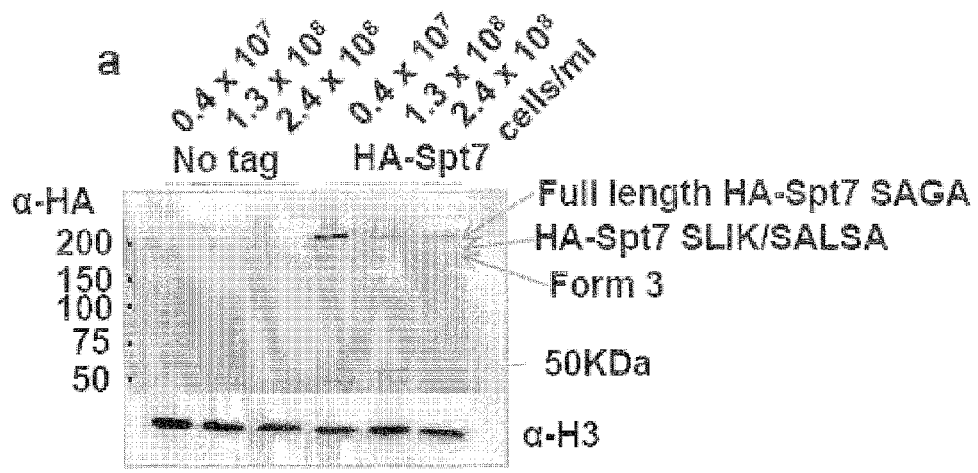
FIG. 7 shows HA-Spt7 undergoes C-terminal processing in cells entering stationary phase.

We used an N-terminally HA tagged version of Spt7 to examine its levels and integrity in rapamycin treated (FIG. 1f) or stationary phase cells (FIG. 7). Reduced levels and C-terminal truncation of Spt7 occurs in both conditions and, by compromising the integrity of SAGA[23], explains the reduced K14ac. Thus the integrity of SAGA is controlled by C-terminal truncation of Spt7 that occurs when cells enter stationary phase or on rapamycin treatment. Levels of Gcn5, but not its RNA[18], also drop significantly in rapamycin treated WT cells (FIG. 1g). in contrast, Gcn5 levels are higher in rapamycin-treated cells expressing Spt7-217 (FIG. 1h). Thus the reduction in Gcn5 is likely to be a consequence of the C-terminal truncation and reduction in levels of Spt7.

SAGA Decreases with Age in Growing Cells

Figure 2:
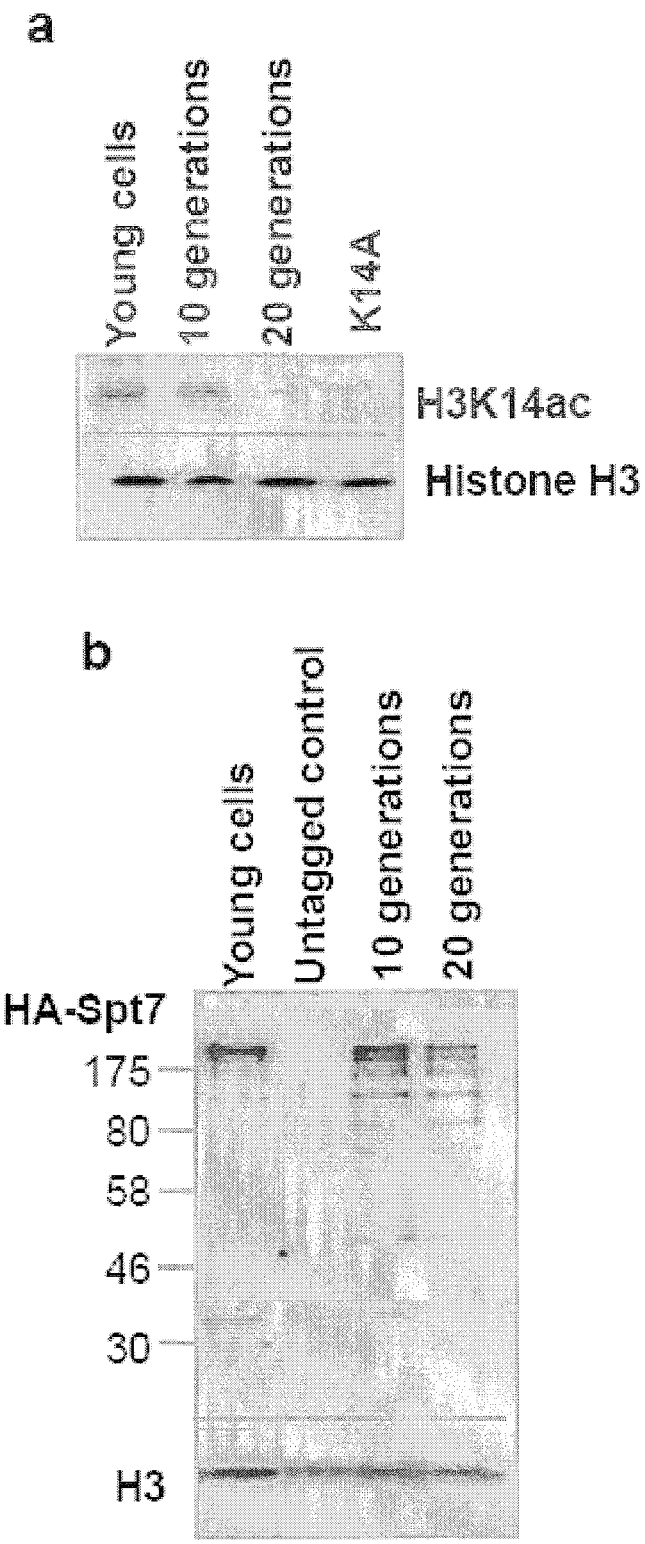
Figure 2:
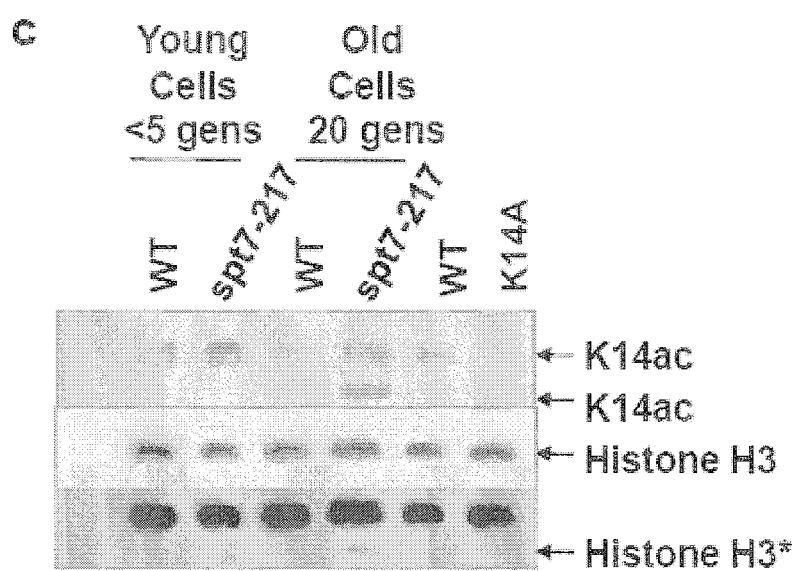
Figure 3:
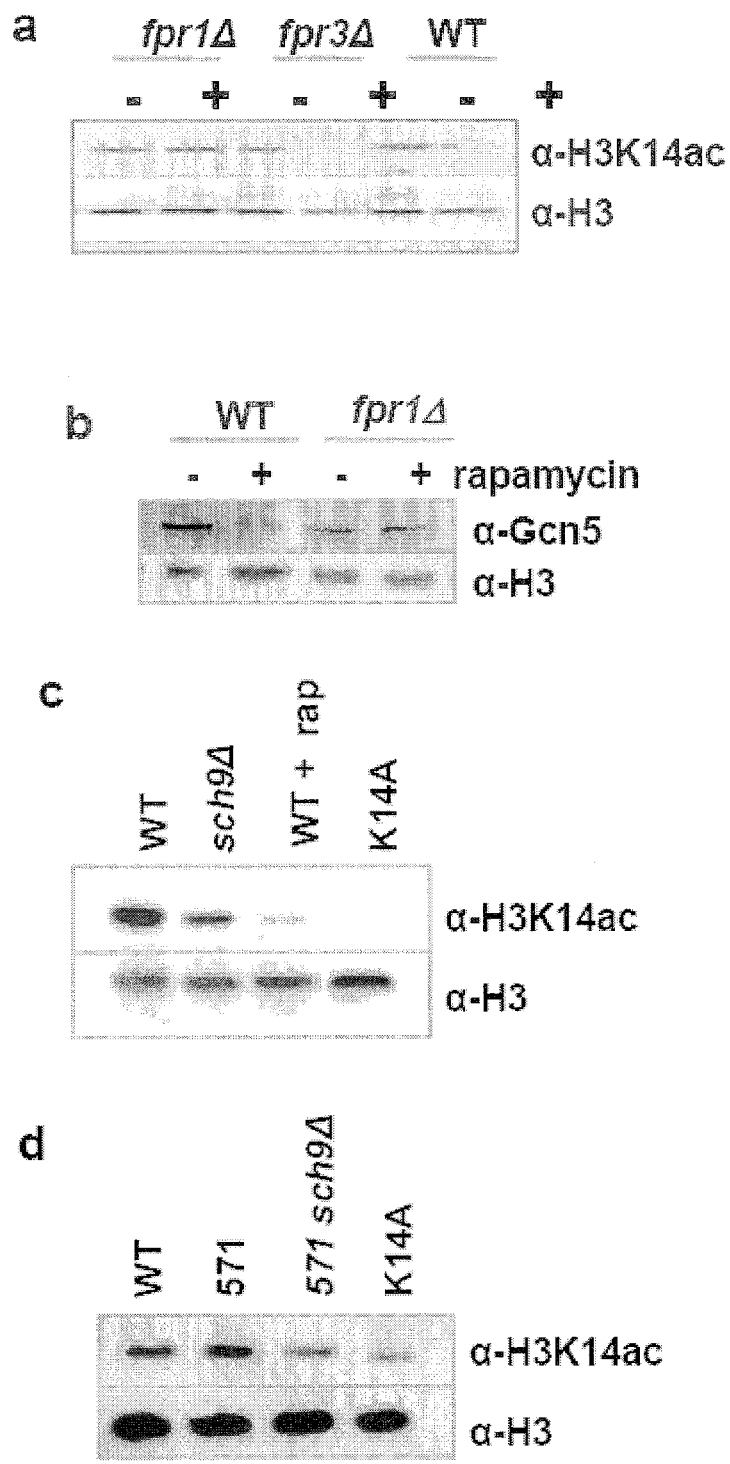
Figure 3:
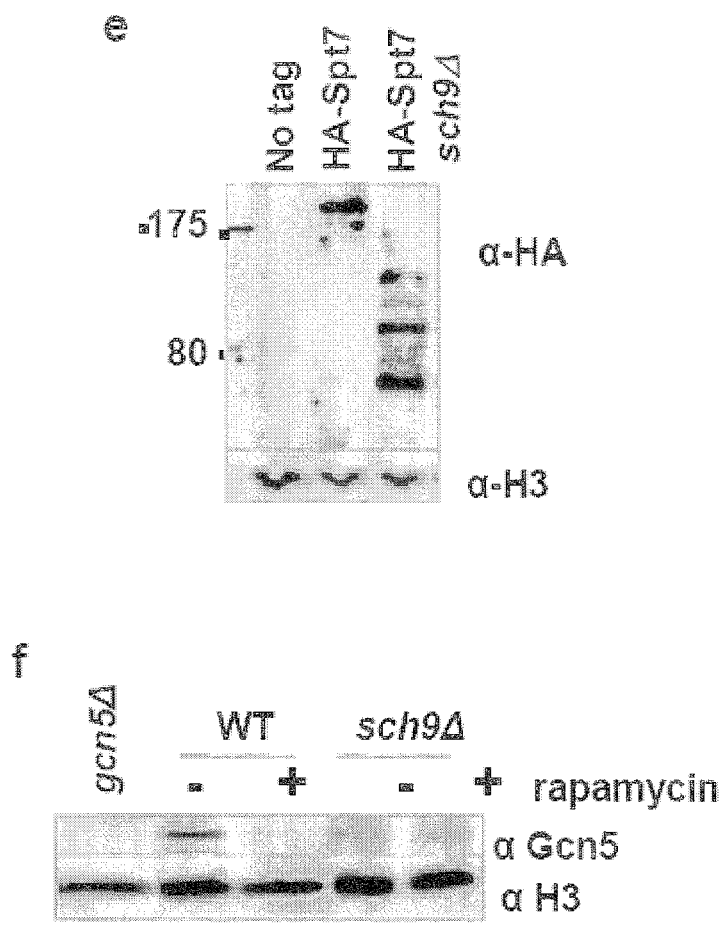
Figure 8:
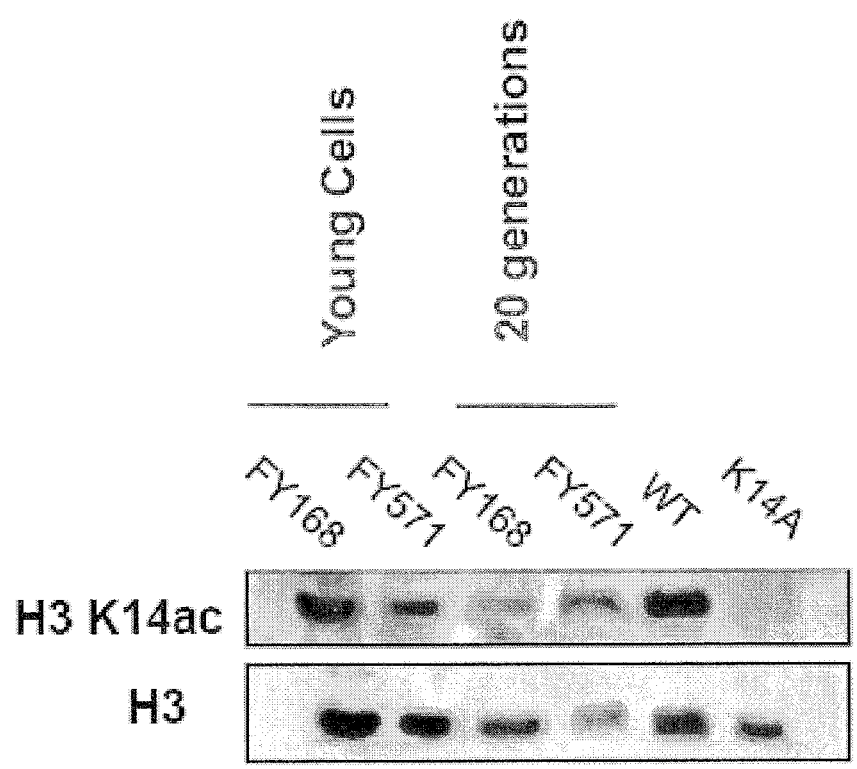
FIG. 8 shows K14ac is reduced as cells age.

The data suggests that SAGA activity is a marker of growth and proliferation. As cells age both proliferative capacity and mitochondrial function are reduced. Experiments were undertaken to assess if SAGA changes during ageing by assessing levels in young cells (generally <5 generations old) compared to cells after 10 or 20 generations of growth. As cells age, levels of K14ac drop (FIG. 2a) and this is associated with an overall decrease in HA-Spt7 levels, in particular a drop in full length HA-Spt7 and increased truncated forms of HA-Spt7 supporting loss of SAGA function during ageing (FIG. 2b). By contrast, in the strain expressing only C-terminally truncated Spt7 (Spt7-217) K14ac does not drop in old cells (FIG. 2c). Total protein preparations were made from young cells or biotinylated cells after 20 generations of growth in exponential phase in rich medium, isolated using streptavidin magnetic beads. Western blot of levels of K14ac in total protein extracts prepared from FY168 (WT) and FY571 expressing Spt7-217. Levels of histone H3 were assessed to control for loading. It can be seen from FIG. 8 that there are differences in the amount of protein isolated. Levels of K14ac drop in the old WT strain but not in the strain expressing Spt7-217 suggesting that the C-terminal region of Spt7 is required for the reduction in K14ac and that SAGA is the target of this regulation. Note in this preparation there is less histone "clipping" evident than in other experiments (See FIG. 2a). These cells also contain increased levels of a smaller form of histone H3, possibly clipped[36]. This suggests that the mechanism by which SAGA and K14ac are reduced as cells age is similar to that occurring in rapamycin treated cells and involves processing of the C-terminal region of Spt7.

TORC1 F Maintains K14ac in Growing Cells

Figure 9:
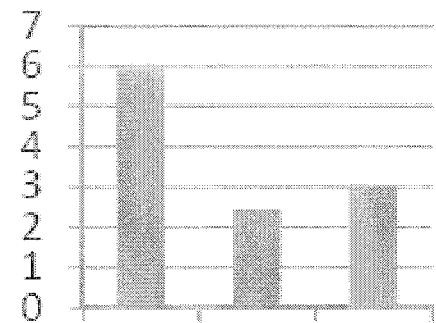
FIG. 9 shows the effect of Rapamycin on K14ac at CIT2 (SLIK induced) or HMS2 (not induced) by ChIP normalised to histone H3. ChIP monitored by real time PCR[53], expressed as a percentage of input and normalised to levels of histone H3 in three preparations of chromatin, at the 5' region of the genes shown.
Figure 9:
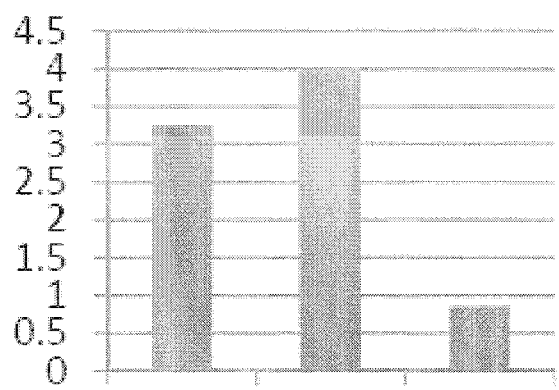

We sought to define how rapamycin influences acetylation by SAGA. There are four targets of rapamycin in yeast, Fpr1-4[37]. In the presence of rapamycin, Fpr1 inhibits functions associated with the PI3-related kinases Tor1 or Tor2 within the TORC1 complex[38]. This supports TORC1-dependent signalling controlling the global levels of K14ac, K18ac and K4me3 by maintaining SAGA function in proliferating cells. inhibition of TORC1 by rapamycin during the early stages of growth results in upregulation of SLIK/SALSA regulated genes that promote efficient respiration of glucose and stress resistance (FIG. 9)[20,39]. As can be seen in FIG. 9b, levels of CIT2 expression, regulated by the TORC-1 complex are increased upon addition of rapamycin.

AMPK is generally considered to negatively regulate mammalian mTOR, resulting in down regulation of TORC1 signalling when glucose becomes scarce and intracellular levels of AMP increase[63]. The yeast AMPK Snf1 as can be seen from FIG. 10 may function in a similar way as it is required for the rapamycin-dependent reduction in K14ac (a). Levels of K14ac in a snf1Δ strain are reduced to about 50% of those in a WT strain, due to Snf1 directed phosphorylation of serine 10 on histone H3 that promotes K14 acetylation by Gcn5[64]. Importantly, K14ac (a) and Gcn5 (b) and some of the HA-Spt7 in the cell (c) are resistant to rapamycin in the snf1Δ strain. Note that track five* is under loaded in c. Note that the integrity of S10 on histone H3, phosphorylated by Snf1, does not influence the rapamycin sensitivity of K14ac although as with the snf1Δ, level of K14ac is reduced in this background (d). We asked is Snf1 is functioning in the nucleus or cytoplasm. Gal83 is required for the nuclear uptake of Snf1[65] and HA tagged-Gal83 moves from the cytoplasm to the nucleus in rapamycin treated cells as demonstrated by indirect immunofluorescence in fixed cells (e). However, the relationship between Gal83 and Snf1 is not straightforward as gal83Δ strains show WT levels of K14ac in untreated cells and some resistance to rapamycin (f). Similar results are observed for Gcn5 protein in the gal83Δ strain (g). Thus it appears that Gal83 is required for the rapamycin dependent reduction in K14ac and Gcn5 suggesting that this is a nuclear function for Snf1.

SLIK Controls CLS Through Rtg2

Figure 4:
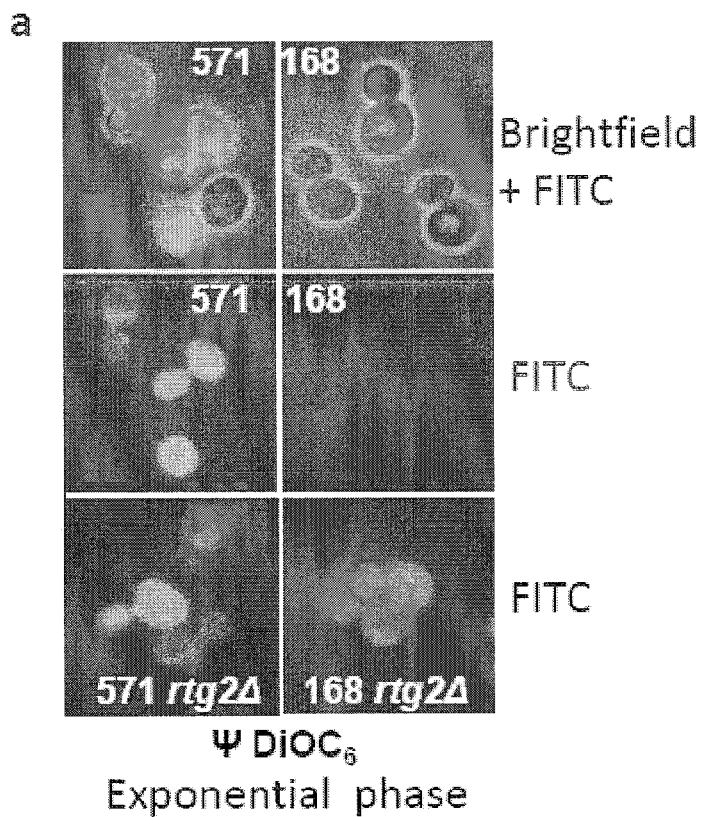
Figure 4:
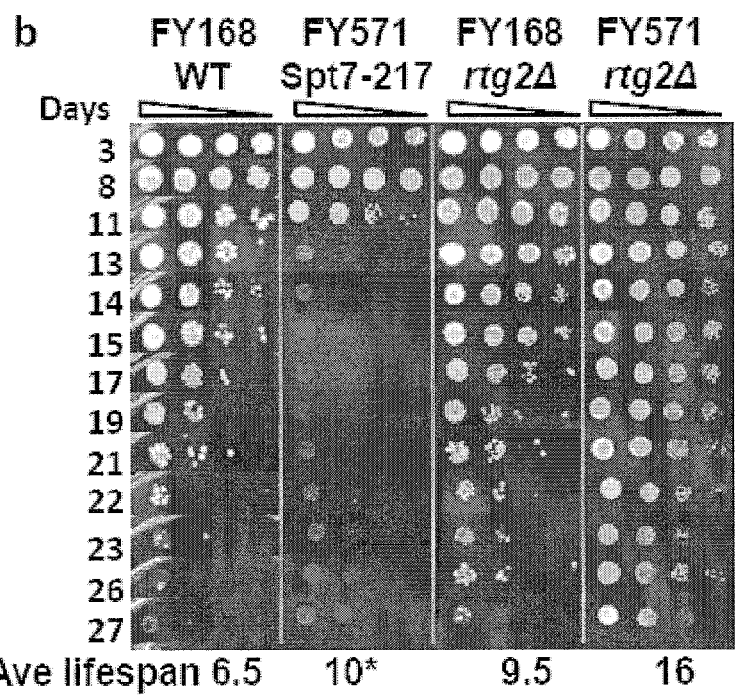
Figure 4:
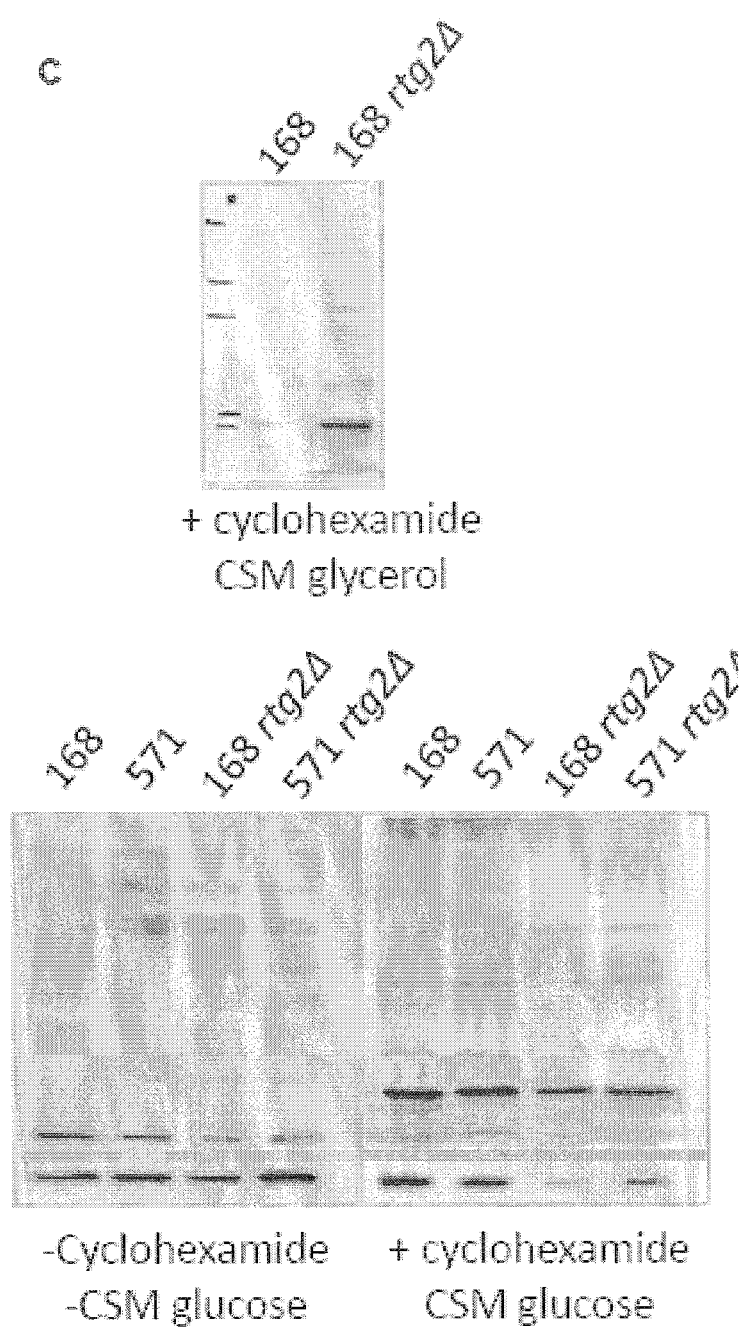

We examined mitochondrial membrane potential ($\psi$) and CLS in the strain expressing only truncated Spt7 (Spt7-217), and thus expressing high levels of SLIK/SALSA complexes during exponential growth. Both $\psi$ (FIG. 4a) and average CLS (FIG. 4b) are increased compared to WT but the strain then appears to undergo a rapid and complete loss of viability around day 12 in culture that may reflect imbalances in patterns of gene expression. Rtg2 is repressed by the TORC1 complex[26] and has at least two distinct functions, one as a regulator of retrograde response, and a second as a component of SLIK[13]. The high levels of truncated Spt7 might result in sequestration of Rtg2 into a SLIK complex, resulting in an rtg2 null for other functions. In support of this, an rtg2 strain shows increase $\psi$ in exponential phase (FIG. 4a), increased mitochondrial protein synthesis (FIG. 4c) and enhanced CLS (FIG. 4b). This suggests that Rtg2 functions to repress mitochondrial function when TORC1 is active and that the formation of SLIK is linked to reduced TORC1 signalling, leading to truncation of Spt7 and relief of Rtg2-dependent repression of respiration. This provides an additional way to extend CLS. Interestingly, both Spt7 and Rtg2 are reported to be mitochondrially associated proteins[13,47]. Finally, we show that the most marked increase in CLS is observed when RTG2 is knocked out of FY571(Spt7-217) (FIG. 4b), perhaps reflecting strong induction of genes for autophagy, known to prolong lifespan, by SALSA, as this is Rtg2 independent. It should be noted that this rtgΔ phenotype can also be produced by the addition of inhibitors of mitochondrial respiration.

In summary, we show that the SAGA family of transcriptional regulators control the balance between growth and chronological lifespan. Metabolic changes resulting in up- or down-regulation of respiration are differentially controlled by TORC1 and Sch9 signalling to these complexes. TORC1 coordinates mitochondrial function with gene expression through the activities of Spt7 and Rtg2 and the chromatin modification at K14 on histone H3, providing a TORC1 signalling to SAGA and SLIK highly efficient mechanism by which cells switch fate in order to control the balance between growth and longevity.

Disruption of SAGA Results in Increased H3K18 Acetylation and an Extension in Chronological Lifespan.

FIG. 13 is a western blot showing the increase in H3K18 acetylation in strains in which the SAGA complex has been disrupted. As can be seen in the top rows of both panels, the amount of H3K18ac present in whole cell yeast extracts in stains in which the SAGA complex has been disrupted are increased compared to wildtype. The strains used in these experiments were either ΔSPT8 or Spt7 truncated.

FIG. 14 shows that S. cerevisiae strains having a disrupted SAGA complex have an increased chronological lifespan. As show in the figure strains FY631 and FY2030 are wild type, strain FY571 expresses a truncated Spt7 protein which lacks the SAGA specific Spt7 region, strain FY2037 is ΔSPT8 (Wu, P.Y. and Winston, F., Mol Cell Biol., 22(15), p5367-5379).

Lifespan was determined as described in Murakami, C. and Kaeberlein, M., (2009) J. Vis. Exp., 27. Briefly, chronological lifespan of yeast refers to the profile of viability of an ageing yeast culture over time. A yeast culture is grown in liquid media until the glucose carbon source is exhausted and the cells stop dividing. At this point the proportion of cells which are alive and able to divide is measured by observing the outgrowth characteristics of a fresh inoculate of the aging culture using a Bioscreen C machine. Viabilities at various time points are compared to determine the chronological lifespan of the culture.

FIG. 15 shows that in a H3K18Q mutant in which acetylation at this position is disrupted chronological lifespan, as measured using the method above, is reduced compared to wild type. In the H3K18Q yeast strain, both endogenous copies of the H3 gene have been deleted and replaced by a single copy of the H3 gene containing a substitution of lysine 18 with glutamine. In the wild type strain shown in the figure, the deleted H3 genes have been replaced with a single wild type copy of the gene.

All publications mentioned in the above specification are herein incorporated by reference in their entirety. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be with in the scope of the following claims.

References

1 De Virgilio, C. & Loewith, R., Cell growth control: little eukaryotes make big contributions. *Oncogene* 25, 6392-6415 (2006).

2 Martin, D. E. & Hall, M. N., The expanding TOR signaling network. *Curr Opin Cell Biol* 17, 158-166 (2005).

3 Rohde, J. R., Bastidas, R., Puria, R. & Cardenas, M. E., Nutritional control via Tor signaling in Saccharomyces cerevisiae. *Curr Opin Microbiol* 11, 153-160 (2008).

4 Ljungdahl, P. O., Amino-acid-induced signalling via the SPS-sensing pathway in yeast. *Biochem Soc Trans* 37, 242-247 (2009).

5 Wullschleger, S., Loewith, R. & Hall, M. N., TOR signaling in growth and metabolism. *Cell* 124, 471-484 (2006).

6 Bonawitz, N. D., Chatenay-Lapointe, M., Pan, Y. & Shadel, G. S., Reduced TOR signaling extends chronological life span via increased respiration and upregulation of mitochondrial gene expression. *Cell metabolism* 5, 265-277 (2007).

7 Fabrizio, P., Pozza, F., Pletcher, S. D., Gendron, C. M. & Longo, V. D., Regulation of Longevity and Stress Resistance by Sch9 in Yeast. *Science* 292, 288-290 (2001).

Powers, R. W., 3rd, Kaeberlein, M., Caldwell, S. D., Kennedy, B. K. & Fields, S., Extension of chronological life span in yeast by decreased TOR pathway signaling. *Genes Dev* 20, 174-184 (2006).

9 Kaeberlein, M. et al., Increased life span due to calorie restriction in respiratory-deficient yeast. *PLoS Genet* 1, e69 (2005).

10 Lavoie, H. & Whiteway, M., Increased respiration in the sch9Delta mutant is required for increasing chronological life span but not replicative life span. *Eukaryot Cell* 7, 1127-1135 (2008).

11 Medvedik, O., Lamming, D. W., Kim, K. D. & Sinclair, D. A., MSN2 and MSN4 link calorie restriction and TOR to sirtuin-mediated lifespan extension in Saccharomyces cerevisiae. *PLoS Biol* 5, e261 (2007).

12 Kim, D. H. et al., mTOR interacts with raptor to form a nutrient-sensitive complex that signals to the cell growth machinery. *Cell* 110, 163-175 (2002).

13 Liu, Z. & Butow, R. A., Mitochondrial retrograde signaling. *Annu Rev Genet* 40, 159-185 (2006).

14 Kunz, J. & Hall, M. N., Cyclosporin A, FK506 and rapamycin: more than just immunosuppression. *Trends Biochem Sci* 18, 334-338 (1993).

15 Heitman, J., Movva, N. R. & Hall, M. N., Targets for cell cycle arrest by the immunosuppressant rapamycin in yeast. *Science* 253, 905-909 (1991).

16 Peterson, R. T., Beal, P. A., Comb, M. J. & Schreiber, S. L., FKBP12-rapamycin-associated protein (FRAP) autophosphorylates at serine 2481 under translationally repressive conditions. *J Biol Chem* 275, 7416-7423 (2000).

17 Cheng, C., Fabrizio, P., Ge, H., Longo, V. D. & Li, L. M., Inference of transcription modification in long-live yeast strains from their expression profiles. *BMC Genomics* 8, 219 (2007).

18 Smets, B. et al., Genome-wide expression analysis reveals TORC1-dependent and -independent functions of Sch9. *FEMS Yeast Res* 8, 1276-1288 (2008).

19 Baker, S. P. & Grant, P. A., The SAGA continues: expanding the cellular role of a transcriptional co-activator complex. *Oncogene* 26, 5329-5340 (2007).

20 Biddick, R. K., Law, G. L., Chin, K. K. & Young, E. T., The transcriptional coactivators SAGA, SWI/SNF, and mediator make distinct contributions to activation of glucose-repressed genes. *J Biol Chem* 283, 33101-33109 (2008).

21 Pray-Grant, M. G. et al., The novel SLIK histone acetyltransferase complex functions in the yeast retrograde response pathway. *Mol Cell Biol* 22, 8774-8786 (2002).

22 Sterner, D. E., Belotserkovskaya, R. & Berger, S. L., SALSA, a variant of yeast SAGA, contains truncated Spt7, which correlates with activated transcription. *Proc Natl Acad Sci USA* 99, 11622-11627 (2002).

23 Wu, P. Y. & Winston, F., Analysis of Spt7 function in the Saccharomyces cerevisiae SAGA coactivator complex. *Mol Cell Biol* 22, 5367-5379 (2002).

24 Belotserkovskaya, R. et al., Inhibition of TATA-binding protein function by SAGA subunits Spt3 and Spt8 at Gcn4-activated promoters. *Mol Cell Biol* 20, 634-647 (2000).

25 Hoke, S. M., Liang, G., Mutiu, A. I., Genereaux, J. & Brandl, C. J., C-terminal processing of yeast Spt7 occurs in the absence of functional SAGA complex. *BMC Biochem* 8, 16 (2007).

26 Giannattasio, S., Liu, Z., Thornton, J. & Butow, R. A., Retrograde response to mitochondrial dysfunction is separable from TOR1/2 regulation of retrograde gene expression. *J Biol Chem* 280, 42528-42535 (2005).

27 Berger, S. L., The complex language of chromatin regulation during transcription. *Nature* 447, 407-412 (2007).

28 Nakanishi, S. at al., A comprehensive library of histone mutants identifies nucleosomal residues required for H3K4 methylation. *Nat Struct Mol Biol* 15, 881-888 (2008).

29 Martin, D. G., Grimes, D. E., Baetz, K. & Howe, L., Methylation of histone H3 mediates the association of the NuA3 histone acetyltransferase with chromatin. *Mol Cell Biol* 26, 3018-3028 (2006).

30 Taverna, S. D. et al., Yng1 PHD finger binding to H3 trimethylated at K4 promotes NuA3 HAT activity at K14 of H3 and transcription at a subset of targeted ORFs. *Mol Cell* 24, 785-796 (2006).

31 Grant, P. A. et al., Yeast Gcn5 functions in two multisubunit complexes to acetylate nucleosomal histones: characterization of an Ada complex and the SAGA (Spt/Ada) complex. *Genes Deer* 11, 1640-1650 (1997).

32 Sterner, D. E. at al., Functional organization of the yeast SAGA complex: distinct components involved in structural integrity, nucleosome acetylation, and TATA-binding protein interaction. *Mol Cell Biol* 19, 86-98 (1999).

33 Gansheroff, L. J., Dollard, C., Tan, P. & Winston, F., The Saccharomyces cerevisiae SPT7 gene encodes a very acidic protein important for transcription in vivo. *Genetics* 139, 523-536 (1995).

34 Huisinga, K. L. & Pugh, B. F., A genome-wide housekeeping role for TFIID and a highly regulated stress-related role for SAGA in Saccharomyces cerevisiae. *Mol Cell* 13, 573-585 (2004).

35 Santos-Rosa, H. et al., Histone H3 tail clipping regulates gene expression. *Nat Struct Mol Biol* 16, 17-22 (2009).

36 Dolinski, K., Muir, S., Cardenas, M. & Heitman, J., All cyclophilins and FK506 binding proteins are, individually and collectively, dispensable for viability in Saccharomyces cerevisiae. *Proc Natl Acad Sci USA* 94, 13093-13098 (1997).

37 Lorenz, M. C. & Heitman, J., TOR mutations confer rapamycin resistance by preventing interaction with FKBP12-rapamycin. *J Biol Chem* 270, 27531-27537 (1995).

38 Yorimitsu, T., Zaman, S., Broach, J. R. & Klionsky, D. J., Protein kinase A and Sch9 cooperatively regulate induction of autophagy in Saccharomyces cerevisiae. *Mol Biol Cell* 18, 4180-4189 (2007).

39 Urban, J. et al., Sch9 is a major target of TORC1 in Saccharomyces cerevisiae. *Mol Cell* 26, 663-674 (2007).

40 Wei, M. at al., Tor1/Sch9-regulated carbon source substitution is as effective as calorie restriction in life span extension. *PLoS Genet* 5, e1000467 (2009).

41 Kaeberlein, M. et al., Regulation of yeast replicative life span by TOR and Sch9 in response to nutrients. *Science* 310, 1193-1196 (2005).

42 Smith, D. L., Jr., McClure, J. M., Matecic, M. & Smith, J. S., Calorie restriction extends the chronological lifespan of Saccharomyces cerevisiae independently of the Sirtuins. *Aging cell* 6, 649-662 (2007).

43 Bonawitz, N. D., Rodeheffer, M. S. & Shadel, G. S., Defective mitochondrial gene expression results in reactive oxygen species-mediated inhibition of respiration and reduction of yeast life span. *Mol Cell Biol* 26, 4818-4829 (2006).

44 Burtner, C. R., Murakami, C. J., Kennedy, B. K. & Kaeberlein, M., A molecular mechanism of chronological aging in yeast. *Cell Cycle* 8, 1256-1270 (2009).

45 Shamji, A. F., Kuruvilla, F. G. & Schreiber, S. L., Partitioning the transcriptional program induced by rapamycin among the effectors of the Tor proteins. *Curr Biol* 10, 1574-1581 (2000).

46 Roosen, J. et al., PKA and Sch9 control a molecular switch important for the proper adaptation to nutrient availability. *Mol Microbiol* 55, 862-880 (2005).

47 Sickmann, A. et al., The proteome of Saccharomyces cerevisiae mitochondria. *Proc Natl Acad Sci USA* 100, 13207-13212 (2003).

48 Vellai, T., Autophagy genes and ageing. *Cell Death Differ* 16, 94-102 (2009).

49. Nagy, Z. & Tora, L., Distinct GCN5/PCAF-containing complexes function as co-activators and are involved in transcription factor and global histone acetylation. *Oncogene* 26, 5341-5357 (2007).
50. Rodgers, J. T., Lerin, C., Gerhart-Hines, Z. & Puigserver, P., Metabolic adaptations through the PGC-1 alpha and SIRT1 pathways. *FEBS Lett* 582, 46-53 (2008).
51. Kent, N. A. & Mellor, J., Chromatin structure snap-shots: rapid nuclease digestion of chromatin in yeast. *Nucleic Acids Res* 23, 3786-3787 (1995).
52. Morillon, A., Karabetsou, N., Nair, A. & Mellor, J., Dynamic lysine methylation on histone H3 defines the regulatory phase of gene transcription. *Mol Cell* 18, 723-734 (2005).
53. Ng, H. H. et al., Lysine methylation within the globular domain of histone H3 by Dot1 is important for telomeric silencing and Sir protein association. *Genes Dev* 16, 1518-1527 (2002).
54. van Leeuwen, F., Gafken, P. R. & Gottschling, D. E., Dot1p modulates silencing in yeast by methylation of the nucleosome core. *Cell* 104, 745-756 (2002).
55. Lee, J. S. et al., H1stone crosstalk between H2B monoubiquitination and H3 methylation mediated by COMPASS. *Cell* 131, 1084-1096 (2007).
56. Saleh, A. et al., TOM1p, a yeast hect-domain protein which mediates transcriptional regulation through the ADA/SAGA coactivator complexes. *J Mol Biol* 282, 933-946 (1998).
57. Duncan, K., Umen, J. G. & Guthrie, C., A putative ubiquitin ligase required for efficient mRNA export differentially affects hnRNP transport. *Curr Biol* 10, 687-696 (2000).
58. Pray-Grant, M. G. et al., The novel SLIK histone acetyltransferase complex functions in the yeast retrograde response pathway. *Mol Cell Biol* 22, 8774-8786 (2002).
59. Scott, R. C., Juhasz, G. & Neufeld, T. P., Direct induction of autophagy by Atg1 inhibits cell growth and induces apoptotic cell death. *Curr Biol* 17, 1-11 (2007).
60. Reinders, A., Burckert, N., Boller, T., Wiemken, A. & De Virgilio, C., *Saccharomyces cerevisiae* cAMP-dependent protein kinase controls entry into stationary phase through the Rim15p protein kinase. *Genes Dev.* 12, 2943-2955 (1998).
61. Fabrizio, P., Pletcher, S. D., Minois, N., Vaupel, J. W. & Longo, V. D., Chronological aging-independent replicative life span regulation by Msn2/Msn4 and Sod2 in *Saccharomyces cerevisiae*. *FEBS Lett* 557, 136-142 (2004).
62. Pedruzzi, I. et al., TOR and PKA signaling pathways converge on the protein kinase Rim15 to control entry into G0. *Mol Cell* 12, 1607-1613 (2003).
63. Hardie, D. G., AMPK and Raptor: matching cell growth to energy supply. *Mol Cell* 30, 263-265 (2008).
64. Lo, W.-S. et al., Snf1—a Histone Kinase That Works in Concert with the Histone Acetyltransferase Gcn5 to Regulate Transcription. *Science* 293, 1142-1146 (2001).
65. Vincent, O., Townley, R., Kuchin, S. & Carlson, M., Subcellular localization of the Snf1 kinase is regulated by specific beta subunits and a novel glucose signaling mechanism. *Genes Dev* 15, 1104-1114 (2001).
66. Giannattasio, S., Liu, Z., Thornton, J. & Butow, R. A., Retrograde response to mitochondrial dysfunction is separable from TOR1/2 regulation of retrograde gene expression. *J Biol Chem* 280, 42528-42535 (2005).
67. Butow, R. A. & Avadhani, N. G., Mitochondrial signaling: the retrograde response. *Mol Cell* 14, 1-15 (2004).
68. Howitz, G. A et al., Adenovirus Small e1a Alters Global Patterns of Historic Modification. *Science,* 321, 5892, 1034-1085 (2008).

Sequence Listing sch9

SEQ ID No: 1

```
  1 MMNFFTSKSS NQDTGFSSQH QHPNGQNNGN NNSSTAGNDN GYPCKLVSSG PCASSNNGAL
 61 FTNFTLQTAT PTTAISQDLY AMGTTGITSE NALFQMKSMN NGISSVNNNN SNTPTIITTS
121 QEETNAGNVH GDTGGNSLQN SEDDNFSSSS TTKCLLSSTS SLSINQREAA AAAYGPDTDI
181 PRGKLEVTII EARDLVTRSK DSQPYVVCTF ESSEFISNGP ESLGAINNNN NNNNNNQHNQ
241 NQHINNNNEN TNPDAASQHH NNNSGWNGSQ LPSIKEHLKK KPLYTHRSSS QLDQLNSCSS
301 VTDPSKRSSN SSSGSSNGPK NDSSHPIWHH KTTFDVLGSH SELDISVYDA AHDHMFLGQV
361 RLYPMIHNLA HASQHQWHSL KPRVIDEVVS GDILIKWTYK QTKKRHYGPQ DFEVLRLLGK
421 GTFGQVYQVK KKDTORIYAM KVLSKKVIVK KNEIAHTIGE RNILVTTASK SSPFIVGLKF
481 SFQTPTDLYL VTDYMSGGEL FWHLQKEGRF SEDRAKFYIA ELVLALEHLH DNDIVYRDLK
541 PENILLDANG NIALCDFGLS KADLKDRTNT FCGTTEYLAP ELLLDETGYT KMVDFWSLGV
601 LIFEMCCGWS PFFAENNQKM YQKIAFGKVK FPRDVLSQEG RSFVKGLLNR NPKHRLGAID
661 DGRELRAHPF FADIDWEALK QKKIPPPFKP HLVSETDTSN FDPEFTTAST SYMNKHQPMM
721 TATPLSPAMQ AKFAGFTFVD ESAIDEHVNN NRKFLQNSYF MEPGSFIPGN PNLPPDEDVI
781 DDDGDEDIND GFNQEKNMNN SHSQMDFDGD QHMDDEFVSG RFEI
```

Sch9
>YHR205W Chr 8

SEQ ID No: 2

```
Atgatgaatttttttacatcaaaatcgtcgaatcaggatactggatttagctctcaacaccaacatccaaatggac
agaacaatggaaacaataatagcagcaccgctggcaacgacaacggatacccatgtaaactggtgtccagtgggcc
ctgcgcttcatcaaataatggtgcccttttacgaattttactttacaaactgcaacgccgaccaccgctattagt
caggacttatatgcaatgggcacaacaggaataacatcagaaaatgcccttttcaaatgaagtcaatgaataatg
gaatatcatcagttaataataacaacagcaacacccctacgattattaccacgtcacaggaagaaactaatgctgg
aaatgtacatggcgataccggtggcaattctttgcaaaattctgaagatgacaacttttctttccagttctaccac
caaatgcttactctcttccacttcttcgctatcaataactaacgagaagcagcagcagctgcttatggtccagat
accgatattcctaggggtaaactagaagttacaataatagaagcacgtgacctagtcactagatcaaaggattcac
agccttatgttgtttgtacttttgagagttcagagttcatttctaatggtcctgagtcactaggcgccattaataa
taacaacaataacaacaacaataatcagcataatcaaaaccagcatattaacaacaacaacgaaaataccaaccct
gacgctgctagccagcatcataataataacagtggttggaacggttctcagttaccatcgataaaagagcacttga
agaaaaaccccctttatacacacagatcatcttcccaattagatcagctaaactcttgctcttcagtaaccgatcc
gagcaaacgttcttctaattcttcgtcgggttcttcaaatggtccaaagaatgatagttcacatccaatatggcat
cacaagacaacgtttgatgttgggatctcactcggaattagatatttctgtttatgatgctgcccacgaccata
tgttcttaggccaagttagactgtatccaatgattcataatttagcacatgcttcccaacaccaatggcacagttt
```

-continued

Sequence Listing

```
gaaacctcgcgttattgatgaagttgtgtccggtgatattttaatcaaatggacttacaaacagacaaagaaaaga
cattatggcccacaagattttgaagttcttcgattattgggtaagggtacttttggccaagtctaccaagttaaga
agaaagacactcaaagaatttatgcaatgaaagttctctccaagaaagttattgtcaagaaaaatgagatcgccca
cacaattggcgaaagaaatatcctagtcacgacagcgtccaaatcgtccccattcattgtcggattgaagttttcc
tttcaaacaccaacagatctgtatttggtcactgattatatgagtggtggagaattattctggcatttacaaaagg
agggccgttttcggaagacagagcgaaattctatatcgctgagttagtcctagcgttagaacatttacacgataa
cgatatcgtttacagggacctaaagcctgaaaacattctactcgatgccaacatcgctctttgcgatttt
ggtctttctaaagctgacttgaaggatagaacaaacacattttgcggcaccacgaatacctgcaccagaattgt
tactggacgaaaccggctacaccaaaatggtcgatttctggtctctaggtgttttgatatttgaaatgtgttgtgg
ttggtcccctttctttgcggaaaataatcaaaaaatgtaccaaaaaattgcctttggtaaagtcaaattccccaga
gacgtactgtcacaagaggggaggtcttttgtaaagggtttactaaacagaaaattcctacaaaactcgtactt
tgatgatggaagagaactacgagctcatccattttttcgcagatatcgactgggaggccttgaagcagaaaaaat
tccaccacctttcaaacctcacctagtctcggagacggatacctcgaattttgacccagagttcacaacagcttca
acttcatacatgaacaagcaccagccgatgatgactgctaccccgctatctccagccatgcaagcaaagtttgctg
gtttcaccttttgttgatgagtccgccatcgatgaacacgttaataacacagaaaattcctacaaaactcgtactt
tatgaaacctggttcctttatcccgggaaatccaaacttacctccagacgaagatgtcatcgatgatgacgggac
gaggacatcaatgatgattcaaccaagagaaaaatatgaacaacagccattcgcagatggacttcgacggcgacc
aacacatggatgacgaatttgtcagtggaagattcgaaatatga
```

Rtg2
SEQ ID No: 3

```
  1 MSTLSDSDTE TEVVSRNLCG IVDIGSNGIR FSISSKAAHH ARIMPCVFKD RVGLSLYEVQ
 61 YNTHTNAKCP IPRDIIKEVC SAMKRFKLIC DDFGVPETSV RVIATEATRD AINADEFVNA
121 VYGSTGWKVE ILGQEDETRV GIYGVVSSFN TVRGLYLDVA GGSTQLSWVI SSHGEVKQSS
181 KPVSLPYGAG TLLRRMRTDD NRALFYEIKE AYKDAIEKIG IPQEMIDDAK KEGGFDLWTR
241 GGGLRGMGHL LLYQSEGYPI QTIINGYACT YEEFSSMSDY LFLKQKIPGS SKEHKIFKVS
301 DRRALQLPAV GLFMSAVFEA IPQIKAVHFS EGGVREGSLY SLLPKEIRAQ DPLLIASRPY
361 APLLTEKYLY LLRTSIPQED IPEIVNERIA PALCNLAFVH ASYPKELQPT AALHVATRGI
421 IAGCHGLSHR ARALIGIALC SRWGGNIPES EEKYSQELEQ VVLREGDKAE ALRIVWWTKY
481 IGTIMYVICG VHPGGNIRDN VFDFHVSKRS EVETSLKELI IDDANTTKVK EESTRKNRGY
541 EVVVRISKDD LKTSASVRSR IITLQKKVRK LSRGSVERVK IGVQFYEE
```

Rtg2
>YGL252C Chr 7
SEQ ID No: 4

```
atgtcaacacttagcgatagtgataccgagactgaggtcgtgtcgagaaacttgtgtggaatcgtcgacataggt
ctaatggtattcgttttagtatatcttccaaggctgcacatcatgcaagaattatgccttgtgtttttaaagatag
ggttggtctttctctatacgaagttcaatataatacacatacgaacgcaaaatgccctattcccagagatattata
aaagagggttgttctgccatgaagagattcaaattaatttgcgatgattttggtgtacctgaaactagtgtcagag
taattgcaacagaagccacgcgagatgctattaacgcggatgaatttgttaatgctgtttacggtagcactggctg
gaaagtagaaatattaggccaggaagatgaaactagggtcggcatatatggtgttgtttcctcatttaatacagta
agaggtctatatctagatgtggcaggtggtagtactcagttatcatgggtaataagctcgcacgtgagaagtcaagc
aatccagcaaacctgtatctttgccatatggagctggaactcttttgagaagaatgagaacagatgataatagggc
actttttatgagattaaaagaagctacaaagatgcgattgaaatatacctcaagaaatgattgatgac
gccaagaaagaaggtggatttgaccttggacccgtgggggtggttttaagagtatgggacatctgcttctttacc
agtcggaaggttatcccatccaaacaataattaacgagataggcttcacttatgaagaattctcgtctatgtcaga
ttatctattcctaaaacaaaaaataccaggttcttcaaaagagcataaaatatttaaggtttctgatagaagggct
ttacaacttcctgccgttggtttgttcatgagtgctgttttgaagcgattccccagatcaaagctgacattta
gtgagggtggtgttcgagagggttcacttttattctcttcttccaaaagaaattcgtgcacaagatccattgctaat
tgcgtcccgtcctatgctccattacttactgaaaaatatctatatctattgagaacatcaatcccacaagaagat
ataccagaaatagtaaacgaaaggattgctcctgcttatgtaacttagcatttgttcatgcctcttatccaaagg
agttacaaccaacagctgcattacatcgttgctacaagaggggataaacgcggctgtcatggattatctcacagagc
tagagcgctgataggaattgctctatgtagtagatggggcggcaacattccggaatctgaagaaaaatactcccaa
gaattagaacaagtagttctacgcgaaggtgataaagctgaagcattgagaattgtatggtggacgaagtatattg
gtacgattatgtatgtgatttgcggtgttcatccaggtggtaatatcagagataacgtatttgatttccatgtttc
taagcgtagtgaggtgggagaccagtttaaaagaattaatcattgatgatgcaaacactacaaaggtaaaagaagaa
tccacgcgtaaaaatcgcgggtatgaagtggttgtgagaattagtaaggacgatcttaaaacaagtgcttccgttc
gttccagaattatcacgctacaaaagaaagtacgcaagctatctagaggaagtgtagagagggttaaaattggcgt
gcaattttatgaagaataa
```

Gcn5
SEQ ID No: 5

```
  1 MVTKHQIEED HLDGATTDPE VKRVKLENNV EEIQPEQAET NKQEGTDKEN KGKFEKETER
 61 IGGSEVVTDV EKGIVKFEFD GVEYTFKERP SVVEENEGKI EFRVVNNDNT KENMMVLTGL
121 KNIFQKQLPK MPKEYIARLV YDRSHLSMAV IRKPLTVVGG ITYRPFDKRE FAEIVFCAIS
181 STEQVRGYGA HLMNHLKDYV RNTSNIKYFL TYADNYAIGY FKKQGFTKEI TLDKSIWMGY
241 IKDYEGGTLM QCSMLPRIRY LDAGKILLLQ EAALRRKIRT ISKSHIVRPG LEQFKDLNNI
301 KPIDPMTIPG LKEAGWTPEM DALAQRPKRG PHDAAIQNIL TELQNHAAAW PFLQPVNKEE
361 VPDYYDFIKE PMDLSTMEIK LESNKYQKME DFIYDARLVF NNCRMYNGEN TSYYKYANRL
421 EKFFNNKVKE IPEYSHLID
```

Gcn5
SEQ ID No: 6

```
tcttaaacacttatgggcagcaaaaaatgcgtctttcttccctcgtctgttgttttatgtagggcgtaatgatgtt
tgcttgtcaacaaatgaatacgtacagaagagaattctagccaaggcaattattgcatactgcaagtactgagtac
gttaacgttgctagaataacattaaatgagatgtagcaatgcagatccttcctcagtaggcttaatgctccactag
aattttttgaccagccactatttgcttttttcgcaatcctttttcaatactcgagagcaaagacaaaaaaaataagac
atgtagtgcgctgtatggaaagaattaattagaactttacaaacgcgtgttaaacaggcatatttaagtgtttgg
```

```
acctaaacaatatatcgactattgaaattcttacgcaagatttttatagttggatattcatatattcttacaact
ctctctactttcagtttttgaagctatatgtatcattatatacgtttatggattttcaaacctaaacaattata
ctgcgtaaatgtttgattaagcaataaataaaaacaaaggattggtaaggaagaccgtgagccgcccaaaagtct
tcagttaactcaggttcgtattctacattagatggtcacaaaacatcagattgaagaggatcacttggatggagct
acgacggatcccgaagttaaacgggtaaaattagaaaacaacgttgaagaaatacaacctgagcaggctgagacca
ataaacaagagggcaccgataaagagaataaggaaagttcgagaaagaaactgagagaataggaggatctgaagt
ggttacagatgtgtgaaaaaggaattgtcaaatttgaatttgatggtgttgaatacacattcaaagagagaccagt
gtcgtagaggaaaatgaaggtaaaattgagtttaggtggtgaataatgataatactaaagaaaacatgatggtcc
taactggattaaaaaacatttttcaaaagcaattaccaaaaatgcccaaagaatacattgccaggttagtctatga
tcgaagtcatctttccatggctgtcattaggaagccattgactgtcgtaggtggcataacatatcgacctttcgat
aagagagaattcgcagaaattgttttctgtgccatcagttcgacggcagatgacggtgtatggtgcgcatctaa
tgaatcacttaaaagactatgttagaaatacctcgaacataaaatatttttgacatatgcagataattacgctat
tggatactttaaaaagcaaggcttcactaaagaaatcacgttggataaaagtatatggatgggatatattaaagat
tatgaaggtggtacgctgatgcaatgttctatgttaccaagaatacgatatttggacgcaggtaagattctattat
tacaagaagcggccctgcgaagaaaaataagaacgattctgaaatcgccatattgtaaggcctggtttagagcaatt
caaagacttaaacaatatcaaaccgattgatccaatgactattcctggcttgaaagaagccggctggactcccgag
atggatgcgttggcacaacgtcccaagcgtggtccacacgatgcagcaatacagaatatactcacagagctacaaa
atcatgcagcagcttggcccttcttacaacccgttaataaagaggaggtccccgactattatgattttatcaaaga
gccatggacttgagcaccatggaaataaaattagagagcaaaatatcagaagatgagacttcatatatgat
gccagattggtgtttaacaattgccgaatgtacaatggcgagaatacgtcgtattacaagtatgctaataggctag
agaaattcttcaataataaagtaaaagaaatacctgaatattctcaccttattgattaatgcgtagaagaagcttt
tccgctactattcctttcgaagaagaaatatgtttagtacggcgagacgatgtgatcaattgaggttatttac
tacttttcctttcatttttgtaaggttttcttctttgttagtgtgacgttggtatttacctttatgtaactatat
```

Tor1

SEQ ID No: 7

```
   1 MEPHEEQIWK SKLLKAANND MDMDRNVPLA PNLNVNMNMK MNASRNGDEF GLTSSRFDGV
  61 VIGSNGDVNF KPILEKIFRE LTSDYKEERK LASISLFDLL VSLEHELSIE EFQAVSNDIN
 121 NKILELVHTK KTSTRVGAVL SIDTLISFYA YTERLPNETS RLAGYLRGLI PSNDVEVMRL
 181 AAKTLGKLAV PGGTYTSDFV EFEIKSCLEW LTASTEKNSF SSSKPDHAKH RALLIITALA
 241 ENCPYLLYQY LNSILDNIWR ALRDPHLVIR IDASITLAKC LSTLRNRDPQ LTSQWVQRLA
 301 TSCEYGFQVN TLECIHASLL VYKEILFLKD PFLNQVFDQM CLNCIAYENH KAKMIREKIY
 361 QIVPLLASFN PQLFAGKYLH QIMDNYLEIL TNAPAKKIPH LKDDKPQILI SIGDIAYEVG
 421 PDIAPYVKQI LDYIEHDLQT KFKFRKKFEN EIFYCIGRLA VPLGPVLGKL LNRNILDLMF
 481 KCPLSDYMQE TFQILTERIP SLGPKINDEL LNLVCSTLSG TPFIQPGSPM EIPSFSRERA
 541 REWRNKSILQ KTGESNDDNN DIKIIIQAFR MLKNIKSRFS LVEFVRIVAL SYIEHTDPRV
 601 RKLAALTSCE IYVKDNICKQ TSLHSLNTVS EVLSKLLAIT IADPLQDIRL EVLKNLNPCF
 661 DPQLAQPDNL RLLFIALHDE SFNIQSVAME LVGRLSSVNP AYVIPSIRKI LLELLTKLKF
 721 STSSREKEET ASLLCTLIRS SKDVAKPYIE PLLNVLLPKF QDTSSTVAST ALRTIGELSV
 781 VGGEDMKIYL KDLFPLIIKT FQDQSNSFKR EAALKAGLQL LLDYPELLGI
 841 LVNILKTENS QNIRRQTVTL IGILGAIDPY RQKEREVTST TDISTEQNAP PIDIALLMQG
 901 MSPSNDEYYT TVVIHCLLKI LKDPSLSSYH TAVIQAIMHI FQTLGLKCVS FLDQIIPTIL
 961 DVMRTCSQSL LEFYFQQLCS LIIIVRQHIR PHVDSIFQAI KDFSSVAKLQ ITLVSVIEAI
1021 SKALEGEFKR LVPLTLTLFL VILENDKSSD KVLSRRVLRL LESFGPNLEG YSHLITPKIV
1081 QMAEFTSGNL QRSAIITIGK LAKDVDLFEM SSRIVHSLLR VLSSTTSDEL SKVIMNTLSL
1141 LLIQMGTSFA IFIPVINEVL MKKHIQHTIY DDLTNRILNN DVLPTKILEA NTTDYKPAEQ
1201 MEAADAGVAK LPINQSVLKS AWNSSQQRTK EDWQEWSKRL SIQLLKESPS HALRACSNLA
1261 SMYYPLAKEL FNTAFACVWT ELYSQYQEDL IESLCIALSS PLNPPEIHQT LLNLVEFMEH
1321 DDKALPIPTQ SLGEYAERCH AYAKALHYKE IKFIKEPENS TIESLISINN QLNQTDAAIG
1381 ILKHAQQHHS LQLKETWFEK LERWEDALHA YNEREKAGDT SVSVTLGKMR SLHALAEWEQ
1441 LSQLAARKWK VSKLQTKKLI APLAAGARGG SGEWDMLDEY ISVMKPKSPD KEFFDAILYL
1501 HKNDYDNASK HILNARDLLV TEISALINES YNRAYSVIVR TQIITEFEEI IKYKQLPPNS
1561 EKKLHYQNLW TKRLLGCQKN VDLWQRVLRI RSLVIKPKQD LQIWIKFANL CRKSGRMRLA
1621 NKALNMLLEG GTILVYQIRS KPPPPVVYAQ LKYIWATGAY KEALNHLIGF TSRLAHDLGL
1681 DPNNMIAQSV KLSSASTAPY VEEYTKLLAR CFLKQGEWRI ATQPNWRNTN PDAILGSYLL
1741 ATHFDKNWYK AWHNWALANF EVISMVQEET KLNGGKNDDD DDTAVNNDNV RIDGSILGSG
1801 SLTINGNRYP LELIQRHVVP AIKGFFHSIS LLETSCLQDT LRLSTLLFNF GGIKEVSQAM
1861 YEGFNLMKIE NWLEVLPQLI SRIHQPDPTV SNSLLSLLSD LGKAHPQALV YPLTVAIKSE
1921 SVSRQKAALS IIEKIRIHSP VLVNQAELVS HELIRVAVLW HELWYEGLED ASRQFFVEHN
1981 IEKMFSTLEP LHKHLGNEPQ TLSEVSFQKS FGRDLNDAYE WLNNYKKSKD INNLNQAWDI
2041 YYNVFRKITR QIPQLQTLDL QHVSPQLLAT HDLELAVPGT YFPGKPTIRI AKFEPLFSVI
2101 SSKQRPRKFS IKGSDGKDYK YVLKGHEDIR QDSLVMQLFG LVNTLLKNDS ECFKRHLDIQ
2161 QYPAIPLSPK SGLLGWVPNS DTFHVLIREH RDAKKIPLNI EHWVMLQMAP DYENLTLLQK
2221 IEVFTYALDN TKGQDLYKIL WLKSRSSETW LERRTTYTRS LAVMSMTGYI LGLGDRHPSN
2281 LMLDRITGKV IHIDFGDCFE AAILREKYPE KVPFRLTRML TYAMEVSGIE GSFRITCENV
2341 MRVLRDNKES LMAILEAFAL DPLIHWGFDL PPQKLTEQTG IPLPLINPSE LLRKGAITVE
2401 EAANMEAEQQ NETRNARAML VLRRITDKLT GNDIKRFNEL DVPEQVDKLI QQATSIERLC
2461 QHYIGWCPFW
```

Tor1
>YJR066W Chr 10

SEQ ID No: 8

```
atggaaccgcatgaggagcagatttggaagagtaaactttttgaaagcggctaacaacgatatggacatggataaa
atgtgccgttggcaccgaatctgaatgtgaatatgaacatgaaaatgaatgcgagcaggaacggggatgaattcgg
tctgacttctagtaggtttgatggagtggtgattggcagtaatggggatgtaaatttaagcccattttggagaaa
atttccgcgaattaaccagtgattacaaggaggaacgaaaattggccagtatttcattatttgatctactagtat
ccttggaacatgaattgtcgatagaagagttccaagcagtttcaaatgacataaacaataagattttggagctggt
ccatacaaaaaaaacgagcactagggtaggggctgttctatccatagacactttgatttcattctacgcatatact
```

```
gaaaggttgcctaacgaaacttcacgactggctggttaccttcgagggctaatacccttctaatgatgtagaggtca
tgagactcgctgcaaagactctgggcaagttagccgttccaggaggtacatataccctctgatttcgtggaatttga
gataaagtcttgcttagaatggcttactgcctccacggaaaagaattcattctcgagttcgaagccagaccatgct
aaacatgctgcgcttctgattataacagcgttggcagagaattgtccttatttactctaccaatacttgaattcca
tactagataacatttggagagcactaagagacccacatttggtgatcagaattgatgcgtccattacattggccaa
atgtcttttccaccctacgaaatagggatcctcagttaactagccagtgggtgcagagattggctacaagttgtgaa
tacggatttcaagtaaacacattagaatgcatccatgcaagtttgttggtttataaggaaatcttgttttttgaagg
atcccttttgaatcaagtgttcgaccaaatgtgtctaaattgcatagcttatgaaaatcataaagcgaaatgat
tagagaaaagatttaccagattgttcccctattagcatcgttcaatcctcaattattttgctggcaaatatttgcac
caaattatggacaactatttagagattttaaccaatgctccagcaaataaaataccacatctcaaagatgacaaac
cacagattttaatatcgattggtgatattgcatatgaagtcgggcccgatatcgcaccttatgtgaaacaaattct
tgattatattgaacatgatttacagacgaaattcaaattcagaaagaaatttgaaatgaaattttctactgcatc
ggaagattggcagttcccttgggccccgttctaggtaaattattaaacagaaatatactggacctgatgttcaaat
gccctctttccgactatatgcaggaaacgtttcaaattctgactgagagaataccatcactaggccccaaaataaa
tgacgagttgcttaacctagtctgttcaaccttatctggaacaccatttatccagccagggtcaccaatggagata
ccatcgttttcgagagaaagagcaagagaatggagaaataaaaacatcctacagaaaactggtgaaagtaacgatg
ataataatgatataaaaatcattatacaagcttttagaatgttaaaaaatatcaaaagcagattttcgttggtgga
attcgtgagaattgttgcactttcttacattgagcatacagatcccagagtaaggaaactagctgcgttgacatct
tgtgaaatttacgtcaaggataacatctgcaaacaaacatcactacactctctgaacactgtatctgaagtgttat
caaagcttctagccattacgattgcggacccttttacaagatatccgtttagaagttttaaagaatcttaatccatg
tttcgatccccagttggcacaaccagataatttgagactcttgtttactgcactgcacgatgagtcgttcaatatt
cagtcagtagcaatggagcttgtcggtaggttgtcttccgtaaacctgcatacgtcatcccatcgataagaaaaa
tactactggaactgctaacaaaattaaaattctcaacttcttctcgagaaaaggaagaaactgccagtttgttatg
tactcttatcaggtcgagtaaagatgttgcgaaaccttatatcgaacctctttttaaatgttcttttaccaaaattc
caagatacctcttcaacggttgcatcaactgcactgagaactataggtgagctatctgttgtagggggcgaagata
tgaagatatatcttaaggatttgtttcctttaattatcaaaacatttcaggatcaatcaaactctttcaagagaga
agctgcacttaaggcccttggtcaacttgcagccttcatctggttacgtgatagatcctttactgactatcccgaa
ttattgggtatattggtgaatatattgaagacagaaaactctcaaaatattaggagacaaacagtcactttgatag
gtatactgggagctatcgacccatatcgccaaaaagaacgtgaggttacctctactaccgatatatctacagaaca
gaacgccccgcctatcgacattgctcttctcatgcagggcatgtctccttcgaatgatgagtattataccactgtt
gtcattcactgcctgctaaaaatcctaaaagatccatccctcatcatcttaccacactgccgtgatccaagcgatta
tgcatattttcaaaccctttggtctaaaatgtgtttcattcttggaccagatcatcccaactattttggacgtaat
gcgtacatgctctcagtcactattagaattttacttccaacagctttgctctttgattattatcgtaaggcaacac
ataagacctcatgtcgattctatattccaggctatcaaagatttttcttcggttgctaagctacaaataacgcttg
taagtgttattgaagcaatatcaaaggctctggagggtgaattcaaaagattggtccctcttactctgaccttgtt
ccttgtaattttggagaatgacaagtcgtgacaaggtcctctccagaaggtattgagactgttagaatcgttt
ggtcctaacttagaaggttattcgcatttgattacacccaagatagttcaaatggcagaattcaccagcgggaacc
tacaaaggtctgcaataattactattggcaaactggccaaggatgttgaccttttgagatgtcctcaagaattgt
tcactctttacttagggtactaagttcaacaacgagtgacgaactctcaaaagtcattatgaatactttaagtcta
ctgctaatacaaatgggcacatcctttgctatcttcatccctgtcattgaagttttaatgaagaaacatattc
aacacacaatatatgatgacttgacaaacagaatattaaacaatgatgttttacccacaaaaattcttgaagcaaa
tacaacggattataagcccgcggaacaaatggaggcagcagatgctggggtcgcaaaattacctataaaccaatca
gttttgaaaagtgcatggaattctagccaacaaagaactaaagaagattggcaggaatggagcaaacgtctatcca
ttcaattattaaaagagtcaccctcccatgctctaagagcttgttcaagatgtgtattatccactagc
caaagaacttttttaataccgcattcgcatgtgtttggaccgaactttatagccaatatcaagaagatttaattggg
tcattatgtatagccttatcttctcccttaaatccaccagaaatacatcaaacattgttaaacctggtagaattta
tggaacacgatgacaaggcattaccaataccaactcaaagcctgggcgagtatgctgaaagatgtcacgcctatgc
caaagcgctacattataaagagattaaatttattaaagagcctgagaactcaactattgaatcattgatcagcatt
aacaaccagctgaatcaaacggatgctgcaattggtatattaaagcatgcccaacaacatcattcacttcaattaa
aggagacatggtttgaaaaattagagcgttgggaagatgcactacatgcttataatgaacgtgaaaaggcaggtga
tacttccgtgagcgttacactcggtaagatgagatcccttcatgcccttggcgaatgggaacagttgtcgcaattg
gcagctagaaagtgaaagtttcgaagctacaaactaagaagctaatagctcccttggcagctggtgctgcgtggg
ggttgggagatgggatatgcttgagcaatatatcagcgttgatgaaacctaaatctccagataaggaattttttga
tgcaattttatacttgcacaagaatgattacgacaatgctagtaagcatatattaaacgccagagatttgcttgtg
actgaaatttccgcgttgatcaatgaaagttataatagagcatatagcgttattgttagaactcaaataataacag
agtttgaggaaatcatcaagtataaacaattgccacctcaattccgagaaaaaacttcactatcaaatctttggac
aaaaagactgctgggctgccaaaaaaatgtcgatttatggcaaagatcgttagagtaagatcattggtaataaag
cccaagcaagacctgcaaatatggataaaatttgcaaatttgtgcagaaaatctggtagaatgaggctagcaaata
aggcattgaatatgctactagaaggaggcaacgatcctagtttaccaaatacgttcaaagctcctcccccagttgt
ttacgcgcaactaaaatatatttgggctacaggagcttataaagaagcattaaaccacttgataggatttacatcc
aggttagcgcatgatcttggtttggatccgaataatatgatcgcgcaaagtgtcaaactctcaagtgcaagtactg
ctccgtatgttgaggaatacacaaaattattagctcgatgtttttttaaagcaaggtgagtggagaatagcaacaca
accgaactggagaaacacaaatccggatgcaattcttggttcttatctattggctacacatttcgataaaaattgg
tacaaggcatggcataatttgggccttagctaattttgaagtaatatccatggttcaggaagagactaagctcaacg
gaggtaagaatgatgatgatgatgacacggcagttaataatgataatgtgccgattgcggtagtatcctaggaag
tggttctttgactattaatggcaacagatacccgctagagcttattcaaagacatgttgttccagcgatcaagggc
tttttcattcaatatctctattagaaacaagttgtttgcaagcacgttggagttattgactcttttatttaact
ttggtggtattaaagaagtctcacaagccatgtatgaaggcttcaatttgatgaaaatagagaactggcttgaagt
cttaccacagttgatctctcgtatacatcagccagatcctacggtgataattccctttgtcgtttgctttctgat
ttagggaaagctcatccacaagctctcgtgtatcctttaactgtcgcgatcaagtctgaatctgtttcaagacaaa
aagcggctcttcaataatagagaaaattaggattcatagtccagtcctggtaaaccaggcagaattagttagtca
cgagttgatcagagtagccgttctatggcacgaattatggtatgaaggactggaagatgcgagccgccaattttc
gttgaacataacatagaaaaaatgttttctactttagaaccttactaacacactttaggcaatgagcctcaacgt
taagtgaggtatcgtttcagaaatcatttggtagagatttgaacgatgcctacgaatggttgaataactacaaaa
gtcaaaagacatcaataatttgaaccaagcttgggatatttattataacgtcttcagaaaaataacacgtcaaata
ccacagttacaaaccttagacttacagcatgtttctccccagcttctggctactcatgatctcgaattggctgttc
ctgggacatatttcccaggaaaacctaccattagaatagcgaagtttgagccattattttctgtgatctcttcgaa
gcaaaggccaagaaaattctccatcaagggtagcgacggtaaagattataaatacgttttaaaggggacatgaagat
```

```
ataagacaagatagccttgttatgcaattatttggtctagttaacactttgttgaagaatgattcagagtgtttca
agagacatttggatatccaacaatacccggctattccattgtcgcctaaatctggtttactaggatgggtaccaaa
tagtgacacattccacgttttgatcagagaacaccgtgatgccaaaaaaattccgttgaacattgaacattgggtt
atgttacaaatggcccccgattatgagaatttgactcttttacaaaaaattgaagtattcacgtacgctttagata
atacaaaaggccaagacctttataaaatattatggttaaagagtaggtcgtcagagacatggctagaacgtagaac
aacttatacgagatctttagcagttatgtccatgactggtatattctgggactaggtgatcgccatccaagcaac
ctgatgctagatagaatcaccggtaaagttatccacattgatttcgagtgttttgaagctgccatcttaagag
aaaagtatccagaaaaagtgccatttagactaactaggatgttaacatacgcaatggaagttagtggaattgaagg
cagtttccgaattacttgtgaaaatgtcatgagagtcttaagagataataaagaatcattaatggcgatcttggaa
gcttttgcgcttgatcctttgatccattgggatttgatttaccgccacaaaaacttactgagcaaactggaattc
ctttgccgttgattaatcctagtgaattattaaggaaggggcaattactgtcgaagaagcggcaaatatggaagc
agaacaacaaaatgagaccaaaaacgccagagcaatgcttgttttgagacgtattacagataaattaacgggcaat
gatatcaagaggttcaatgaattagacgtccctgagcaggttgataaactgatccaacaagccacttctattgaaa
ggttatgtcaacattatattggatggtgcccattctggtga
```

Ubp8

SEQ ID No: 9

```
  1 MSICPHIQQV FQNEKSKDGV LKTCNAARYI LNHSVPKEKF LNTMKCGTCH EINSGATFMC
 61 LQCGFCGCWN HSHFLSHSKQ IGHIFGINSN NGLLFCFKCE DYIGNIDLIN DAILAKYWDD
121 VCTKTMVPSM ERRDGLSGLI NMGSTCFMSS ILQCLIHNPY FIRHSMSQIH SNNCKVRSPD
181 KCFSCALDKI VHELYGALNT KQASSSSTST NRQTGFIYLL TCAWKINQNL AGYSQQDAHE
241 FWQFIINQIH QSYVLDLPNA KEVSRANNKQ CECIVHTVFE GSLESSIVCP GCQNNSKTTI
301 DPFLDLSLDI KDKKKLYECL DSFHKKEQLK DFNYHCGECN STQDAIKQLG IHKLPSVLVL
361 QLKRFEHLLN GSNRKLDDFI EFPTYLNMKN YCSTKEKDKH SENGKVPDII YELIGIVSHK
421 GTVNEGHYIA FCKISGGQWF KFNDSMVSSI SQEEVLKEQA YLLFYTIRQV N
```

Ubp8
>YMR223W Chr 13

SEQ ID No: 10

```
atgagcatttgtccacatatacagcaagtatttcagaatgaaaagtctaaagatggggttctaaaaacgtgcaatg
ctgccaggtatatattaaatcattccgtacccaaggaaaaattcttaaacaccatgaaatgtggtacatgccacga
aataaactctggtgcaacttcatgtgtctacaatgtggattgtggataccattcgcattttctctct
cacagtaaacagattggtcacatatttggtatcaactcaaataatggccttttattttgcttcaaatgtgaggact
atatagggaatatcgatctgattaacgatgctatcctagcgaagtattgggacgacgtgtgcacaaagaccatggt
tcctagcatggaaagaagatgggctttctggcctgatcaacatgggatccacttgtttcatgagtagtattctc
caatgtctaatccataacccttactttattaggcactcaatgagtcaaattcattctaataattgtaaagtgcgtt
ctccagataaatgttttcatgtgcactcgataaaattgttcatgaactttatggagcgctgaatacaaagcaagc
ttcttcgtcatctactaatcggcaaaccggattcatatatctttaagctgcctggaaaatcaatcaa
aatctagcagggtattcacaacaagatgctcatgaattttggcagttttataattaaccaaatccaccaaagctatg
ttcttgatttgccaaatgccaaggaagtcagcagagcaaataataagcagtgtgaatgcatagtgcatactgtgtt
tgagggctccttggaaagttctattgtgtgtccaggctgtcaaataattcaaagacaaccattgatccattcttg
gatctttctctggatatcaaggataagaaaaactttatgaatgtcttgacagttcataaaaaagaacagttga
aggatttcaactatcattgtggggagtcagcaatagcactcaagattgcaagactaggcatacacaaattacc
atcggttttggttttgcaattgaaaagattcgaacacctacttaatggaagtaacagaaaactagacgatttatt
gaatttccaacttatttaaatatgaaaaattactgttcaacgaaggaaaaagataagcattctgaaaatggcaagg
ttccagacattatttacgaattaatcggtattgtttcccacaaggggacggttaatgagggacattatattgcatt
ttgtaaaattctggagggcaatggtttaaattcaatgattccatggtctcctctatatctcaagaagaggttta
aaggaacaggcatatttattattctacaccattcgtcaagtaaattga
```

Spt7

SEQ ID No: 11

```
   1 MTERIPIKNY QRTNAKALLK LTEKLFNKNF FDLYLTSQQL VVLEYLLSIS SEEDKLKAWD
  61 YPFLKGNIALN VEKSFPLTQE EEHHGAVSPA VDTRSDDVSS QTIKDNNNTN TNTSISNENH
 121 VENEIEDKGD NAIANEDNFV NNDESDNVEE DLFKLDLEDL KQQISGTRFI GNLSLKIRYV
 181 LWQCAIDYIY CDRNEFGDEN DTEYTLLDVE EKEEEEIGKN EKPQNKEGIS KFAEDEDYDD
 241 EDENYDEDST DVKNVDDPPK NLDSISSSNI EIDDERRLVL NISISKETLS KLKTNNVEEI
 301 MGNWNKIYHS FEYDKETMIK RLKLEESDKM IEKGKKKRSR SDLEAATDEQ DRENTNDEPD
 361 TNQKLPTPEG STFSDTGNKR PKQSNLDLTV NLGIENLSLK HLLSSIQQKK SQLGISDYEL
 421 KHLIMDVRKN RSKWTSDERI GQEELYEACE KVVLELRNYT EHSTPFLNKV SKREAPNYHQ
 481 IIKKSMDLNT VLKKLKSFQY DSKQEFVDDI MLIWKNCLTY NSDPSHFLRG HAIAMQKKSL
 541 QLIRMIPNIT IRNRADLEKE IEDMEKDKDY ELDEEEEVAG SGRKGLNMGA HMLAKENGKV
 601 SEKDSSKTVK DEAPTNDDKL TSVIPEGEKE KDKTASSTVT VHENVNKNEI KENGKNEEQD
 661 MVEESSKTED SSKDADAAKK DTEDGLQDKT AENKEAGENN EEEEDDDDED EDEDMVDSQS
 721 YLLEKDDDRD DLEISVWKTV TAKVRAEICL KRTEYFKNGK LNSDSEAFLK NPQRMKRFDQ
 781 LFLEYKEQKA LESYRQKIEQ NSIMKNGFGT VLKQEDDDQL QFHNDHSLNG NEAFEKQPND
 841 IELDDTRFLQ EYDISNAIPD IVYEGVNTKT LDKMEDASVD RMLQNGINKQ SRFLANKDLG
 901 LTPKMNQNIT LIQQIRHICH KISLIRMLQS PLSAQNSRSN PNAFLNNHIY NYTIIDDSLD
 961 IDPVSQLPTH DYKNNRELIW KFMHKNISKV AMANGFETAH PSAINMLTEI AGDYLSNLIK
1021 TLKLHHETNS LNRGTNVEML QTTLLENGIN RPDDLFSYVE SEFGKKTKKL QDIKQKLESF
1081 LRALLRPTLQ ELSERNFEDE SQSFFTGDFA SELTGEDFFG FRELGLEKEF GVLSSSVPLQ
1141 LLTTQFQTVD GETKVQAKKI QPEESDSIVY KKITKGMLDA GSFWNTLLPL LQKDYERSKA
1201 YIAKQSKSSA NDKTSMTSTE DNSFALLEED QFVSKKTATK ARLPPTGKIS TTYKKKPIAS
1261 AFILPEEDLE NDVKADPTTT VNAKVGAEND GDSSLFLRTP QPLDPLDMDD AFDDTNMGSN
1321 SSFSLSLPRL NQ
```

Sequence Listing

Spt7
>YER081C Chr 2

SEQ ID No: 12 atgactgaaagaataccaataaagaattatcaaagaacaaatgccaaagctttacttaaattgactgaaaaacttt
ttaacaagaactttttttgatctctatttaacctctcagcaattggtcgttcttgaatacctgctgtcgatttcaag
tgaagaagacaaactgaaagcatgggactatttcttaaagggaaacatagcattaaatgtcgaaaaatcatttcca
ttaacccaagaagaagaacatcacggagcggtctctcctgccgttgacacacgatcagatgatgtatcatcacaaa
caattaaggacaataacaatactaataccaacaccagtatcagcaatgaaaatcatgttgaaaatgaaattgaaga
taaaggcgataacgcaatagcaaatgaagataattttgtgaataatgacgaaagtgataatgttgaagaagactta
ttcaaattagatctagaggacttgaagcagcaaataagcggaaagttttattggaaacttatccttgaaaatca
gatacgtcttgtggcagtgcgccatagattatatatactgtgatcgtaatgagtttggtgatgaaaatgatacaga
atacaccctattagatgttgaagaaggaggaagaggaaattggtaaaaatgagaagccacaaaacaaagaaggt
atttcgaagttcgccgaggatgaagattacgacgatgaagacgagaactatgatgaagacagtacagacgtaaaaa
atgtcgatgatcctccaaaaaatctcgattctatttcctcttctaatatcgaaattgacgatgaacgacgcttgt
gctaaatatctcaatatcaaaagaaacactgtcaaagttaaaaacaaataatgtagaagaaattatgggaaattgg
aacaaaatttaccacagtttttgaatacgataaagaaactatgataaagcgattaaaacttgaagaaagcgataaaa
tgatagagaaaggaaagaagaaacgaagtcgaagtgatttagaagcagctaccgatgaacaagatcgcgaaaatac
aaatgatgagccagatactaatcaaaaattgcccactcctgaagttcaacattcagcgatactgggaacaagcgc
cccaaacaaagtaatttagatttaacagtcaatctaggcatcgaaaatttatcattaaagcaccttctatcatcta
tccagcaaaaaaaatcccaattaggaatatcagattacgaattaaaacatctgattatggatgtcagaaaaaatcg
gtcaaaatggacatcggatgaaagaattgggcaagaggaattatacgaagcctgtgaaaggttgttttggaactt
agaaactacactgagcattctacaccatttctgaataaagtgagcaaaagagaagcccccaattatcatcaaatca
tcaaaaagtccatggacctgaatactgttttaaaaaaactgaaaagctttcaatatgactccaaacaagaatttgt
agacgatattatgctaatatggaaaaattgtttgacctataattcagatcctcacattttttgagagggcatgct
attgctatgcagaagaaatctcttcagttgattcgcatgattccaaatatcacaatccgaaacagggctgatttag
aaaaggaaattgaagatatggaaaaagacaaagactacgaaattagatgaggaagaggaagttgctggttctggaag
aaaaggattgaatatgggagctcatatgttggccaaagagaatggcaaggtgtcaggaaaaagatagctctaaaacc
gtcaaggatgaagcaccaaccaatgatgacaaactaacttctgtcatccctgaggggaaaagagaaagataaaa
ctgcttcatctactgtaacggtacacgaaaatgtaaataagaacgaaataaaagaaatgggaaaaatgaagagca
agatatggttgaggaaagtagtaagactgaggattcatcaaaagatgctgatgctgccaaaaaggatacggaagac
ggactacaagataaaactgcagaaaataaggaggctggggaaaataatgaagaggaagaggatgatgatgacgaag
atgaagacgaagacatggtcgactcccaatcttatttacttgaaaaggatgacgatagagacgatttggaaatatc
cgtgtgggaaactgtaactgccaaagtcgtgcggaaatttgcttaaaaagaactgaatattttaaaaatggaaaa
ttaaatagtgattcagaggcgttttttgaaaaacccacaaagaatgaaaaggttcgaccagctttttcttgaatata
aagagcagaaagctttagaatcatatcgtcaaaaaatagagcaaaattccattatgaaaaatggcttttggaacagt
actaaaacaggaagacgatgaccaattgcagtttcataatgatcactctttaaatggaaatgaagctttttgaaaag
caacccaatgatattgagttagatgataccagattcctacaggaatgatattagtaacgccattcctgacatag
tatacgagggagtaaatactaaaacattagacaagatggaagacgcttccgtggaccgcatgcttcaaaatggtat
caacaacaaagcagatttctggctaacaaggattttaggactaacacctcaagcaacaaaatatcacactgatt
cagcaaattaggcacatatgccataaaatatccctgatcagaatgttacagagcccttttatcggctcaaaactcca
gaagcaatcccaacgcttcttaacaaccacatttataattacactattattgatgactcactcgatattgatcc
ggtgtcacagctccaacgcatgattacaaaaacaacaggagctgatatggaaattcatgcataagaacatatct
aaggttgctatggccaatgggtttgaaactgcccatccatcgacaataaacatgcttactgaaatcgccgggatt
acctatctaatctgataaagactttgaagcttcatcatgaaactaactcctaaatagaggaacaaatgtgggaaat
gctgcaaacaacactgttggaaaacggtatcaacaggccagacgatctattttcctatgttgaatctgaatttggt
aaaaaaactaagaaacttcaggacatcaaacagaaactagaaagcttttgagagccttattaaggccaactttgc
aggagttgtccgagagaaacttgaagacgagagccaaagcttttttgcaggtgacttgccagcgaattgactgg
tgaagacttctttggttttagagagcttggattagaaaaggagtttggagttttgagttcatctgttccattacag
ttactgactactcagtttcaaactgttgacggggaaaccaaagtgcaggccaaaaagatccaaccggaagaatcag
acagcattgtgtataagaaaattacaaaaggtatgctggatgctggttcattctggaatactctacttcccctatt
acaaaaagattatgaacgttccaaggcctatatagcaaagcaaagcaagtcatctgcaaatgataaaactcaatg
acttccacagaagacaattctttcgctttactagaagaggatcagttttgtctcaaagaaaaccgcaacgaaggcaa
gattacctcctactggtaagataagtaccacatacaaaagaaaccgatcgcaagcgcgtttatacttccagaaga
agacttggaaaacgacgtaaaagcggatccaacaacaactgtaaacgccaaagtgggtcagaaaatgatggagat
tcttcctttattttttgcgaacgcctcaacctttagatcctttggatatggatgatgcttttgatgataccaatatgg
gcagcaatagttcatttagcttgagccttcctcgccttaatcaataa

SPT8

SEQ ID No: 13

```
  1 MDEVDDILIN NQVVDDEEDD EEMLSGLEND SKQDLEGNDD GGEDEEDDDD DDEDDDDDED
 61 EREDDDEQED DDGEDDAARM DKTATPTNEH QHDEQKAAAA GAGGAGDSGD AVTKIGSEDV
121 KLSDVDGGVG SREASSSTHE ASANGEVYEY YKHMLNAAQI ADSYNIYPTA AIPIQTHVNA
181 LAVSRGLKYL FLGGSDGYIR KYDLLNTLEG KLSLTILQKH SLAESIQNAG ILQSYWENEI
241 PQKKSEMKLS ANKTDYEPKV SPVHSLEVQS ECLFILSGLQ NGGITMQGVR YMEGSIAHYF
301 KGRNGHTQIV NILRLNGQED RFLSGSWDKR LLEWDLQTGD IVNEFKKSRS ELSSLEMRPL
361 YSSVDVSGNV NSGKENENAD DDMDSLFGDE DEDEKQDAGN EPVETGDGSN GEENKEQISE
421 ESLNIVYDES VFMTSGLNGS VHIWDRRMTQ SPALSLERGA GVPPWCLSAC WGVDGDHVYA
481 GRRNACVEQF DLKMPSKPIH NLKLPSISGP VSCVKAMPNN KHLLCASRDN IRLYNVEIAV
541 DASNSTTKSS KVPFLIVPGH HGGIISNLYL DPTSRFIIST SGNRGWQGNS TDTTLIYDID
601 LE
```

Spt8
>YLR055C Chr 12

SEQ ID No: 14 atggacgaggttgacgatattctaattaacaaccaggtggtggatgacgaggaggatgacgaagagatgctgagtg
ggctggaaaacgactcaaagcaggacctcgaggggaatgatgacggtggtgaagatgaagaggatgacgatgatga
tgatgaggacgatgatgatgacgaggacgaacgagaggacgacgatgaacaggaggacgacgatggtgaggacgac -continued Sequence Listing

```
gccgcaagaatggataagactgctacaccgacgaatgagcaccagcatgatgagcaaaaggctgctgctgctggtg
ctggcggtgcaggcgatagtggcgatgctgttactaagattggatccgaggatgtgaaattgagcgatgttgatgg
aggagtggggtccagggaagcatcttcctctacacacgaagcctctgctaatggagaggtttatgagtactataag
cacatgttgaatgccgcacagattgcggattcgtacaatatctaccccacggcagccatacccatccagacgcacg
tcaatgcgttggccgtgtccagggtctcaagtacctgtttttggggcggtagcgatggatacataaggaagtacga
cttgctgaacacgcttgaggggaaactttctctaactatcctgcagaagcattcgttggctgagtctattcagaac
gcgggtatcttgcagtcgtactgggaaaatgagatcccgcagaaaaatcagaaatgaaactctccgctaataaga
cagattacgagcccaaagttagccccgttcattctttggaagtccaaagcgaatgcctctttatactgagcgggct
acagaatggtgggattaccatgcaggcgttcgctacatggaggggagcattgcgcactattttaagggcaggaat
ggacatacccaaatcgttaacatactgagattaaacggtcaagaggacaggttttgagtggttcctgggataagc
gtcttttggaatgggatttgcagacgggtgacatagttaatgagttaaaaaatcaaggtctgaattgtcatcttt
ggaaatgcggccgctgtactcgtccgtggatgtgtccggtaacgtcaacagtggtaaagagaatgaaatgcagat
gacgatatggattctctgtttggtgatgaagacgaagacgaaaagcaagatgctggcaacgaacccgtcgagacgg
gggatggttctaatggtgaagagaacaaagaacagatatctgaagaatctttgaacatagtctatgatgaatccgt
ttttatgacctcagggttgaacggttccgtgcatattttgggaccgacgcatgacgcagtcgccagcattgtctctg
gagagaggtgcaggcgtccccaccgtggtgtttgtccgcatgttggggtgtagatggtgatcatgtgtatgcaggga
gaaggaatgcctgtgtggagcagtttgacttgaagatgccctcgaaacctatccataatttgaaactgccttctat
ttcagggcctgtctcttgtgttaaagccatgcctaataacaagcatttactatgtgcatcgcgggataatatcaga
ttgtacaacgttgaaattgcagtagatgcttcgaattcgactacaaagagttctaaagtgccgttcctcatcgtgc
cgggccatcacggtggtattatatcaaacttatacctcgaccccacttcaagatttataataagcacaagtggcaa
cagaggctggcagggggaattctacggacacgacccttatttacgatatagacttagaatag
```

Snf1

SEQ ID No: 15

```
  1 MSSNNNTNTA PANANSSHHH HHHHHHHHHH GHGGSNSTLN NPKSSLADGA HIGNYQIVKT
 61 LGEGSFGKVK LAYHTTTGQK VALKIINKKV LAKSDMQGRI EREISYLRLL RHPHIIKLYD
121 VIKSKDEIIM VIEYAGNELF DYIVQRDKMS EQEARRFFQQ IISAVEYCHR HKIVHRDLKP
181 ENLLLDEHLN VKIADFGLSN IMTDGNFLKT SCGSPNYAAP EVISGKLYAG PEVDVWSCGV
241 ILYVMLCRRL PFDDESIPVL FKNISNGVYT LPKFLSPGAA GLIKRMLIVN PLNRISIHEI
301 MQDDWFKVDL PEYLLPPDLK PHPEEENENN DSKKDGSSPD NDEIDDNLVN ILSSTMGYEK
361 DEIYESLESS EDTPAFNEIR DAYMLIKENK SLIKDMKANK SVSDELDTFL SQSPPTFQQQ
421 SKSHQKSQVD HETAKQHARR MASAITQQRT YHQSPFMDQY KEEDSTVSIL PTSLPQIHRA
481 NMLAQGSPAA SKISPLVTKK SKTRWHFGIR SRSYPLDVMG EIYIALKNLG AEWAKPSEED
541 LWTIKLRWKY DIGNKTNTNE KIPDLMKMVI QLFQIETNNY LVDFKFDGWE SSYGDDTTVS
601 NISEDEMSTF SAYPFLHLTT KLIMELAVNS QSN
```

Snf1
YDR477W Chr 4

SEQ ID No: 16

```
atgagcagtaacaacaacacaaacacagcacctgccaatgcaaattctagccaccaccaccaccatcaccaccatc
accaccaccatcacggtcatggcggaagcaactcgacgctaaacaatcccaagtcgtccttagcggatggtgcaca
tatcgggaactaccaaatcgtcaaacgctgggagagggtcctttggtaaagttaaattggcatatcataccact
acgggccaaaaagttgctctaaaaatcattaataagaaggttttggcaaagagtgatatgcagggcagaattgaaa
gagaaatatcttatctgagactcttaagcacccccacatcatcaagttatcaaatccaaagatga
aatcattatggttatagagtacgccgggaacgaattgttgactatattgttcagagagacaaaatgagcgagcaa
gaggcaagaagattttccagcagatcatcagtgccgtcgagtactgccataggcacaaaattgtccatagagatc
tgaagcctgaaaacttactactagatgagcatctgaatgtaaagattgccgattttggtttgtcaaacatcatgac
tgatggtaattttcttaaagacttcttgtggttctcccaattatgcggctcctgaagttatcagcggtaagctgtac
gcaggcccagaagtggacgtgtggcatgtggggttatcctttatgttatgcttgtcgtcgtctaccgtttgacg
atgaaagcatcccagtgcttttcaagaatatcagcaacggtgtttacacctcgcctaaattttatctcctggagc
tgctgggctaatcaaagaatgttaatcgttaatccattgaacagaataagcattcatgaaattatgcaagacgat
tggttcaaagttgacctgccagaatatctacttccaccagattctgaaacacaccagaagaagatgaaata
atgactcaaaaaaggatggcagcagcccagataacgatgaaattgatgacaaccttgtcaatattttatcatcgac
catgggttacgaaaaagacgagatttatgagtccttagaatcatcagaagacactcctgcattcaacgaaattagg
gacgcgtacatgttgattaaggagaataaatctttgatcaaggatatgaaggcaaacaaaagcgtcagtgatgaac
tggataccttctgtcccagtcacctccaacttttcaacaacaaagcaaatcccatcaaaagagtcaagtagatca
tgaaactgccaagcaacacgcaagaaggattggcaagtgctatcactcaaaagggacatatccaatcacccttc
atggatcagtataaagaagaagactctacagtttccattttgcctacatctttacctcgatccacagagctaata
tgttagcacaaggttcgccagctgcctctaaaatatctcctcttgtaacgaaaaaatctaaaacgagatggcattt
tggtatacgatctcgctcatatccattagacgttatgggtgaaatttatattgccttgaagaatttgggtgccgaa
tgggccaagccatctgaagaggattttgactatcaaattaaggtgaaatatgatattggaaacaagacaaaca
ctaatgaaaaaatacctgatttaatgaaaatggtaattcaattatttcaaattgaaaccaataattatttggtgaa
tttcaaatttgacggctgggaaagtagttatggagatgatactactgtttctaatatttctgaagatgaaatgagt
acttttcagcctaccatttttacatttaacaacaaaactaattatggaattagccgttaacagtcaaagcaatt
ga
```

ACS1

SEQ ID No: 17

```
  1 MSPSAVQSSK LEEQSSEIDK LKAKMSQSAA TAQRKKEHEY EHLTSVKIVP QRPISDRLQP
 61 AIATHYSPHL DGLQDYQRLH KESIEDPAKF FGSKATQFLN WSKPFDKVFI PDPKTGRPSF
121 QNNAWFLNGQ LNACYNCVDR HALKTPNKKA IIFEGDEPGQ GYSITYKELL EEVCQVAQVL
181 TYSMGVRKGD TVAVYMPMVP EAIITLLAIS RIGAIHSVVF AGFSSNSLRD RINDGDSKVV
241 ITTDESNRGG KVIETKRIVD DALRETPGVR HVLVYRKTNN PSVAFHAPRD LDWATEKKKY
301 KTYYPCTPVD SEDPLFLLYT SGSTGAPKGV QHSTAGYLLG ALLTMRYTFD THQEDVFFTA
361 GDIGWITGHT YVVYGPLLYG CATLVFEGTP AYPNYSRYWD IIDEHKVTQF YVAPTALRLL
421 KRAGDSYIEN HSLKSLRCLG SVGEPIAAEV WEWYSEKIGK NEIPIVDTYW QTESGSHLVT
481 PLAGGVTPMK PGSASFPPFG IDAVVLDPNT GEELNTSHAE GVLAVKAAWP SFARTIWKNH
541 DRYLDTYLNP YPGYYFTGDG AAKDKDGYIW ILGRVDDVVN VSGHRLSTAE IEAAIIEDPI
```

```
    601 VAECAVVGFN DDLTGQAVAA FVVLKNKSSW STATDDELQD IKKHLVFTVR KDIGPFAAPK
    661 LIILVDDLPK TRSGKIMRRI LRKILAGESD QLGDVSTLSN PGIVRHLIDS VKL
```

Acs1
>YAL054C Chr 1

SEQ ID No: 18

```
atgtcgccctctgccgtacaatcatcaaaactagaagaacagtcaagtgaaattgacaagttgaaagcaaaaatgt
cccagtctgccgccactgcgcagcagaagaaggaacatgagtatgaacatttgacttcggtcaagatcgtgccaca
acggcccatctcagatagactgcagcccgcaattgctacccactattctccacacttggacgggttgcaggactat
cagcgcttgcacaaggagtctattgaagaccctgctaagttcttcggttctaaagctacccaattttaaactggt
ctaagccattcgataaggtgttcatcccagaccctaaaacgggcaggccctccttccagaacaatgcatggttcct
caacggccaattaaacgcctgttacaactgtgttgacagacatgccttgaagactcctaacaagaaagccattatt
ttcgaaggtgacgagcctggccaaggctattccattacctacaaggaactacttgaagaagtttgtcaagtggcac
aagtgctgacttactctatgggcgttcgcaagggcgatactgttgccgtgtacatgcctatggtcccagaagcaat
cataaccttgtttggccattccccgtatcggtgccattcactccgtagtctttgccgggttttcttccaactccttg
agagatcgtatcaacgatgggactctaaagttgtcatcactacagatgaatccaacagaggtggtaaagtcattg
agactaaaagaattgttgatgacgcgctaagagagacccaggcgtgagacacgtcttgtttatagaaagaccaa
caatccatctgttgcttccatgccccagagatttggattgggcaacagaaaagaagaaatacaagacctactat
ccatgcacaccgttgattctgaggatccattattcttgttgtacgtctggttctggtgccccaagggtg
ttcaacattctaccgcaggttacttgctgggagctttgttgaccatgcgctacacttttgacactccaccaagaaga
cgttttcttcacagctggagacattggctggattacaggccacacttatgtggtttatggtcccttactatatggt
tgtgccactttggtctttgaagggactcctgcgtacccaaattactcccgttattgggatattattgatgaacaca
aagtcacccaatttatgttgccgtttgctcttgcgtttgttgaaaagagctggtgattcctacatcgaaattca
ttccttaaaatcttttgcgttgcttgggttcggtcggtgagccaattgctgctgaagtttgggagtggtactctgaa
aaaataggtaaaaatgaaatccccattgtagacacctactggcaaacagaatctggttcgcatctggtcaccccgc
tggctggtggtgttacaccaatgaaaccgggtctgcctcattcccttcttcggtattgatgcagttgttcttga
ccctaacactggtgaagaacttaacaccagccacgccagagggtgtccttgccgtcaaagctgcatggccatcattt
gcaagaactatttggaaaaatcatgataggtatctagacacttatttgaacccttaccctggctactatttcactg
gtgatggtgctgcaaaggataaggatggttatatctggattttgggtcgtgtagacgatggtggtgaacgtctctgg
tcaccgtctgtctaccgctgaaattgaggctgctattatcgaagatccaattgtggccgagtgtgctgttgtcgga
ttcaacgatgacttgactggtcaagcagttgctgcatttgtggtgttgaaaacaaatctagttggtccaccgcaa
cagatgatgaattacaagatatcaagaagcatttggtctttactgttagaaaaagacatcgggccatttgccgcacc
aaaattgatcattttagtggatgacttgcccaagacaagatccggcaaattatgagacgtattttaagaaaaatc
ctagcaggagaaagtgaccaactaggcgacgtttctacattgtcaaaccctggcattgttagacatctaattgatt
cggtcaagttgtaa
```

Spt7-217

SEQ ID No: 19

```
    1 MTERIPIKNY QRTNAKALLK LTEKLFNKNF FDLYLTSQQL VVLEYLLSIS SEEDKLKAWD
   61 YFLKGNIALN VEKSFPLTQE EEHGAVSPA VDTRSDDVSS QTIKDNNNTN TNTSISNENH
  121 VENEIEDKGD NAIANEDNFV NNDESDNVEE DLFKLDLEDL KQQISGTRFI GNLSLKIRYV
  181 LWQCAIDYIY CDRNEFGDEN DTEYTLLDVE EKEEEEIGKN EKPQNKEGIS KFAEDEDYDD
  241 EDENYDEDST DVKNVDDPPK NLDSISSSNI EIDDERRLVL NISISKETLS KLKTNNVEEI
  301 MGNWNKIYHS FEYDKETMIK RLKLEESDKM IEKGKKKRSR SDLEAATDEQ DRENTNDEPD
  361 TNQKLPTPEG STFSDTGNKR PKQSNLDLTV NLGIENLSLK HLLSSIQQKK SQLGISDYEL
  421 KHLIMDVRKN RSKWTSDERI GQEELYEACE KVVLELRNYT EHSTPFLNKV SKREAPNYHQ
  481 IIKKSMDLNT VLKKLKSFQY DSKQEFVDDI MLIWKNCLTY NSDPSHFLRG HAIAMQKKSL
  541 QLIRMIPNIT IRNRADLEKE IEDMEKDKDY ELDEEEEVAG SGRKGLNMGA HMLAKENGKV
  601 SEKDSSKTVK DEAPTNDDKL TSVIPEGEKE KDKTASSTVT VHENVNKNEI KENGKNEEQD
  661 MVEESSKTED SSKDADAAKK DTEDGLQDKT AENKEAGENN EEEEDDDDED EDEDMVDSQS
  721 YLLEKDDDRD DLEISVWKTV TAKVRAEICL KRTEYFKNGK LNSDSEAFLK NPQRMKRFDQ
  781 LFLEYKEQKA LESYRQKIEQ NSIMKNGFGT VLKQEDDDQL QFHNDHSLNG NEAFEKQPND
  841 IELDDTRFLQ EYDISNAIPD IVYEGVNTKT LDKMEDASVD RMLQNGINKQ SRFLANKDLG
  901 LTPKMNQNIT LIQQIRHICH KISLIRMLQS PLSAQNSRSN PNAFLNNHIY NYTIIDDSLD
  961 IDPVSQLPTH DYKNNRELIW KFMHKNISKV AMANGFETAH PSAINMLTEI AGDYLSNLIK
 1021 TLKLHHETNS LNRGTNVEML QTTLLENGIN RPDDLFSYVE SEFGKKTKKL QDIKQKLESF
 1081 LRALLRPTLQ ELSERNFEDE SQSFFTGDFA SELTGEDFF
```

SPT7-217 DNA

SEQ ID No: 20

```
atgactgaaagaataccaataaaagaattatcaaagaacaaatgccaaagctttacttaaattgactgaaaaacttt
ttaacaagaacttttttgatctctatttaacctctcagcaattggtcgttcttgaatacctgctgtcgatttcaag
tgaagaagacaaactgaaagcatgggactattcttaaagggaaacatagcattaaatgtcgaaaatcatttcca
ttaacccaagaagaagaacatcacggagcggtctctcctgccgttgacacacgatcagatgatgtatcatcacaaa
caattaaggacaataacaatactaataccaacaccagtatcagcaattcatgttgaaaatgaaattgaaga
taaggcgataacgcaatagcaatgaagataattttgtgaataatgacgaaagtgataatgttgaagaagactta
ttcaaattagatctagaggacttgaagcagcaaataagcggaacaaggtttattggaaacttatccttgaaaatca
gatacgtcttgtggcagtcgccatagattatatactgtgatcgtaatgagtttggtgatgaaaatgatacaga
atacacctattagatgttgaagagaaggaagaggaaattggtaaaaatgaacgcacaaaacaaagaaggt
atttcgaagttcgccgaggatgaagattacgacgatgaagacgagaactatgatgaagacagtacagacgtaaaaa
atgtcgatgatcctccaaaaaatctcgattctatttcctcttctaatatcgaaattgacgatgaacgacgcttggt
gctaaatatctcaatatcaaagaaacactgtcaaagttaaaaacaaataatgtagaagaattatgggaaattgg
aacaaaattaccacagttttgaatacgataaagaaactatgataaagcgattaaaactttgaagaaagcgataaaa
tgatagagaaaggaaaagaaagaaacgaagtcgaagtgattgaagcagctaccgatgaacaagatcgcgaaaatac
aaatgatgagccagatactaatcaaaaattgcccactcctgaaggttcaacattcagcgatactgggaacaagcgc
cccaaacaaagtaatttagatttaacagtcaatctaggcatcgaaatttatcattaaagcacctctctcatcta
tccagcaaaaaaatcccaattaggaatatcagattacgaattaaaacatctgattatggatgtcagaaaaatcg
gtcaaaatggacatcggatgaaagaattgggcaagaggaattatacgaagcctgtgaaaaggttgttttggaactt
```

-continued

Sequence Listing

```
agaaactacactgagcattctacaccatttctgaataaagtgagcaaaagagaagcccccaattatcatcaaatca
tcaaaaagtccatggacctgaatactgttttaaaaaaactgaaaagctttcaatatgactccaaacaagaatttgt
agacgatattatgctaatatggaaaaattgtttgacctataattcagatccttcacattttttgagagggcatgct
attgctatgcagaagaaatctcttcagttgattcgcatgattccaaatatcacaatccgaaacagggctgatttag
aaaaggaaattgaagatatggaaaaagacaaagactacgaattagatgaggaagaggaagttgctggttctggaag
aaaaggattgaatatgggagctcatatgttggccaaagagaatggcaaggtgtcagaaaaagatagctctaaaacc
gtcaaggatgaagcaccaaccaatgatgacaaactaacttctgtcatccctgagggggaaaaagaagaaagataaaa
ctgcttcatctactgtaacggtacacgaaaatgtaaataagaacgaaataaaagaaaatgggaaaaatgaagagca
agatatggttgaggaaagtagtaagactgaggattcatcaaaagatgctgatgctgccaaaaaggatacggaagac
ggactacaagataaaactgcagaaaataaggaggctgggaaaataatgaagaggaagaggatgatgatgacgaag
atgaagacgaagacatggtcgactcccaatcttatttacttgaaaaggatgacgatagagacgatttggaaatatc
cgtgtgtgaaaactgtaactgccaaagttcgtgcggaaatttgcttaaaaagaactgaatattttaaaaatggaaaa
ttaaatagtgattcagaggcgttttttgaaaaacccacaaagaatgaaaaggttcgaccagcttttttcttgaatata
aagagcagaaagctttagaatcatatcgtcaaaaaatagagcaaaattccattatgaaaaatggctttgaacagt
actaaaacaggaagacgatgaccaattgcagtttcataatgatcactcttttaaatggaaatgaagcttttgaaaag
caacccaatgatattgagttagatgataccagattcctacaggaatatgatattagtaacgccattcctgacatag
tatacgagggagtaaatactaaaacattagacaagatggaagacgcttccgtggaccgcatgcttcaaaatggtat
caacaaacaaagcagatttctggctaacaaggatttaggactaacacctaaaatgaaccaaaatatcacactgatt
cagcaaattaggcacatatgccataaaaatatccctgatcgaatgttacagagccctttatcggctcaaaactcca
gaagcaatcccaacgctttccttaacaaccacatttataattacactattattgatgactcactcgatattgatcc
ggtgtcacagcttccaacgcatgattacaaaaacaacagggagctgatatggaaattcatgcataagaacatatct
aaggttgctatggccaatgggtttgaaactgcccatccatcagcaataaacatgcttactgaaatcgccggggatt
acctatctaatctgataaagactttgaagcttcatcatgaaactccttaaatagaggaacaaatgtggaaat
gctgcaaacaacactgttggaaaacggtatcaacaggccagacgatctatttttcctatgttgaatctgaatttggt
aaaaaaactaagaaacttcaggacatcaaacagaaactagaaagcttttttgagagccttattaaggccaactttgc
aggagttgtccgagagaaactttgaagacgagagccaaagcttttttacaggtgactttgccagcgaattgactgg
tgaagacttcttt
```

Spt3

```
                                                                 SEQ ID No: 21
  1 MMDKHKYRVE IQQMMFVSGE INDPPVETTS LIEDIVRGQV IEILLQSNKT AHLRGSRSIL
 61 PEDVIFLIRH DKAKVNRLRT YLSWKDLRKN AKDQDASAGV ASGTGNPGAG GEDDLKKAGG
121 GEKDEKDGGN MMKVKKSQIK LPWELQFMFN EHPLENNDDN DDMDEDEREA NIVTLKRLKM
181 ADDRTRNMTK EEYVHWSDCR QASFTFRKNK RFKDWSGISQ LTEGKPHDDV IDILGFLTFE
241 IVCSLTETAL KIKQREQVLQ TQKDKSQQSS QDNTNFEFAS STLHRKKRLF DGPENVINPL
301 KPRHIEEAWR VLQTIDMRHR ALTNFKGGRL SSKPIIM
```

Spt3

```
                                                                  SEQ ID No: 22
atgatggacaagcataagtatcgtgtggagattcaacgatgatgtttgtctctggtgaaattaacgacccacccgtagaa
accacatcactgatagaagatatagtgaggggtcaagtgatagaaattcttttacagtcaaacaaaacggcgcatcttagg
ggaagtaggagcattctccctgaagacgtcatttcttgatcagacacgacaaggccaaagtcaatcgtttgagaacatat
ctgtcatggaagatttgcgtaaaaacgccaaggaccaagatgctagtgccggtgtagcgagtggcactggaaatcctggg
gcaggtggtgaagatgatttgaaaaaagcaggtggtggcgagaaagacgaaaaagatggtggaaacatgatgaaggtcaag
aaatcccaaattaagctgccatgggaattgcagtttatgttcaatgaacatcccttagaaaataatgacgacaatgatgat
atggatgaggatgaacgagaagctaatatagtcactttgaaaaggctgaaaatggctgacgatagaacgaaacatgact
aaagaggagtacgtgcattggtccgattgtcgacaggcaagttttacatttaggaagaataaaaggttcaaggactggtct
ggaaatttcgcaattaactgaggggaaaccccatgatgatgtgattgatatactggggttctaacttttgagattgtctgt
tctttgacggaaacagctctgaaaatcaaacaaagagaacaggtattacagactcaaaaggacaaatcccagcaatctagc
caagataatactaactttgaatttgcatcatccacattacatagaaagaaaagattatttgatggacctgaaaatgttata
aacccgctcaaaccaaggcatatagaggaagcctggagagtactacaaacaattgacatgaggcatagggctttgaccaac
tttaaaggtggtagactcagttctaaaccaattatcatgtaa
```

The invention claimed is:

1. A method for increasing a chronological lifespan of a cell comprising disrupting a function the Spt-Ada-Gcn5-Acetyltransferase complex in said cell, wherein the complex is disrupted by disrupting the function of the Spt7 gene or homologue thereof.

2. The method according to claim 1 wherein the at least one complex is directly or indirectly disrupted.

3. The method according to claim 1, wherein the function of the gene is disrupted by iRNA.

4. The method according to claim 1, wherein the function of the gene is disrupted at a transcriptional/DNA level.

* * * * *

UNITED STATES PATENT AND TRADEMARK OFFICE
CERTIFICATE OF CORRECTION

PATENT NO.      : 8,628,922 B2  
APPLICATION NO. : 13/382629  
DATED           : January 14, 2014  
INVENTOR(S)     : Elizabeth Jane Mellor Page 1 of 1

It is certified that error appears in the above-identified patent and that said Letters Patent is hereby corrected as shown below:

In the Claims

Column 111, line 23, Claim 2 should read:

2. The method according to claim 1 wherein the complex is directly or indirectly disrupted.

Signed and Sealed this
Fifth Day of August, 2014

Michelle K. Lee
*Deputy Director of the United States Patent and Trademark Office*